United States Patent
Gale et al.

(10) Patent No.: US 7,122,572 B2
(45) Date of Patent: Oct. 17, 2006

(54) CALIXPYRROLES

(75) Inventors: Philip A. Gale, Austin, TX (US);
Jonathan L. Sessler, Austin, TX (US);
Vladimír A. Král, Praha (CZ); Andrei Andrievsky, Rochester, NY (US);
Vincent Lynch, Austin, TX (US); Petra I. Sansom, Edgewater, NJ (US);
William E. Allen, Austin, TX (US);
Christopher T. Brown, Austin, TX (US); Andreas Gebauer, Austin, TX (US)

(73) Assignee: Board of Regents, University of Texas System, Austin, TX (US)

( * ) Notice: Subject to any disclaimer, the term of this patent is extended or adjusted under 35 U.S.C. 154(b) by 0 days.

(21) Appl. No.: 09/838,998

(22) Filed: Apr. 20, 2001

(65) Prior Publication Data

US 2002/0026047 A1    Feb. 28, 2002

Related U.S. Application Data

(62) Division of application No. 08/833,379, filed on Apr. 4, 1997, now Pat. No. 6,262,257.

(60) Provisional application No. 60/033,395, filed on Dec. 17, 1996, provisional application No. 60/033,396, filed on Dec. 17, 1996, provisional application No. 60/026,694, filed on Sep. 25, 1996, provisional application No. 60/024,203, filed on Aug. 27, 1996, provisional application No. 60/014,890, filed on Apr. 5, 1996.

(51) Int. Cl.
*A61K 31/40* (2006.01)
*C07D 487/22* (2006.01)

(52) U.S. Cl. ..................... 514/427; 540/145
(58) Field of Classification Search ........... 540/145; 514/427
See application file for complete search history.

(56) References Cited

U.S. PATENT DOCUMENTS

| 5,808,059 A | 9/1998 | Sessler et al. |
| 6,262,257 B1 | 7/2001 | Gale et al. |

FOREIGN PATENT DOCUMENTS

| EP | 0 233 701 | 8/1987 |
| WO | WO 89/08092 | 9/1989 |
| WO | WO 93/13150 | 7/1993 |

OTHER PUBLICATIONS

Allen, et al., "Binding of Neutral Substrates by Calix[4]pyrroles," *J. Am. Chem. Soc.*, vol. 118, No. 49, pp. 12471-12472, Sep., 1996, American Chemical Society.

Andreeti, G., "Crystal and Molecular Structure of Cyclo{quater [(5-t-butyl-2-hydroxy-1,3-phenylene)methylene]} Toluene (1:1) Clathrate," *J.C.S. Chem. Comm.*, 1005-1007, 1979, The Royal Society of Chemistry.

Asfari, et al., "Quick Synthesis of the First Double Porphyrin Double Calix[4]arene," *Tetrahedron Letters*, vol. 34, No. 4, pp. 627-628, 1993, Elsevier Science Ltd.

Baeyer, A., "Ueber ein Condensationsproduct von Pyrrol mit Aceton," *Ber. Dtsch. Chem. Ges.*, 19:2184-2185, 1886, The Royal Society of Chemistry.

Beer, et al, "A Neutral Upper to Lower Rim Linked Bis-Calix[4]arene Receptor that Recognises Anionic Guest Species," *Tetrahedron Letters*, vol. 36, No. 5, pp. 767-770, Jan., 1995, Elsevier Science Ltd.

Beer, et al., "Anion Recognition by Novel Ruthenium(II) Bipridyl Calix[4]arene Receptor Molecules," *J. Chem. Soc.*, Chem. Commun., 1269-1271, 1994, The Royal Society of Chemistry.

Beer, et al., "Anion Recognition by Redox-Responsive Ditopic Bis-Cobaltocenium Receptor Molecules Including a Novel Calix[4]arene Derivative That Binds a Dicarboxylate Dianion," *Organometallics*, 14:3288-3295, Jul., 1995, American Chemical Society.

Beer, et al., "Structures of Potassium encapsulated within the 1,3-Alternate Conformation of Calix[4]arenes," *J. Chem. Soc. Dalton Trans.*, 3479-3485, 1994, The Royal Society of Chemistry.

Beer, et al., "Synthesis and Co-ordination Chemistry of a Novel Bis (Benzo Crown Ether) Substituted Calix[4]arene that can Simultaneously Complex Cations and Anions," *J. Chem. Soc. Dalton Trans.*, 3117-3123, Oct., 1995, The Royal Society of Chemistry.

Böhmer, V., "Calixarenes, Macrocycles with (Almost) Unlimited Possibilities," *Angew. Chem. Intl. Ed. Engl.*, 34:713-745, Jul., 1995, VCH Verlagsgesellschaft.

(Continued)

*Primary Examiner*—Joseph K. McKane
*Assistant Examiner*—Rebecca Anderson
(74) *Attorney, Agent, or Firm*—Akin Gump Strauss Hauer & Feld, LLP

(57) ABSTRACT

The present invention provides calixpyrrole, calixpyridinopyrrole, and calixpyridine macrocycles, having 4, 5, 6, 7, or 8 heterocyclic rings, as well as syntheses, derivatives, conjugates, multimers, and solid supports thereof. Such macrocycles have proved to be effective and selective ion- and neutral molecule-binding agents forming supramolecular ensembles, and ion- and neutral molecule-separation agents. The macrocycles are fully meso-non-hydrogen-substituted porphyrinogens, a few molecules of which were previously known but not recognized as possessing anion- or molecule-binding properties. The binding mode is noncovalent, primarily that of hydrogen-bonding, thereby providing a new mode for liquid chromatography, that of Hydrogen Bonding Liquid Chromatography. Further useful applications of the macrocycles provided herein include environmental remediation by removal of undesired ions or neutral molecules, and removal of phosphate for kidney dialysis.

29 Claims, 30 Drawing Sheets

OTHER PUBLICATIONS

Bonar-Law, R., "Porphyrin Synthesis in Surfactant Solution: Multicomponent Assembly in Micelles," *J. Org. Chem.*, 61:3623-3634, Jan., 1996, American Chemical Society.

Brown, et al., "The Condensation of Cyclohexanone with Furan and Pyrrole," *Canadian J. of Chem.*, 49:4017-4022, 1971, N R C Research Press.

Chelintzev, B., and Tronov, V., "Simple condensation of pyrrole with methylethyl ketone and methylhexyl ketone, mixed condensation with acetone and methylethyl ketone, and relation of these reactions to the determination of the formulas of chlorophyll and hemin," *J. Russian Physical Chem. Soc.*, 48:1197-1209, 1916, Chemical Abstracts only, p. 1418, American Chemical Society.

Chelintzev, V.V., and Tronov, B.V., "Process of condensation of pyrrole and acetone. Constitution of the resulting products," *J. Russian Physical Chem. Soc.*, 48:105-155, 1916, Chemical Abstracts only, pp. 452-454, American Chemical Society.

Chen, et al., "Synthesis and electrochemical polymerization of calix[4]arenes containing N-substituted pyrrole moieties," *J. Electroanalytical Chem.*, 393: 113-117, Aug., 1995, Elsevier Science.

Crescenzi, et al., "The $N_2O_2$ porphyrinogen skeleton: Access to a novel class of coordinatively unsaturated transition metal ions," *Inorganic Chem.*, 35:2413-2414, Apr. 1996, American Chemical Society.

DeAngelis, et al., "A $Li_2Ti_2$-substituted acetylene formed from ethylene by reaction with (meso-octaethyl porphyrinogen)titanium," *Angewante Chemie*, International Edition, English, 34:1092-1094, Jun., 1995 V C H Verlagsgesellschaf.

De Angelis, et al., "Solvent-dependent Forms of Lithiated 5,5,10,10,15,15,20,20-Octaethylporphyrinogen in Solution and in the Solid State and Reaction with Tetrahydrofuran," *J. Chem. Soc., Dalton Trans.*, 2467-2469, 1994, The Royal Society of Chemistry.

DeAngelis, et al., "Organometallic chemistry of a titanium (IV) meso- octaethylporphyrinogen complex: Carrier properties of polar organometallics and their behavior in insertion reactions," *Organometallics*, 14:4505-4512, Oct. 1995, American Chemical Society.

DeAngelis, et al., "Oxidation of metal-*meso*-octaethylporphyrinogen complexes leading to novel oxidized forms of porphyrinogen other than porhyrins. 2. The redox chemistry of iron (II)- and cobalt (II)-*meso*-octaethylporphyrinogen complexes occurring with the formation and cleavage of two cyclopropane units," *J. Am. Chem. Soc.*, 116:5702-5713, 1994, American Chemical Society.

DeAngelis, et al., "Oxidation of metal-*meso*-octaethylporphyrinogen complexes leading to novel oxidized forms of porphyrinogen other than porphyrins. 1. The redox chemistry of nickel(II)- and copper (II)-*meso*-octaethylporphyrinogen complexes occurring with the formation and cleavage of a cyclopropane unit," *J. Am. Chem. Soc*, 116:5691-5701, 1994, American Chemical Society.

Dennstedt, M., and Zimmermann, J., "Ueber die Einwirkung des Acetons auf das Pyrrol," *Ber. Dtsch. Chem Ges.*, 20:850-857, 1887, The Royal Society of Chemistry.

Dietrich, et al., "Macrocyclic Chemistry", *VCH*, New York, p. 82 and p. 160, 1993, VCH Verlagsgesellschaft.

Floriani, C., "The discovery and future prospects of artificial porphyrins: Molecular batteries functioning with the reversible formation and cleavage of cyclopropane units," *Chimia*, 50:608-611, Dec. 1996, Neue Schweizerische Chemische Gesellschaft.

Floriani, C., "The porphyrinogen-porphyrin relationship: the discovery of artificial porphyrins," *Chem Commun.*, 1257-1263, Jun., 1996, The Royal Society of Chemistry.

Floriani, C., "Transition metal complexes as bifunctional carriers of polar organometallics: Their application to large molecule modifications and to hydrocarbon activation," *Pure and Applied Chem.*, 68:1-8, Jan. 1996, (IUPAC), Blackwell Science Ltd.

Fujimoto, et al., "Synthesis and Crystallographic Studies of a Calix[4]arene with a 1,3-Alternate Conformation," *J. Chem. Soc., Perkin Trans. 2*, pp. 643-648, 1992, Royal Society of Chemistry.

Gale, et al., "Calix[4]pyrroles: C-rim substitution and tunability of anion binding strength," *Chem. Commun.*, pp. 665-666, 1997, The Royal Society of Chemistry.

Gale, et al., "Calix[4]pyrroles: Old Yet New Anion-binding Agents," *J. Am. Chem. Soc.*, vol. 118, No. 21, pp. 5140-5141, Jan., 1996, American Chemical Society.

Gale, et al., "Calixprroles: old yet new anion binding agents," 31st *Int'l Conf. on Coordination Chemistry*, University of British Columbia, Vancouver, Canada, Aug. 18, 1996, publisher unknown.

Gale, et al., "New Applications for Calixpyrroles," *Royal Soc. Chem. U.K. Macrocycles Group Annual General Mtg.*, University of Wales, Cardiff, Wales, U.K., Dec. 18, 1996, Royal Society of Chemistry.

Gale, et al., "Synthesis of a New Cylindrical Calix[4]arene-Calix[4]pyrrole Pseudo Dimer," *Tetrahedron Letters*, vol. 37, No. 44, pp. 7881-7884, Sep. 1996, Elsevier Sciences Ltd.

Ghidini, et al., "Complexation of Alkai Metal Cations by Conformationally Rigid, Stereoisomeric Calix[4]arene Crown Ethers: A Quantitative Evaluation of Preorganization," *J. Am. Chem. Soc.*, 112:6979-6985, 1990, American Chemical Society.

Golder, et al., "5,10,15,20-*meso*-tetrakis(3,5-di-t-butyl-4-quinomethide)porphyrinogen: a highly puckered tetrapyrrolic macrocycle from the facile aerial oxidation of a phenolic porphyrin," *J. Chem. Soc.*, Chemical Communications, 1751-1753, 1989, The Royal Society of Chemistry.

Isoz, et al., "Niobium-carbon functionalities supported by *meso*-octaethylporphyrinogen and derived macrocycles," *Organometallics*, 15, 337-344, Jan. 1996, American Chemical Society.

Jacoby, et al., "Bifunctional carriers of organometallic functionalities: alkali-metal-zirconium-hydrido,-alkyl, and -allyl derivatives of *meso*-octaethylporphyrinogen and their reaction with isocyanides," *Organometallics*, 14:4816-4824, Oct. 1995, American Chemical Society.

Jacoby, et al., "Electrophilic activation of aliphatic C-H bonds mediated by zirconium hydride entities and applied to the functionalization of the porphyrinogen periphery," *J. Amer. Chem. Soc.*, 117:2805-2816, Mar. 1995, American Chemical Society.

Jacoby, et al., "Macrocyclic modification using organometallic methodologies. Regiochemically controlled mono- and bis-homologation reactions of porphyrinogen with carbon monoxide assisted by early transition metals," *J. Amer. Chem. Soc.*, 117:2793-2804, Mar. 1995, American Chemical Society.

Jacoby, et al., "*meso*-Octamethylporphyrinogen metal complexes: an entry to high valent unsaturated metal centres," *J. Chem. Soc.*, Chemical Communications, 220-222, 1991, The Royal Society of Chemistry.

Jacoby, et al., "The π and σ Bonding Modes of *meso*-Octaethylporphyrinogen to Transition Metals: the X-ray Structure of a *meso*-Octaethylporphyrinogen-Zirconium (IV) Complex and of the Parent *meso*-octaethylporphyrinogen Ligand," *J. Chem. Soc., Chem. Comm.*, pp. 790-792, 1991, The Royal Society of Chemistry.

Jacoby, et al., "Zirconium *meso*-octaethylporphyrinogen as a carrier for sodium hydride in toluene: Zirconium-sodium bimetallic hydride and alkyls," *J. Am. Chem. Soc.*, 115:3595-3602, 1993, American Chemical Society.

Jones, R.L. and Rees, C.W., "Mechanism of heterocyclic ring expansions. Part III. Reaction of pyrroles with dichlorocarbene," *J. Chem. Soc.*, 2249-2251, 1969, The Royal Society of Chemistry.

Jones, R.L. and Rees, C.W., "Mechanism of heterocyclic ring expansions. Part IV. Reaction of an imidazole,.pyrazole and 1,2,4-triazole with dichlorocarbene," *J. Chem. Soc.*, 2251-2255, 1969, The Royal Society of Chemistry.

Jones, R.L. and Rees, C.W., "Mechanism of heterocyclic ring expansions. Part V. Base catalysed rearrangement of 2-dichloromethyl-2,5-dimethyl-2H-pyrrole and related compounds," *J. Chem. Soc.*, 2255-2259, 1969, The Royal Society of Chemistry.

Jubb, et al., "Preparation of reactivity of the first yttrium porphyrinogen complex," *J. Chem. Soc.*, Chemical Comm., 2641-2642, 1994, The Royal Society of Chemistry.

Jubb, et al., "Redox chemistry of *meso*-octaetylporphyinogen: Formation and opening of a cyclopropane ring," *J. Am. Chem. Soc.*, 114:6571-6573, 1992, American Chemical Society.

Jubb, et al., "Lithum-Transition metal Complexes Derived from meso-Octaethylporphyrinogen Which Display α- and π- Bonding Modes," *Inorganic Chem.*, 31:1306-1308, 1992, American Chemical Society.

Kamlet et al., "Linear Solvation Energy Relationships. 23. A Comprehensive Collection of the Solvatochromic Parameters, $\pi^*$, α, and β, and Some Methods for Simplifying the Generalized Solvatochromic Equation," *J. Org. Chem.*, 48:2877-2887, 1983, American Chemical Society.

Kobayashi et al., "A 'calix[4]arened' porphyrin as a new host and an oxygen carrier model," *Inorganica Chimica Acta*, 224:1-3, 1994, Elsevier Science, Ltd.

Kursanov, N.I., "Cyclehexyl phenyl ether and its isomerization to cyclohexylphenol," *J. Russ. Phys. Chem. Soc.*, 48:1172-1174, 1916, Chemical Abstracts only, American Chemical Society.

Marx, T. and Breitmaier, E., "A Porphyrinogen bridged with and a Porphyrin Subsbituted by 1,8-diethynylanthracene," *Liebigs Ann. Chem.*, pp. 857-858, 1994, V C H Verlagsgesellschaft.

Marx, T. and Breitmaier, E., "Ein Porphyrinogen mit 1,8-Diphenylanthracen-Brücke," *Liebigs Ann. Chem.*, pp. 1041-1042, 1993, V C H Verlagsgesellschaft.

Morzherin, et al., "Chlorosulfonylated Calix[4]arenes: Precursors for Neutral Anion Receptors with a Selectivity for Hydrogen Sulfate," *J. Org. Chem.*, 58:7602-7605, 1993, American Chemical Society.

Nagasaki et al., "Calix[4]arene-Capped Tetraphenylporphyrin: Synthetic Approach to a Chiral Capped Porphyrin with Regular $C_4$ Symmetry," *Chem. Letters*, pp. 989-992, 1994, The Chemical Society of Japan.

Nagasaki, et al., "Design and synthesis of a $C_4$-symmetrical hard-soft ditopic metal receptor by calixarene-porphyrin coupling," *J. Chem. Soc. Perkin Trans.*, 1:1883-1888, Aug. 1995, Royal Society of Chemistry.

Pappalardo, et al., "Novel 1,2-Bridged Calix[4]crowns in the 1,2-Alternate Conformation," *Tetrahedron Letters*, vol. 37, No. 22, pp. 3907-3910, May, 1996, Elsevier Sciences Ltd.

Piarulli, et al., "Redox chemistry associated with the compexation of vanadium (V) and tungsten (VI) by meso-octaethylporphyrinogen: Formation and cleavage of cyclopropane units functioning as shuttles of two electrons," *J. Am. Chem. Soc.*, 118:3634-3642, Mar. 1996, American Chemical Society.

Piarulli, et al., "The Four-electron Oxidation of meso-Octaethylporphrinogen via a Metal-mediated Dealkylation Process: Formation of [RuL(PhCN)$_2$][H$_2$L=5, 15-dihydro-5,5,10,15,15,20-hexaethylporphyrin]," *J. Chem. Soc.*, Chem. Comm., 895-896, 1994, Royal Society of Chemistry.

Rees, C.W. and Smithen, C.E., "The mechanism of heterocyclic ring expansions. Part I. The reaction of 2,3-dimethylindole with dichlorocarbene," *J. Chem. Soc.*, 928-937, 1964, Royal Society of Chemistry.

Rees, C.W. and Smithen, C.E., "The mechanism of heterocyclic ring expansions. Part II. The reaction of methylindoles with halogenocarbenes," *J. Chem. Soc.*, 938-945, 1964, Royal Society of Chemistry.

"Removal and recovery of toxic metal ions from aqueous waste streams by utilization of polymer pendant liganda," *Internet*, Posted Oct. 10, 1995, publisher unknown.

Rosa, et al., "The α- and π- bonding modes of a tetraanionic porphyrinogen ligand in zirconium (IV) complexes: a theoretical investigation," *J. Chem. Soc.*, Dalton Transactions, 3759-3766, 1993, Royal Society of Chemistry.

Rothemund, P.and Gage, C.L., "Concerning the structure of Acteone-pyrrole," *J. Am. Chem. Soc.*, 77:3340-3342, 1955, American Chemical Society.

Rudkevich, et al., "Biscalix[4]arene-Zn-tetaarylporphyrins," *Tetrahedron Letters*, vol. 35, No. 38, pp. 7131-7134, 1994, Elsevier Sciences Ltd.

Scheerder, et al., "Complexation of Halide Anions and Tricarboxylate Anions by Neutral Urea-Dervatized p-tert-Butylcalix[6]arenes," *J. Org. Chem.*, 60:6448-6454, Oct. 1995, American Chemical Society.

Sessler, et al., "Anion Binding: Self-Assembly of Polypyrrolic Macrocycles," *Angew. Chem. Int. Ed. Engl.* 35:2782-2785, Jun. 1996, V C H Verlagsgesellschaft.

Solari, et al., "Bifunctional carriers of alkali-metal enolates: The use of zirconium meso-octaethylporphyrinogen in aldol condensation reactions," *Organometallics*, 16:508-510, 1997, American Chemical Society.

Solari, et al., "Functionalizable 5,5,10,10,15,15,20,20-octaethylporphyinogen complexes of early transition metals: Synthesis and Crystal Structure of titanium-, vanadium-, and chromium (III) derivatives and a two-electron oxidation of the porphyrinogen skeleton," *J. Chem. Soc.*, Dalton Transactions, 2015-2017, 1994, Royal Society of Chemistry.

Steed, et al., "A Water-Soluble "Bear Trap" Exhibiting Strong Anion Complexation Properties," *Angew. Chem. Int. Ed., Engl.*, 33:2456-2457, 1994, V C H Verlagsgesellschaft.

Von Maltzan, B., "Synthesis of 2,3,7,8,12,13,17,18-octamethyl-porphyrinogen in almost quantitative yield," *Angewante Chemie*, International Edition, English, 785-786, 1982, V C H Verlagsgesellschaft.

Xu, et. al., "Inorganic Inclusion Chemistry: A Novel Anion Inclusion System," *J. Am. Chem. Soc.*, 117:8362-8371, Aug. 1995, American Chemical Society.

Dialog Search, Mar. 25, 1997, DIALOG ®Corp.

Chelintzev, et. al., "Simple condensation of pyrrole with cyclohexanone and other cyclic ketones in mixed condensation with acetone and cyclohexanone, and conclusions in respect to the ability of different ketones to condense with pyrrole," *J. Russ. Phys. Chem. Soc.*, 48:1210-1221, 1916, Chemical Abstracts only, pp. 1418-1419, American Chemical Society.

Gutsche, C. David, "Calixarenes," *Monographs in Supramolecular Chemistry*, ix-xii, Title Page and Table of Contents only, 1989, Royal Society of Chemistry.

No, et. al., "Synthesis and Molecular Structure of Calix[4]arene Butanoate 1,2-Alternate Conformer," *Bull. Korean Chem. Soc.*, 17:447-452, 1996, Korean Chem. Scoiety.

Sessler, et al., "Calixpyrroles: Old Yet New Anion Binding Agents," *XXI International Symposium on Macrocyclic Chemistry*, PB 29:158, Jun. 23-28, 1996, publisher unknown.

PCT International Search Report, Appl. No. PCT/US 97/05643, Aug. 13, 1997.

Aoyama, et al., "Multi-Point Interaction of Phosphates with Protonated Pyridylporphyrin Discrimination of Monoalkly and Dialkyl Phosphates," *Chemistry Letters*, pp. 1241-1244, 1991, The Chemical Society of Japan.

Vogel, et al., "2,7,12,17-Tetraproplyporphycene-Counterpart of Octaethylporphyrin in the Porphycene Series," *Angew. Chem. Int. Ed. Engl.*, 26, No. 9, pp. 928-931, 1987, V C H Verlagsgesellschaft.

Vogel, et al., "New Porphycene Ligands: Octaethyl- and Etioporphycene (OEPc and EtioPc)—Tetra—and Pentacoordinated Zinc Complexes of OEPc," *Angew. Chem. Intl. Ed. Engl.*, 32, No. 11, pp. 1600-1604, 1993, V C H Verlagsgesellschaft.

Pending Application in India; No. 708/MAS/97 to Gale et al. filed Apr. 3, 1997.

Furusho, et al., "Molecular Design and Functions of Novel Porphyrinogens," 67th *Annual Meeting of the Chemical Society of Japan, Tokyo, Abstract 3D238*, 1994 (in Japanese with English translation); The Chemical Society of Japan.

Furusho et al., "Guest responsive structural changes of porphyrinogen inclusion crystals: a longrange cooperative effect on guest inclusion," *Chemical Communications*, No. 22, pp. 2205-2206, p. vii, and cover page, Nov. 21, 1997, Royal Society of Chemistry.

Gale, et al., "Calixpyrroles," *Chem. Comm.*, pp. 1-8, 1998, Royal Society of Chemistry.

Iverson, et al., "Molecular Recognition of Anionic Species by Silica Gel Bound Sapphyrin," *J. Am. Chem. Soc.*, vol. 116, pp. 2663-2664, 1994, American Chemical Society.

Sessler, et al., "Calix[4]pyrroles: New Solid-Phase HPLC Supports for the Separation of Anions," *Chem. Eur. J*, vol. 4, No. 6, pp. 1095-1099, 1998, Wiley-VCH Verlag.

Beer et al., "Synthesis and X-Ray Crystal Structure of a New Redox-active Calix[5]arene Containing a Totally Included Ethanol Molecule", J. Chem. Soc., Chem. Commun., pp. 1851-1852, (1995), The Royal Society of Chemistry.

Freemantle, Micheal, "Calixarene Family Enbraces New Cousins", Chemical & Engineering News, vol. 76, No.7, pp. 31-32, (1998), American Chemical Society.

Gutsche et al., "Calixarenes. 4. The Synthesis, Characterization, and Properties of the Calixarenes from p-tert-Bulylphenol", J. Am. Chem. Soc., vol. 103, No. 13, pp. 3782-3792, (1981), American Chemical Society.

CALIXPYRROLES

CROSS-REFERENCE TO RELATED APPLICATIONS

The present application is a divisional application of U.S. Ser. No. 08/833,379 filed Apr. 4, 1997, now U.S. Pat. No. 6,262,257, issued Jul. 17, 2001. U.S. Ser. No. 08/833,379 claims priority to then copending U.S. Ser. No. 60/014,890 filed Apr. 5, 1996; U.S. Ser. No. 60/024,203 filed Aug. 27, 1996; U.S. Ser. No. 60/026,694 filed Sep. 25, 1996; U.S. Ser. No. 60/033,395 filed Dec. 17, 1996; and U.S. Ser. No. 60/033,396 filed Dec. 17, 1996.

The government owns certain rights in the present invention pursuant to grant number CHE122161 from the National Science Foundation, grant number AI33577 from the National Institutes of Health, a GANN fellowship from the Department of Education, and a postdoctoral research scholarship from the Fulbright Commission.

FIELD OF THE INVENTION

The present invention relates generally to the fields of separation technology, environmental remediation, and biomedical applications such as dialysis and drug delivery. More particularly, it concerns ion- and neutral molecule-binding, ion- and neutral molecule-separation or ion- and neutral molecule-detection, using calix[n]pyrrole, calix[m]pyridino[n]pyrrole, or calix[m]pyridine macrocycles. A new type of liquid chromatography is provided herein, that of Hydrogen Bonding Liquid Chromatography, that is based on noncovalent interactions and provides efficient and effective separation of heretofore difficult-to-separate anions and molecules.

BACKGROUND OF THE INVENTION

Anions play essential roles in biological processes; indeed, it is believed that they participate in 70% of all enzymatic reactions. There is, therefore, intense effort being devoted to the problem of anion complexation and recognition. In the molecular recognition arena, a number of research groups have followed Nature's lead and have designed and synthesized receptors that use hydrogen bonds alone, or in concert with electrostatic interactions, to coordinate to anions. Nonetheless, there remains at present a critical need for additional anion complexing agents that are either easy to make or inherently selective in their substrate binding properties.

Additionally, the separation of anionic mixtures using chromatographic techniques involving anion binding interactions is a little studied area of chemistry. Current techniques for purification of anions such as oligonucleotide fragments, polyphosphate-containing molecules such as ATP, ADP and AMP, carboxylates, or N-protected amino acids involve derivatization prior to separation, leading to decreased yields and cumbersome methodology, or involve a salts separation step following chromatography. This is a very important area to both scientists and clinicians as both mono- and di-nucleotides, natural and synthetic oligonucleotides play critical roles in modern biotechnology as well as medicine. Oligonucleotides are used, for instance, as hybridization probes in blot analyses, primers for PCR amplification, and for site-specific mutagenesis. Furthermore, in some areas, oligonucleotide-derived products are currently being used as probes for the detection of genetic diseases and for proviral HIV, the causative agent of Acquired Immunodeficiency Syndrome (AIDS). Oligonucleotides are also being considered as potential chemotheraputic agents, both directly, i.e., in gene therapy, and in an antisense fashion.

The above-mentioned applications require oligonucleotide materials of impeccable purity (often greater that >99.99%). Such purity, however, is not readily obtained using existing technology. Presently, gene products and other oligonucleotide-type materials are purified using polyacrylamide gel electrophoresis (PAGE). This approach suffers from the requirement of using toxic materials and is painfully manpower-demanding and low-yielding.

Liquid chromatographic techniques, in particular, high performance liquid chromatography (HPLC) and High Performance Affinity Chromatography (HPAC) employing speciality silica gels are currently used to separate biological molecules. Indeed, silica gel phases with bonded groups, such as linear hydrocarbons, amino groups, cyano-groups, carboxylic amides and amino acids, are all known. Unfortunately, few, if any, of these phases are efficacious for the efficient, high-yielding separation of nucleotides and oligonucleotides. Those that work best for this purpose are ion exchange columns which, on a limited basis, can sometimes separate oligonucleotides containing 40 or fewer residues. However, this technique still suffers from several limitations, including the requirement for severe conditions, such as elution at pH 2.7, for routine operation. The use of high concentration buffers (greater than 1M) and gradients that often include formic acid or formamide, also limits the half-lives of ion exchange columns. Reverse phase columns use column media, such as silica gel with appended groups such as alkyl chains, that separate species on the basis of hydrophobic effects. Reverse phase columns may be used at pressures up to 5000 psi. However, in order to separate species such as oligonucleotides on this type of column, protecting groups must first be appended to the oligonucleotide, and ion-pairing reagents must be used, requiring an additional purification step after the chromatographic separation.

A type of stationary phase has been previously described in which purine and pyrimidine bases are bonded to silica gel. With this support, base-pairing interactions between the nucleic acid base pairs and the modified silica gel were expected to improve the resolution obtained in nucleic acid separation procedures. Although such stationary phases were used to separate nucleic acid-free bases, purine alkaloids, nucleosides, and mono- and oligonucleotides, this approach unfortunately has demonstrated the least success in the case of oligonucleotide separation, which is the most important area. Thus, prior to the present invention, there remained a critical need for improved solid supports that would effectively separate nucleotides and oligonucleotides.

Additionally, sapphyrin (an expanded porphyrin known to bind anions) has been attached to a functionalized silica gel. The separatory properties of this material were not sufficient to separate oligonucleotides successfully due to broad peaks observed for (3- to 9-mer) oligonucleotide mixtures. Furthermore, synthetic challenges are associated with preparing the requisite functionalized sapphyrins since they require over 20 synthetic steps to produce.

Current technology for dialysis in medical applications relies on membranes, such as microfiltering cellophane, to filter anions such as chloride anion or phosphate-containing anions from the blood stream. Aluminum hydroxide or calcium carbonate cocktails must be consumed by the dialysis patient in order to bind the anionic species. A major drawback of this technology is that aluminum builds up in cellular membranes to toxic levels over time causing ailments including dementia and death. Calcium carbonate offers a less toxic substitute, however, it is less efficient and is associated with hypercalcemia.

Water-soluble anion binding agents are desired as drug delivery agents. For examples many anti-viral drugs only show activity when phosphorylated. However, many phosphorylated drug derivatives are too polar to pass through cell wall membranes. A water-soluble anion binding agent may be able to encapsulate the negative charge and so allow the drug to pass through cell walls.

The synthesis of new molecular devices designed to sense and report the presence of a particular substrate is an area of analytical chemistry that is attracting attention. The detection of anionic species is a particular challenge, as anions are difficult to bind and are generally larger than cations leading to a smaller charge-to-radius ratio.

Molecular recognition of neutral compounds presents a challenge in the area of supramolecular chemistry. Binding of substrates, such as short-chain alcohols and simple monoamides, is particularly difficult because these molecules have few functionalized sites available for hydrogen bonding, and they lack the large hydrocarbon surfaces necessary to participate in efficient hydrophobic or π-π stacking interactions. Association constants for neutral substrate-synthetic receptor complexes are thus generally modest, even though the architectural complexity of the receptors is often high.

Cation binding agents may be useful as sensors for particular cations or as sequestering agents. Additionally, particular cation-complexes may be useful in medicine as imaging agents or in the treatment of disease.

One aspect of the present invention involves calixpyrroles. Calixpyrroles represent a subset of a class of macrocycles that was previously termed porphyrinogens. Porphyrinogens are non-conjugated macrocyclic species composed of four pyrrole rings linked in the α-position via $sp^3$ hybridized carbon atoms. Porphyrinogens that carry meso-hydrogen atoms are prone to oxidation to the corresponding porphyrins. Fully meso-non-hydrogen-substituted porphyrinogens are generally stable crystalline materials. The first such macrocycle, meso-octamethylcalix[4]pyrrole, was reported over a century ago by Baeyer (*Ber. Dtsch. Chem. Ges.* 1886, 19, 2184) using a condensation between acetone and pyrrole catalyzed by hydrochloric acid, however, the structure of the molecule was not elucidated. This method was reportedly refined by Dennstedt and Zimmerman (*Ber. Dtsch. Chem. Ges.* 1887, 20, 850) by replacing the hydrochloric acid catalyst with "chlorzink" (presumably zinc chloride) and heating the reaction. Chelintzev and Tronov reportedly produced calix[4]pyrroles by the method of condensing acetone and pyrrole, methylethyl ketone and pyrrole, methylhexylketone and pyrrole and a mixture of acetone and methylethylketone with pyrrole (*J. Russ. Phys. Chem. Soc.* 1916, 48, 1197; *Chem Abstr.* 1917, 11, 1418). Chenlintzev, Tronov and Karmanov reported further production of calixpyrroles by condensing cyclohexanone with pyrrole and a mixture of acetone and cyclohexanone with pyrrole (*J. Russ. Phys. Chem. Soc.* 1916, 48, 1210). Rothemund and Gage reportedly refined Dennstedt and Zimmerman's method by replacing the acid catalyst with methanesulfonic acid (*J. Am. Chem. Soc.* 1955, 77, 3340). Brown, Hutchinson and MacKinnon (*Can. J. Chem.* 1971, 49, 4017) reportedly repeated the synthesis of meso-tetracyclohexylcalix[4]pyrrole and assigned a tetrameric macrocyclic structure. J.-M. Lehn and co-workers have reportedly synthesized meso-octa-3-chloropropylcalix[4]pyrrole by an unpublished procedure and converted it to meso-octa-3-cyanopropylcalix[4]pyrrole (B. Dietrich, P. Viout and J.-M. Lehn in Macrocyclic Chemistry, VCH Publishers, Weinheim, 1993, pg 82). The metal cation binding of deprotonated calix[4]pyrrole macrocycles has been studied by Floriani and co-workers (*Chem. Commun.* 1996, 1257). Floriani has reportedly developed a method for expanding the pyrrole rings of metal-bound deprotonated calix[4]pyrroles forming calix[1]pyridino[3]pyrroles and calix[2]pyridino[2]pyrroles (*J. Am. Chem. Soc.* 1995, 117, 2793). A further prior art method reports using pyrrole, a $C_4$–$C_6$ saturated alicyclic ketone and an acid containing vinyl groups or triple bonds to form a polymerized resin (WO 93/13150). In this case, the resulting products are undefined since it appears to be unknown where the modifying group is attached to the product.

While the term porphyrinogen is now widely accepted in the literature, the present inventors believe the fully meso-non-hydrogen-substituted systems are misnamed. They are not bona fide precursors of the porphyrins and might, therefore, be better considered as being calixpyrroles rather than porphyrinogens. Such a renaming has precedent in the chemistry of other heterocyclic ring systems. Interestingly, while related functionalized calixarenes, a class of molecules containing phenol (as opposed to pyrrole) subunits have been shown to be capable of binding anions, unmodified calixarene frameworks show no affinity for anionic guests, demonstrating that the anion-binding properties are not an inherent part of the calixarene ring structure.

While a few other fully meso-non-hydrogen-substituted porphyrinogens are known, no one prior to the present inventors recognized their properties and consequent uses as described herein.

SUMMARY OF THE INVENTION

The present invention results from the inventors' discovery that calix[4]pyrrole macrocycles bind anions in the solid state. That discovery led the present inventors to synthesize novel calix[n]pyrroles, calix[m]pyridino[n]pyrroles or calix[m]pyridine macrocycles, to develop new methods of making said macrocycles, and to demonstrate methods of using said macrocycles as presented herein.

"Calix[n]pyrrole," as used herein, means a macrocycle having "n" pyrrole rings linked in the α positions via $sp^3$ hybridized meso-carbon atoms that are not bound to hydrogen (protium), deuterium or tritium atoms. This is a subset of a class of molecules that was previously termed porphyrinogens. "Calix[m]pyridino[n]pyrrole," as used herein, means a macrocycle having "m" pyridine rings and "n" pyrrole rings linked in the α positions via sp³ hybridized meso-carbon atoms that are not bound to hydrogen (protium), deuterium or tritium atoms. "Calix[m]pyridine," as used herein, means a macrocycle having "m" pyridine rings linked in the α positions via sp³ hybridized meso-carbon atoms that are not bound to hydrogen (protium), deuterium or tritium atoms.

A "calix[n]pyrrole", "calix[m]pyridino[n]pyrrole" or "calix[m]pyridine" is different from a porphyrinogen since a porphyrinogen has one or more sp³ hybridized meso-carbon atoms bound to a hydrogen (protium), deuterium or tritium atom. A "calix[n]pyrrole", "calix[m]pyridino[n]pyrrole" or "calix[m]pyridine" is different from a porphomethene since a porphomethene contains three sp³ hybridized meso-carbons and one sp² hybridized meso-carbon. A "calix[n]pyrrole", "calix[m]pyridino[n]pyrrole" or "calix[m]pyridine" is different from a phlorin since a phlorin contains one sp³ hybridized meso-carbon and three sp² hybridized meso-carbons. A "calix[n]pyrrole", "calix[m]pyridino[n]pyrrole" or "calix[m]pyridine" is different from a porphyrin since a porphyrin contains four sp² hybridized meso-carbons and is aromatic. A "calix[n]pyrrole", "calix[m]pyridino[n]pyrrole" or "calix[m]pyridine" is different from an expanded porphyrin since an expanded porphyrin contains at least one sp² hybridized meso-carbon.

Macrocycles of the present invention have unexpected properties that make them particularly useful. Calix[n]pyrroles and calix[m]pyridino[n]pyrroles bind anions and neutral molecular species in solution and in the solid state in such an effective and selective way that the anions or neutral molecular species can be separated from other anions and neutral molecular species. Calix[m]pyridino[n]pyrroles and calix[m]pyridines can also be used to bind and separate cations. Further, the affinity a macrocycle has for a particular species can be "tuned" by strategic choice of electron-donating or electron-withdrawing peripheral substituents for synthesis of the macrocycle. Additionally, the affinity a calix[m]pyridino[n]pyrrole or calix[m]pyridine has for a particular species can be "tuned" by N-protonation or quaternization by N-alkylation. Applications of these properties for removal of biological ions or neutral molecule species for medical uses, or removal of undesirable ions or neutral molecule species from environmental sources provide only a few of the practical and important uses for the present molecules.

A calix[n]pyrrole, calix[m]pyridino[n]pyrrole, or calix[m]pyridine macrocycle noncovalently-complexed to a molecular or ionic species is an embodiment of the present invention. When the macrocycle is a calix[4]pyrrole the ionic species is other than a metal cation. The term "n" refers to the number of pyrrole rings in the calixpyrrole macrocycle and, for molecules of the present invention, is 4, 5, 6, 7, or 8. The term "m+n" refers to the number of pyridine and pyrrole rings in the calixpyridinopyrrole macrocycle respectively and, for molecules of the present invention, is 4, 5, 6, 7, or 8. The term "m" refers to the number of pyridine rings in the calixpyridine macrocycle and, for molecules of the present invention, is 4, 5, 6, 7, or 8. "Noncovalently-complexed to a molecular or anionic species," as used herein, means that bound molecules are held to the core of a macrocycle by noncovalent binding to one or more pyrrolic N—H or pyridino N—H⁺ groups thus forming a supramolecular ensemble. "Noncovalent binding" includes intermolecular interactions such as hydrogen bonds, dipole-dipole interactions, dipole-induced dipole interactions, ion-dipole interactions, ion pairing, van der Waals interactions, London dispersion forces, π-π stacking interactions, edge-to-face π-interactions, cation-π interactions, charge transfer interactions, or entropic, hydrophobic or solvophobic effects. In a preferred embodiment of the invention, the ionic species is an anionic species.

"Supramolecular" as used herein describes the chemistry of complexes, that is molecular ensembles containing more than one atomic, ionic, or molecular component. Thus complexes of the macrocycles of the present invention and an ion or neutral molecule are considered to be supramolecular complexes or ensembles.

A calix[n]pyrrole, calix[m]pyridino[n]pyrrole or calix[m]pyridine macrocycle attached to a solid support, where m, m+n and n are defined as herein above, is a particularly useful embodiment of the present invention. Due to the effective and selective separation of a variety of molecules by calix[n]pyrrole-derivatized solid supports as described in the examples herein, the present inventors have developed a new type of liquid phase chromatography termed "Hydrogen-Bonding Liquid Chromatography." The bases of the chromatography are noncovalent interactions, primarily hydrogen bonding.

A calix[n]pyrrole, calix[m]pyridino[n]pyrrole or calix[m]pyridine macrocycle having a first conformation in a solid state when unbound to a molecular or anionic species and having a second conformation in a solid state when bound to a molecular or anionic species where n is 4, 5, 6, 7, or 8 is another embodiment of the present invention. In particular, the present inventors have observed an unbound 1,3-alternate "first" conformation, and a bound cone or 1,2-alternate "second" conformation for calix[4]pyrrole macrocycles.

Exemplary calix[n]pyrrole macrocycles for anion and neutral molecular species binding, for solid supports, for derivatives, for multimers, for conjugates and the like, have structure I.

I

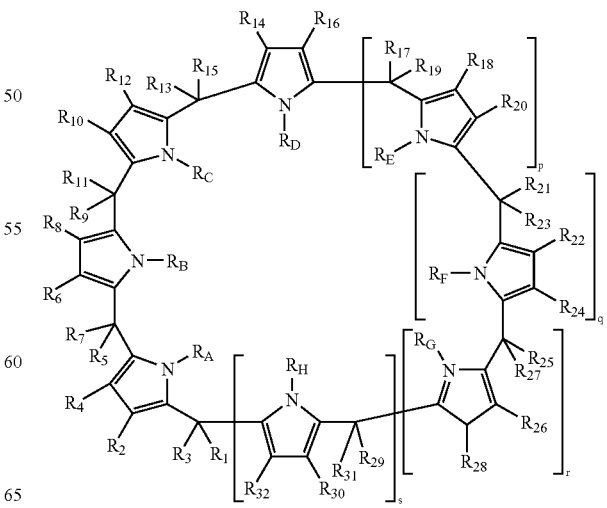

For structure I, when n is 4, p=q=r=s=0, $R_1$–$R_{16}$ are independently substituents as listed in paragraph i) below, and $R_A$–$R_D$ are independently substituents as listed in paragraph ii) below. When n is 5, p=1, q=r=s=0, $R_1$ to $R_{20}$ are independently substituents as listed in paragraph i) below, and $R_A$–$R_E$ are independently substituents as listed in paragraph ii) below. When n is 6, p=q=1, r=s=0, $R_1$ to $R_{24}$ are independently substituents as listed in paragraph i) below, and $R_A$–$R_F$ are independently substituents as listed in paragraph ii) below. When n is 7, p=q=r=1, s=0, $R_1$ to $R_{28}$ are independently substituents as listed in paragraph i) below, and $R_A$–$R_G$ are independently substituents as listed in paragraph ii) below. When n is 8, p=q=r=s=1, $R_1$ to $R_{32}$ are independently substituents as listed in paragraph i) below, and $R_A$–$R_H$ are independently substituents as listed in paragraph ii) below;

i) hydrogen, halide, hydroxyl, alkyl, alkenyl, alkynyl, aryl, alkylaryl, nitro, phospho, formyl, acyl, hydroxyalkyl, alkoxy, hydroxyalkoxy, hydroxyalkenyl, hydroxyalkynyl, saccharide, carboxy, carboxyalkyl, carboxyamide, carboxyamidealkyl, amino, amido, aminoalkyl, phosphoalkyl, alkyl sulfoxide, alkyl sulfone, alkyl sulfide, tetrahydropyran, tetrahydrothiapyran, thioalkyl, haloalkyl, haloalkenyl, haloalkynyl, alkyl ester, a site-directing molecule, a catalytic group, a reporter group, a binding agent, or a couple that is coupled to a site-directing molecule, to a catalytic group, to a reporter group, or to a binding agent;
  ii) hydrogen, alkyl, aminoalkyl, carboxy alkyl, carboxyamide alkyl, phospho alkyl, alkyl sulfoxide, alkyl sulfone, alkyl sulfide, halo alkyl, aryl, N-oxide, dialkylamino, carbamate, or arylsulfonyl.

Alternatively, at least two substituents attached to a pyrrole β-carbon, a meso-carbon or a pyrrole nitrogen are coupled to form a bridged structure, and when coupled to form a bridged structure, nonbridged substituents are as defined herein in paragraph i) or ii). Odd-numbered R-substituents are other than hydrogen for macrocycles having structure I.

A meso-substituted calix[n]pyrrole, where n is 4, 5, 6, 7, or 8, and where the meso-substitution is an oxygen-, sulfur-, or alkenyl-containing substituent is an embodiment of the present invention. Oxygen-, or sulfur-containing substituents are particularly useful for giving the macrocycle a functionality that can be further derivatized for uses described herein. A "monohook" calix[n]pyrrole having an oxygen-containing carboxyl group has been found to possess self-assembly properties as shown in FIG. 4. A calix[n]pyrrole having a vinyl substituent as an example of an alkenyl group is particularly useful for forming a polymer of defined linkage and structure. Such a polymer is useful for a selective electrode as described herein.

A further aspect of the present invention is a β-substituted calix[n]pyrrole. Exemplary β-substituted calix[n]pyrrole macrocycles have structure I as described herein wherein at least one even-numbered R substituent is other than hydrogen. Substitution on a β-carbon of a pyrrole ring provides even further flexibility in the design of macrocycles of the present invention for the various uses described herein.

A calix[m]pyridino[n]pyrrole macrocycle having structure II is a further aspect of the present invention.

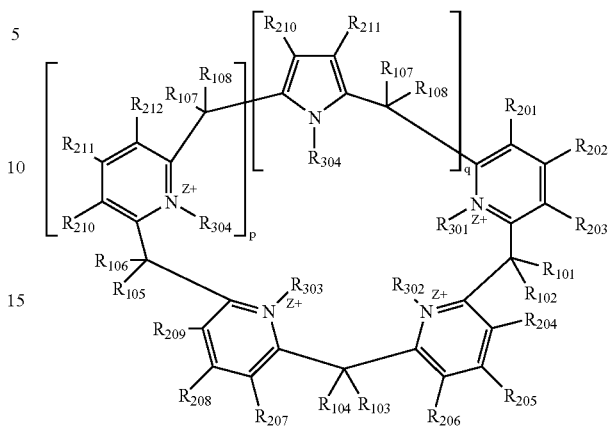

II

The term "m" designates a number of pyridines, and the term "n" designates a number of pyrroles, in macrocycle II, m+n=4, and m is other than 1 or 2. When m is 4; n=0, p=1, and q=0, $R_{101}$ to $R_{108}$ and $R_{201}$ to $R_{212}$ are independently substituents as listed in paragraph i) above, and $R_{301}$–$R_{304}$ are independently substituents as listed in paragraph ii) above. When m is 3; n=1, p=0, q=1, $R_{101}$ to $R_{108}$ and $R_{201}$ to $R_{211}$ are independently substituents as listed in paragraph i) above, and $R_{301}$–$R_{304}$ are independently substituents as listed in paragraph ii) above. $R_{201}$–$R_{208}$ are other than hydrogen. When $R_{301}$–$R_{304}$ is other than a lone pair of electrons, Z=1, that is, the pyridine nitrogen atom is positively charged. When $R_{301}$–$R_{304}$ is a lone pair of electrons Z=0, that is, the pyridine nitrogen atom is neutral.

Further aspects of the present invention include calix[m]pyridino[n]pyrrole macrocycles where m and n designate a number of pyridines and pyrroles in the macrocycle, respectively, m and n are other than 0, and m+n=5, 6, 7, or 8. Each pyridine or pyrrole α-carbon is bound to another pyridine or pyrrole α-carbon via one non hydrogen-linked $sp^3$-hybridized meso-carbon; each $sp^3$ hybridized meso-carbon is further independently bonded to a group characterized in paragraph i) above with the exception of hydrogen; each pyridine β carbon, pyrrole β carbon and pyridine γ carbon is independently bonded to a group characterized in paragraph i) above; each pyridine or pyrrole nitrogen is bound to a group characterized in paragraph ii) above. In a further embodiment, at least one $sp^3$ meso-carbon, pyridine β-carbon, pyrrole β-carbon, pyridine γ-carbon, pyrrole nitrogen, or pyridine nitrogen is coupled to form a bridged structure to itself or to another $sp^3$ hybridized meso-carbon, pyridine β-carbon, pyrrole β-carbon, pyridine γ carbon, pyrrole nitrogen, or pyridine nitrogen; and when coupled to form a bridged structure, non-bridged atoms are as defined for an $sp^3$ hybridized meso-carbon, pyridine β-carbon, pyrrole β-carbon, pyridine γ carbon, pyrrole nitrogen, or pyridine nitrogen.

A calix[m]pyridine macrocycle having structure III wherein m is 4, 5. 6, 7, or 8 is a further aspect of the present invention.

III

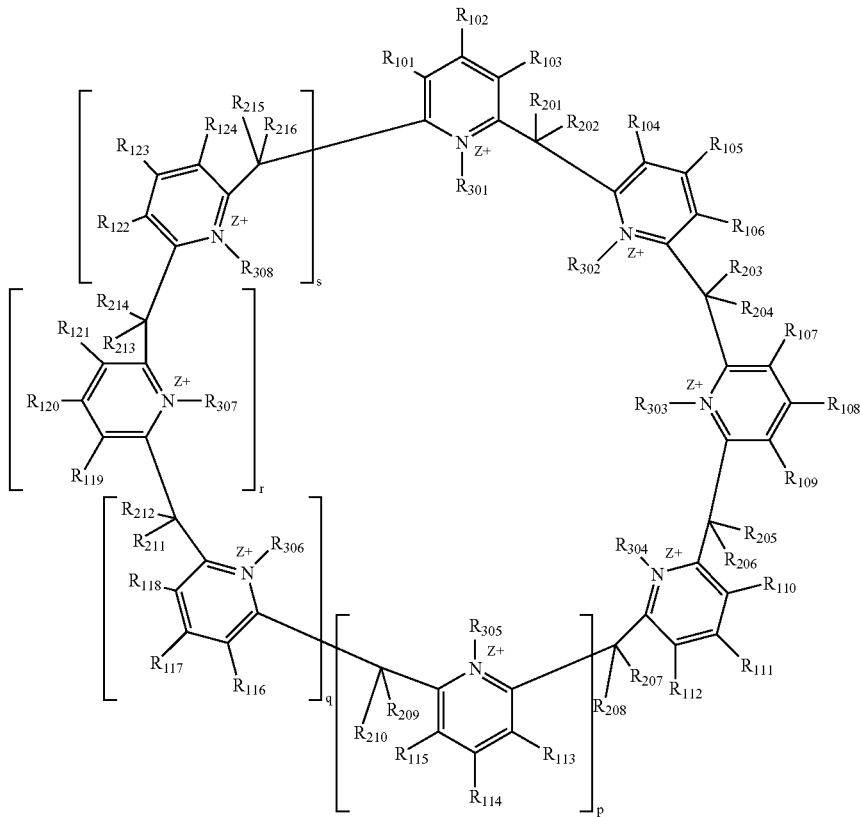

When m is 4, p=q=r=s=0, $R_{101}$ to $R_{112}$ and $R_{201}$ to $R_{208}$ are independently substituents as listed in paragraph i) below, and $R_{301}$–$R_{304}$ are independently substituents as listed in paragraph ii) above. When m is 5, p=1, q=r=s=0, $R_{101}$ to $R_{115}$ and $R_{201}$ to $R_{210}$ are independently substituents as listed in paragraph i) above, and $R_{301}$–$R_{305}$ are independently substituents as listed in paragraph ii) above. When m is 6, p=q=1, r=s=0, $R_{101}$ to $R_{118}$ and $R_{201}$ to $R_{212}$ are independently substituents as listed in paragraph i) above, and $R_{301}$–$R_{306}$ are independently substituents as listed in paragraph ii) above. When m is 7, p=q=r=1, s=0, $R_{101}$ to $R_{121}$ and $R_{201}$ to $R_{214}$ are independently substituents as listed in paragraph i) above, and $R_{301}$–$R_{307}$ are independently substituents as listed in paragraph ii) above. When m is 8, p=q=r=s=1, $R_{101}$ to $R_{124}$ and $R_{201}$ to $R_{216}$ are independently substituents as listed in paragraph i) above, and $R_{301}$–$R_{308}$ are independently substituents as listed in paragraph ii) above. $R_{201}$–$R_{216}$ are other than hydrogen. When $R_{301}$–$R_{30m}$ are other than a lone pair of electrons. Z=1, that is the pyridine nitrogen atom carries a positive charge. When $R_{301}$–$R_{30m}$ are a lone pair of electrons Z=0, that is the pyridine nitrogen atom is neutral. In a further embodiment at least two substituents are coupled to form a bridged structure, and when coupled to form a bridged structure, nonbridged substituents are as defined in paragraph i) or ii) above.

A calix[n]pyrrole where n is 5, 6, 7, or 8 is another embodiment of the present invention. Calix[n]pyrroles having a number of pyrrole rings greater than four have not been previously known. An advantage of the larger macrocycles over those having four pyrroles is that they are expected to show enhanced binding properties with large- or poly-anions and have the property of binding more than one anion simultaneously.

A chiral calix[n]pyrrole, calix[m]pyridino[n]pyrrole, or calix[m]pyridine where m and n are defined herein above, is a further embodiment of the present invention. A chiral calixpyrrole, calixpyridinopyrrole or calixpyridine is expected to have different binding properties for each of a pair of enantiomeric species, thus allowing preferential binding of a particular enantiomer.

The present invention provides a number of different novel methods of making calix[n]pyrrole, calix[m]pyridino[n]pyrrole, and calix[m]pyridine macrocycles. A first method of making embodiment is a method of making a calix[n]pyrrole where n is 4, 5, 6, 7, or 8, the calix[n]pyrrole having an ester substituent, comprising reacting an ester-functionalized ketone, pyrrole and a ketone to produce a calix[n]pyrrole having an ester substituent.

A second method of making embodiment is a method of making a calix[n]pyrrole where n is 4, 5, 6, 7, or 8, the calix[n]pyrrole having an acid substituent, comprising reacting an ester-functionalized ketone, pyrrole and a ketone to produce a calix[n]pyrrole ester derivative; and de-esterifying the ester derivative to produce a calix[n]pyrrole monoacid derivative.

A method of making a β-substituted calix[n]pyrrole where n is 4, 5, 6, 7, or 8 comprising activating a calix[n]pyrrole where n is 4, 5, 6, 7, or 8; and reacting the activated calix[n]pyrrole with an electrophile is a third method of making embodiment of the invention.

A fourth synthetic method embodiment of the invention is a method of making a β-substituted calix[n]pyrrole where n is 4, 5, 6; 7, or 8 comprising reacting a β-substituted pyrrole and a ketone to produce a β-substituted calix[n]pyrrole.

A method of making a β-substituted calix[n]pyrrole where n is 4, 5, 6, 7, or 8 comprising producing a calix[n]pyrrole radical where n is 4, 5, 6, 7, or 8; and reacting the radical with a radical acceptor molecule is a fifth synthetic method embodiment of the invention.

A method of making a calix[n]pyrrole wherein n is 5, 6, 7, or 8 comprising reacting a pyrrole and a ketone in the presence of a Lewis acid is a sixth synthetic method embodiment of the invention.

A seventh method of making embodiment is a method of making a calix[n]pyrrole wherein n is 4, 5, 6, 7, or 8 comprising reacting a pyrrole and a ketone in the presence of a heterogenous catalyst.

An eighth synthetic method embodiment of the invention is a method of making a calix[n]pyrrole wherein n is 4, 5, 6, 7, or 8 comprising the steps of a) reacting a ketone-functionalized pyrrole and an alkyl metal to form a pyrrole alcohol, b) condensing the pyrrole alcohol to form a cyclizable pyrrole oligomer, and c) repeating step b) at least n minus 2 times to form a calix[n]pyrrole.

A ninth synthetic method embodiment of the invention is a method of making a calix[n]pyrrole wherein n is 4, 5, 6, 7, or 8 comprising reacting a pyrrole and a ketone in the presence of an anion template.

A method of making a solid-supported calix[n]pyrrole, solid-supported calix[m]pyridino[n]pyrrole, or solid-supported calix[m]pyridine comprising attaching a calix[n]pyrrole, a calix[m]pyridino[n]pyrrole, or a calix[m]pyridine having a functionalized group to a solid support, the solid support reactive with the functionalized group, or to a tether-functionalized solid support, the tether reactive with the functionalized group is a tenth synthetic method embodiment of the present invention.

A method of making a calixpyridinopyrrole comprising adding halocarbene to a calixpyrrole in a cycloaddition reaction, thereby converting a pyrrole to a pyridine and forming a calixpyridinopyrrole is an eleventh synthetic embodiment of the present invention. Preferably, the halocarbene is chlorocarbene and most preferably, is dichlorocarbene.

A method of making a calixpyridine comprising: adding halocarbene to calixpyrrole or to calixpyridinopyrrole in a cycloaddition reaction so as to convert pyrrole to pyridine to form a calixpyridine is a twelth synthetic method embodiment of the present invention. The halocarbene is as described herein.

A thirteenth method of making embodiment or synthesis embodiment is a method of making a calix[n]pyrrole where n is 5, 6, 7, or 8, the calix[n]pyrrole having different substituents at meso-carbon atoms, comprising reacting pyrrole and at least two ketone molecules to produce a calix[n]pyrrole having different substitutents at meso-carbon atoms.

A method of making a calix[n]pyrrole comprising reacting a cyclic ketone template having n ketone groups and pyrrole or β-substituted pyrrole to produce a calix[n]pyrrole is a fourteenth method of making embodiment of the invention.

A further composition of matter of the present invention is a calix[n]pyrrole, a calix[m]pyridino[n]pyrrole, or a calix[m]pyridine made by one of the first through fourteenth synthetic method embodiments provided herein.

A method of forming a complex of a calix[n]pyrrole or a calix[m]pyridino[n]pyrrole, and an ion or a neutral molecule comprising contacting the calix[n]pyrrole or the calix[m]pyridino[n]pyrrole with the ion or neutral molecule under conditions effective to allow the formation of the complex is a further aspect of the invention.

Another aspect of the invention is a method for separating a first molecule, a first anion or a first cation from a mixture of a first molecule, a first anion or a first cation and other species, comprising obtaining a calix[n]pyrrole-, a calix[m]pyridino[n]pyrrole- or a calix[m]pyridine-derivatized solid support; and contacting the solid support with the mixture to separate the first molecule, the first anion or the first cation. Another method of separating includes batch processing where a macrocycle or macrocycle of the present invention attached to a solid support is added to a mixture containing the ion or molecule to be separated, and separating the macrocycle-molecule, macrocycle-ion, solid support-macrocycle-ion or solid support-macrocycle-molecule complex. Macrocycles provided herein are particularly effective as separation media as described in the present examples.

A method of transporting a molecular or ionic species through a membrane comprising incorporating a calix[n]pyrrole or a calix[m]pyridino[n]pyrrole into the membrane; and contacting the membrane with the molecular or ionic species in the presence of a gradient of the molecular or ionic species or counter gradient of another back-transported species is an embodiment of the invention. Thus, the present invention maybe used to facilitate the transport of ionic or neutral substrates in both a synport or antiport sense.

A further embodiment of the present invention is an electropolymerizable calix[n]pyrrole, calix[m]pyridino[n]pyrrole, or calix[m]pyridine, which macrocycles, are useful for constituting modified electrodes for the detection of ionic or molecular species.

A further embodiment of the present invention is an anion-, cation-, or neutral molecule-selective electrode comprising a conductive body, a polymer, and a calix[n]pyrrole, a calix[m]pyridino[n]pyrrole, or a calix[m]pyridine. The calix[n]pyrrole, the calix[m]pyridino[n]pyrrole, or the calix[m]pyridine may be electropolymerized and form the conductive body.

A method of electrochemical detection of an anion, a cation, or a neutral molecule comprising assembling an anion-, cation-, or neutral molecule-selective electrode and contacting the electrode with a solution of the anion, the cation, or the neutral molecule, and detecting the presence or absence of the anion, the cation, or the neutral molecule is an embodiment of the present invention.

A method of binding a cation comprising contacting the cation with a calix[n]pyrrole or calix[m]pyridino[n]pyrrole having a cation-binding functionality, or with a calix[m]pyridine is also an aspect of the invention.

A method of removal of pertechnetate from pertechnetate-containing nuclear waste comprising contacting the waste with a calix[n]pyrrole or a calix[m]pyridino[n]pyrrole to form a calix[n]pyrrole- or a calix[m]pyridino[n]pyrrole-pertechnetate complex; and removing the complex from the waste is also an aspect of this invention.

A method of removal of an environmental pollutant from an environmental source, comprising contacting the environmental source with a calix[n]pyrrole or a calix[m]pyridino[n]pyrrole to form a calix[n]pyrrole- or a calix[m]pyridino[n]pyrrole-pollutant complex, and removing the complex from the environmental source is also an aspect of this invention.

Further embodiments of the invention include a chromatography column or a sensor comprising a solid support bound to a calix[n]pyrrole where n is 4–8, to a calix[m]pyridino[n]pyrrole where m–n=4–8 and m is not 1 or 2, or to a calix[m]pyridine where m is 4–8. Use of a calix[n]pyrrole, a calix[m]pyridino[n]pyrrole, or a calix[m]pyridine in the preparation of a pharmaceutical composition for use in in vivo or ex vivo treatment of body tissues is another embodiment of the invention. The treatment may involve binding, transport, and/or removal of ions or neutral molecular species for conditions such as gout, for kidney dialysis, for removal of viruses, for introduction of antiviral drugs, or the like. A method, therefore, includes administering to a patient in need thereof a therapeutically effective amount of a calix[n]pyrrole, a calix[m]pyridino[n]pyrrole, or a calix[m]pyridine.

BRIEF DESCRIPTION OF THE DRAWINGS

The following drawings form part of the present specification and are included to further demonstate certain aspects of the present invention. The invention may be better understood by reference to one or more of these drawings in combination with the detailed description of the specific embodiments presented herein.

DETAILED DESCRIPTION OF THE PREFERRED EMBODIMENTS

Figure 1A:
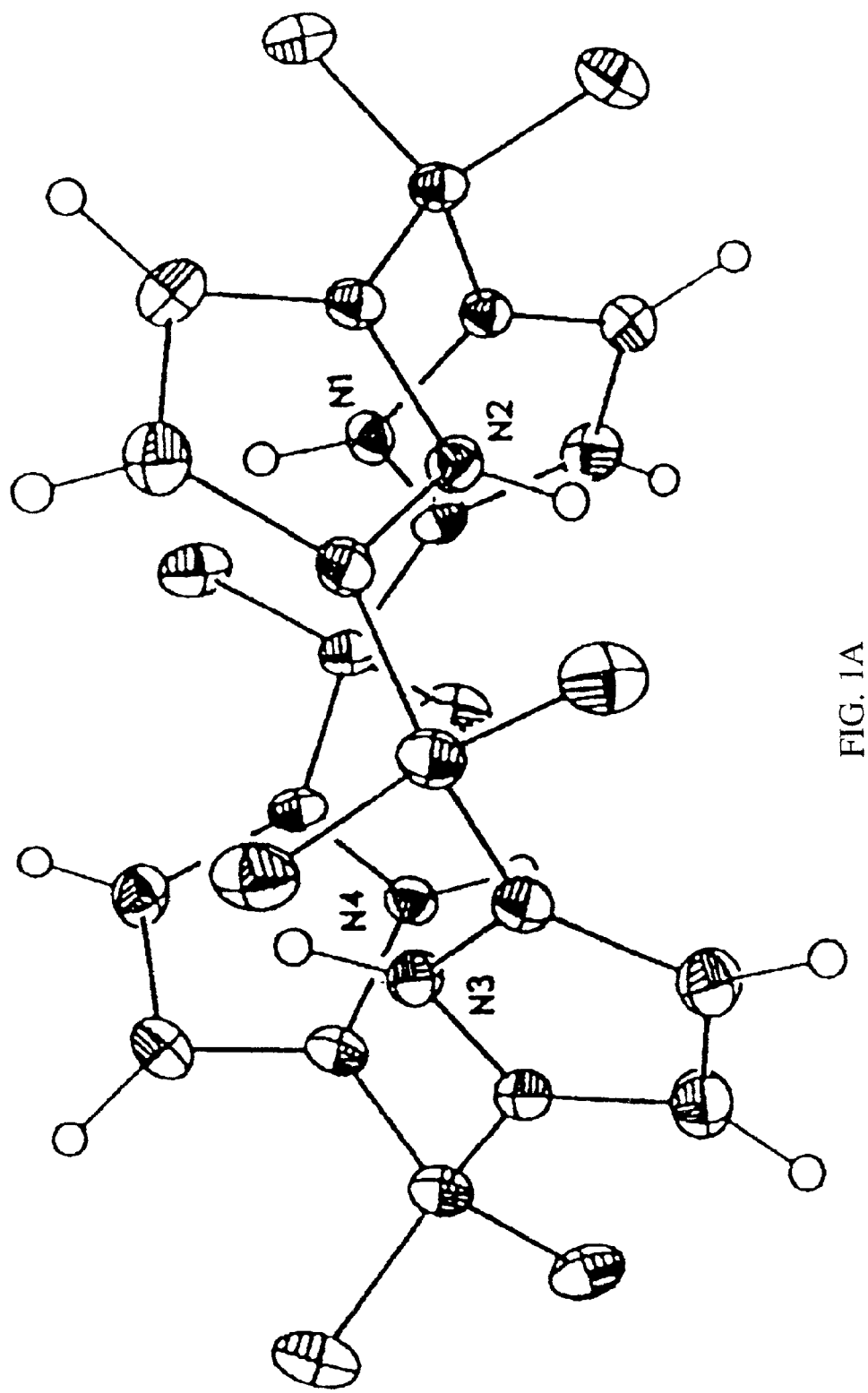
FIG. 1A illustrates the X-ray crystal structure of meso-octamethylcalix[4]pyrrole, 1, adopting a 1,3-alternate conformation. Thermal ellipsoids are at 30% probability level.

The present invention provides β-substitued calix[n]pyrroles, calix[m]pyridines, calix[n]pyrrole-anion complexes, calix[m]pyridino[n]pyrrole-anion complexes, calix[n]pyrrole-neutral molecule complexes, calix[m]pyridino[n]pyrrole-neutral molecule complex, calix[m]pyridino[n]pyrrole-cation complexes, calix[m]pyridine-cation complexes, calix[m]pyridine-neutral molecule complexes and certain meso-substituted calix[4]pyrroles, meso-substituted calix[n]pyrroles where n is 5, 6, 7, or 8, certain calix[m]pyridino[n]pyrroles, where m+n=4, and calix[m]pyridino[n]pyrroles where m+n=5, 6, 7, or 8 as new compositions of matter.

Specific anions bound by macrocycles of the present invention include, but are not limited to, halide anions, carboxylates, phosphates, sulfates, oxalates, terephthalates, phospholipids, nucleotides, oligonucleotides, DNA, RNA, anionic polyoxometalates, or oxoanions such as pertechnetate as demonstrated in the examples herein, size and charge of the anion appear not to be limiting factors in the type of anion that may be bound since oligonucleotides are able to be separated on calix[4]pyrrole modified HPLC columns.

The term "molecular species" as used herein, means a neutral molecule, and represents a variety of classes of molecules since the macrocycles of the present invention provide different sizes of cavities and varieties of donor and acceptor sites. Specific neutral molecules include, but are not limited to, alcohols, polyalcohols, ketones, polyketones, phenols, polyhydroxylated aliphatic and aromatic compounds, amino compounds, amino acids, urea, guanidine, saccharides, biologically important polymers like proteins derivatives, and the like. Additionally, neutral molecules include, but are not limited to, ion pairs such as NaCl, CsI, or any grouping of ions which is neutral overall, or zwitterionic species such as amino acids and the like.

Specific cations include, but are not limited to, Group 1 metals, Group 2 metals, transition metals, post-transition metals, lanthanides, actinides, ammonium, alkylammonium, arylammonium, hydroxonium and guanaidinium.

Carbon atoms in pyrrole rings are referred to as α or β; α carbons are adjacent to the NH group and β-carbons are adjacent to the α-carbons (see IV). In an alternative designation, the nitrogen atom is labelled 1 and the other atoms are numbered sequentially starting from an adjacent carbon atom. Thus, the α-carbons are also referred to as atoms 2 and 5 and the β-carbons as atoms 3 and 4.

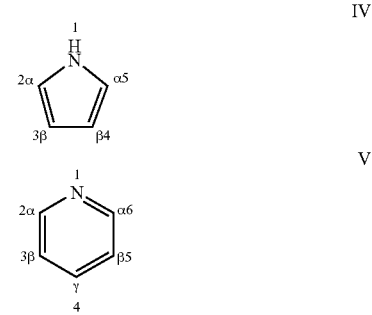

Similarly, carbon atoms in pyridine rings are referred to as α,β or γ; α carbons are adjacent to the N atom, β-carbons are adjacent to the α-carbons and the γ-carbon is adjacent to the two β-carbons (see V). In an alternative designation, the nitrogen atom is labelled 1 and the other atoms are numbered sequentially starting from an adjacent carbon atom. Thus, α-carbons are also referred to as atoms 2 and 6, β-carbons as atoms 3 and 5, and the γ-carbon as atom 4.

As used herein, "a non-α, non-meso, macrocyclic carbon" means a β or a γ carbon; and "macrocyclic nitrogen" means a pyrrole or pyridine nitrogen.

Substituents for Macrocycles of the Present Invention

Representative examples of alkanes useful as alkyl group substituents of the present invention include straight-chain, branched or cyclic isomers of propane, butane, pentane, hexane, heptane, octane, nonane, and decane, with methane, ethane, propane, and cyclohexane being preferred. Alkyl groups having up to about thirty, or up to about fifty carbon atoms are contemplated in the present invention. Representative examples of substituted alkyls include alkyls substituted by two or more functional groups as described herein.

Representative examples of alkenes useful as alkenyl group substituents include ethene, straight-chain, branched or cyclic isomers of propene, butene, pentene, hexene, heptene, octene, nonene, and decene, with ethene and propene being preferred. Alkenyl groups having up to about thirty or fifty carbon atoms, and up to about five double bonds, or more preferably, up to about three double bonds are contemplated in the present invention.

Representative examples of alkynes useful as alkynyl group substituents include ethyne, straight-chain, branched or cyclic isomers of propyne, butyne, pentyne, hexyne, heptyne, octyne, nonyne, and decyne, with ethyne and propyne being preferred. Alkynyl groups having up to about thirty, or up to about fifty carbon atoms, and having up to about five or up to about three triple bonds are contemplated in the present invention.

The aryl may be a compound whose molecules have the ring structure characteristic of benzene, naphthalene, phenanthrene, anthracene, and the like, i.e., either the 6-carbon ring of benzene or the condensed 6-carbon rings of the other aromatic derivatives, or a compound whose molecules have the ring structure characteristic of pyridine i.e., a 5-carbon-1-heteroatom ring, or pyrrole i.e., 4-carbon-1-heteroatom ring such as, but not limited to, pyrrole, furan, or thiophene or the condensed 5-or 6-atom rings of the other aromatic derivatives. For example, an aryl group may be phenyl or naphthyl, and the terms used herein include both unsubstituted aryls and aryls substituted with one or more nitro, carboxy, sulfonic acid, hydroxy, oxyalkyl or halide substituent. Purine or pyrimidine molecules are included as "aryl" molecules. In this case, the substituent on the phenyl or naphthyl may be added in a synthetic step after the condensation step which forms the macrocycle.

Among the halide substituents, chloride, bromide, fluoride and iodide are contemplated in the practice of this invention. Representative examples of haloalkyls used in this invention include halides of methane, ethane, propane, butane, pentane, hexane, heptane, octane, nonane and decane, with halides, preferably chlorides or bromides, of methane, ethane and propane being preferred. Representative examples of haloalkenyls used in this invention include halides of methene, ethene, propene, butene, pentene, hexene, heptene, octene, nonene and decene, with halides, preferably chlorides or bromides, of methene, ethene and propene being preferred. Representative examples of haloalkynyls used in this invention include halides of methyne, ethyne, propyne, butyne, pentyne, hexyne, heptyne, octyne, nonyne and decyne, with halides, preferably chlorides or bromides, of methyne, ethyne and propyne being preferred.

"Hydroxyalkyl" means alcohols of alkyl groups. Preferred are hydroxyalkyl groups having one to twenty, more preferably one to ten, hydroxyls. "Hydroxyalkyl" is meant to include glycols and polyglycols; diols of alkyls, with diols of C1–10 alkyls being preferred, and diols of C1–3 alkyls being more preferred; and polyethylene glycol, polypropylene glycol and polybutylene glycol as well as polyalkylene glycols containing combinations of ethylene, propylene and butylene.

Representative examples of alkoxys include the alkyl groups as herein described having ether linkages. "Alkoxy" is meant to include polyethers with one or more functional groups. The number of repeating alkoxys within a substituent may be up to 200, preferably is from 1–20, and more preferably, is 1–10, and most preferably is 1–5. A preferred alkoxy is $O(CH_2CH_2O)_xCH_3$ where x=1–100, preferably 1–10, and more preferably, 1–5.

"Crown ether" means a cyclic polyether with repeating alkoxy groups. They are named according to the number of atoms and the number of oxygens in the cycle. S-crown-T is a cyclic polyether containing S atoms and T oxygen atoms. Preferred are crown ethers containing one to twenty oxygen atoms, more preferably one to ten. Representative examples include, but are not limited to, 12-crown-4, 15-crown-5, benzo-15-crown-5, 18-crown-6, benzo-18-crown-6, 21-crown-7,24-crown-8, dibenzo-18-crown-6 and functionalized derivatives thereof.

"Hydroxyalkenyl" means alcohols of alkene groups. Preferred are hydroxyalkenyl groups having one to twenty, more preferably one to ten, hydroxyls.

"Hydroxyalkynyl" means alcohols of alkyne groups. Preferred are hydroxyalkenyl groups having one to twenty, more preferably one to ten, hydroxyls.

"Hydroxyalkoxy" means alkyl groups having ether or ester linkages, hydroxyl groups, substituted hydroxyl groups, carboxyl groups, substituted carboxyl groups or the like.

Representative examples of thioalkyls include thiols of ethane, thiols of straight-chain, branched or cyclic isomers of propane, butane, pentane, hexane, heptane, octane, nonane and decane, with thiols of ethane (ethanethiol, $C_2H_5SH$) or propane (propanethiol, $C_3H_7SH$) being preferred. Sulfate-substituted alkyls include alkyls as described above substituted by one or more sulfate groups, a representative example of which is diethyl sulfate $((C_2H_5)_2SO_4)$.

"Alkylsulfoxide" means alkyl groups having S=O groups. Preferred are alkylsulfoxide groups having one to twenty, more preferably one to ten, sulfoxides. Alkylsulfoxide is meant to include cyclic alkyl groups containing sulfoxide moieties.

"Alkylsulfone" means alkyl groups having $S(=O)_2$ groups. Preferred are alkylsulfone groups having one to twenty, more preferably one to ten, sulfones. Alkylsulfone is meant to include cyclic alkyl groups containing sulfone moieties.

"Alkylsulfide" means alkyl groups having S groups. Preferred are alkylsulfide groups having one to twenty, more preferably one to ten, sulfides. Alkylsulfide is meant to include cyclic alkyl groups containing sulfide moieties such as tetrahydrothiopyran derivatives.

Representative examples of phosphates include phosphate groups, polyphosphate groups, DNA, RNA, oligonucleotides and nucleotides. Representative examples of phosphate-substituted alkyls include alkyls as described above substituted by one or more phosphate or polyphosphate groups. Representative examples of phosphonate-substituted alkyls include alkyls as described above substituted by one or more phosphonate groups.

Representative examples of carboxy groups include carboxylic acids of the alkyls described above as well as aryl carboxylic acids such as benzoic acid and derivatives thereof. Representative examples of carboxyamides include peptides, proteins, primary carboxyamides ($CONH_2$), secondary ($CONHR'$) and tertiary ($CONR'R''$) carboxyamides where each of R' and R'' is a functional group as described herein.

Representative examples of useful amines include a primary, secondary or tertiary amine of an alkyl or aryl as described herein.

"Carboxyamidealkyl" means alkyl groups with secondary or tertiary amide linkages or the like. "Carboxyalkyl" means alkyl groups having hydroxyl groups, carboxyl or amide substituted ethers, ester linkages, tertiary amide linkages removed from the ether or the like.

The term "saccharide" includes oxidized, reduced or substituted saccharide; hexoses such as D- or L-glucose, D- or L-mannose or D- or L-galactose; pentoses such as D- or L-ribose or D- or L-arabinose: ketoses such as D- or L-ribulose or D- or L-fructose; disaccharides such as sucrose, lactose, or maltose; derivatives such as acetals, amines, and phosphorylated sugars; oligosaccharides or polysaccharides, such as aliginic acid as well as open chain forms of various sugars, and the like. Examples of amine-derivatized sugars are galactosamine, glucosamine, sialic acid and D- and L-glucamine derivatives such as 1-amino-1-deoxysorbitol.

By "reporter group" is meant a substituent that is fluorescent, chromophoric, electropolymerizable, redox-active, or optically active. Examples of a fluorescent reporter group include, but are not limited to, ruthenium (II) bipyridyl complexes, acetylnaphthalene, 9-aminoacridine, 9-phenylanthracene, benzimidazole, N-methylbenzo[b]carbazole, 2-phenylbenzoxazole, 1,1'-binaphthyl, fluorene, fluorescein dianion, indeno[2,1-a]indene, 2,5-diphenylfuran, perylene, 2-aminopurine, p-quatephenyl, 4,4'-diphenylstilbene, sapphyrins and texaphyrins. Examples of a chromophoric reporter groups include isosulfan blue, fluoroscein, 2',7'-dichlorofluoroscein, rhodamine, carboxyrhodamine, dialkylaminocoumarin, erythrosin, pyrene, 9-(diethylamino)-5-octadecanoylimino-5H-benzo[a]phenoxazine, 5-octadecanoyloxy-2-(4-nitrophenylazo)phenol, 9-(diethylamino)-5-(2-naphtoylimino)-5H-benzo [a]phenoxazine, 4',5'-dibromoflurescein octadecyl ester, 2-(4-nitrophenylazo)chromotropic acid disodium salt, 2-(phenylazo)chromotropic acid disodium salt, 4,5-dihydroxynaphtalene-2,7-disulfonic acid disodium salt, 5,7-dihydroxyflavone, 5,7-dinitro-8-hydroxy-2-naphthalenesulphonic acid, 6,6'-[(3,3'-dimethyl[1,1'-biphenyl]4,4'-diyl)bis(azo)]bis[4-amino-5-hydroxy-1,3-naphthalenedisulfonic acid] tetrasodium salt, 4,5,6,7,-tetrachloro-3',6'-dihydroxy-2',4',5',7'-tetraiodospiro [isobenzofuran-1(3H),9'-[9H]xanthen]-3-one dipotassium salt, 3,7-bis(dimethylamino)phenothiazin-5-ium chloride, 3,6-bis(dimethylamino)acridine hydrochloride zinc chloride double salt (Acridine Orange), sapphyrins and texaphyrins. By "electropolymerizable" is meant a moiety that will polymerize when subjected to a particular voltammetric potential or a continuous scanning potential. Examples of an electropolymerizable group include, but are not limited to, α-free pyrroles, α-free thiophenes, anilines or vinyl groups.

By "redox-active" is meant a moiety which can undergo an oxidation or a reduction process. Examples of a redox-active group include, but are not limited to, ferrocene, cobaltocenium, ruthenium (II) bipyridyl complexes, transition metals, fullerenes, porphyrins, expanded porphyrins and pyrroles.

In one embodiment of the present invention, a calix[n]pyrrole, calix[m]pyridino[n]pyrrole or calix[m]pyridine is further coupled to a site-directing molecule. "Site-directing" means having specificity for targeted sites. "Specificity for targeted sites" means that upon contacting the calix[n]pyrrole-, calix[m]pyridino[n]pyrrole- or calix[m]pyridine-conjugate with the targeted site, for example, under physiological conditions of ionic strength, temperature, pH and the like, specific binding will occur. The interaction may occur due to specific electrostatic, hydrophobic, or other interaction of certain residues of the conjugate with specific residues of the target to form a stable complex under conditions effective to promote the interaction.

Exemplar site-directing molecules contemplated in the present invention include but are not limited to: polydeoxyribonucleotides; polyribonucleotides; oligodeoxyribonucleotides; oligoribonucleotides; polyamides, including peptides having affinity for a biological receptor, and proteins such as antibodies; steroids and steroid derivatives; hormones such as estradiol, or histamine; hormone mimics such as morphine; and further macrocycles such as texaphyrins, sapphyrins or rubyrins.

Representative examples of useful steroids include a steroid hormone of the following five categories: progestins (e.g. progesterone), glucocorticoids (e.g., cortisol), mineralocorticoids (e.g., aldosterone), androgens (e.g., testosterone) and estrogens (e.g., estradiol).

The term "a peptide having affinity for a biological receptor" means that upon contacting the peptide with the biological receptor, for example, under appropriate conditions of ionic strength, temperature, pH and the like, specific binding will occur. The interaction may occur due to specific electrostatic, hydrophobic, entropic or other interaction of certain amino acid or glycolytic residues of the peptide with specific amino acid or glycolytic residues of the receptor to form a stable complex under the conditions effective to promote the interaction. The interaction may alter the three-dimensional conformation and the function or activity of either or both the peptide and the receptor involved in the interaction. A peptide having affinity for a biological receptor may include an endorphin, an enkephalin, a growth factor, e.g. epidermal growth factor, poly-L-lysine, a hormone, a peptide region of a protein and the like. A hormone may be estradiol, for example.

Representative examples of useful amino acids of peptides or polypeptides include amino acids with simple aliphatic side chains (e.g., glycine, alanine, valine, leucine, and isoleucine), amino acids with aromatic side chains (e.g., phenylalanine, tryptophan, tyrosine, and histidine), amino acids with oxygen-, and sulfur-containing side chains (e.g., serine, threonine, methionine, and cysteine), amino acids with side chains containing carboxylic acid or amide groups (e.g., aspartic acid, glutamic acid, asparagine, and glutamine), and amino acids with side chains containing strongly basic groups (e.g., lysine and arginine), and proline. Representative examples of useful peptides include any naturally occurring or synthetic di-, tri-, tetra-, pentapeptides or longer peptides derived from any of the above described amino acids (e.g., endorphin, enkephalin, epidermal growth factor, poly-L-lysine, or a hormone). Representative examples of useful polypeptides include both naturally occurring and synthetic polypeptides (e.g., insulin, ribonuclease, and endorphins) derived from the above described amino acids and peptides.

The term "binding agent" means that upon contacting the binding agent with a guest species for binding under appropriate conditions of ionic strength, temperature, pH and the like, specific binding will occur. The interaction may alter the three-dimensional conformation and the function or activity of either or both the bound species and the receptor involved in the interaction. Preferred binding agents include a calix[n]pyrrole, a calix[m]pyridino[n]pyrrole, a calix[m]pyridine, a calixarene, a cation-binding functionality, a crown ether, a chelating group, a porphyrin, or an expanded porphyrin such as sapphyrin, rosarin, rubyrin, texaphyrin, amethyrin or turcasarin, or oligopyrroles.

Texaphyrin compounds, methods for making and methods for using them are described in U.S. Pat. Nos. 4,935,498, 5,162,509, 5,252,720, 5,272,142, 5,256,399, 5,292,414, 5,432,171, 5,439,570, 5,475,104, 5,451,576, 5,457,183, 5,369,101, 5,569,759, 5,559,207, 5,587,463, 5,594,136, and 5,599,923; in pending application U.S. Ser. No. 08/484,551; and in PCT publications WO 90/10633, WO 93/14093, WO 94/29316, and WO 96/38461; each patent, application, and publication is incorporated by reference herein.

Rubyrins are disclosed in U.S. Pat. No. 5,410,045, and turcasarins are disclosed in PCT publication WO 96/21665; the patent and PCT publication are incorporated by reference herein.

Sapphyrins are disclosed in U.S. Pat. Nos. 5,041,078; 5,159,065; 5,120,411; 5,302,714; 5,457,195; 5,530,123; 5,543,514; and 5,587,478; each patent is incorporated by reference herein.

A "catalytic group," as used herein, means a chemical functional group that may act as a general acid, Brønsted acid, Lewis acid, general base, Brønsted base, Lewis base, nucleophile, or any other means by which an activation barrier to reaction is lowered or the ground state energy of a substrate is increased. Exemplary catalytic groups contemplated include, but are not limited to, imidazole; guanidine, zinc coordinated to a nitrogen containing macrocycle, EDTA complexes. DTPA compleses, substituted saccharides such as a D-glucosamine, D-mannosamine, D-galactosamine, D-glucamine, and the like; amino acids such as L-histidine and L-arginine: derivatives of amino acids such as histamine; polymers of amino acids such as poly-L-lysine. (LysAla)$_n$, (LysLeuAla)$_n$ where n is from 1–30 or preferably 1–10 or more preferably 2–7 and the like. The catalytic group may be attached either directly to the calix[n]pyrrole, calix[m]pyridino[n]pyrrole or calix[m]pyridine or via a linker or couple of variable length.

A couple may be described as a linker, i.e. the covalent product formed by reaction of a reactive group designed to attach covalently another molecule at a distance from the calix[n]pyrrole, calix[m]pyridino[n]pyrrole or calix[m]pyridine macrocycle. Exemplary linkers or couples are amides, amine, disulfide, thioether, ether, ester, or phosphate covalent bonds.

In most preferred embodiments, conjugates and appended groups are covalently bonded to the calix[n]pyrrole via a carbon-carbon, carbon-nitrogen, carbon-sulfur, or a carbon-oxygen bond, more preferably a carbon-carbon, carbon-oxygen or a carbon-nitrogen bond.

Preferred embodiments of the present invention include a calix[n]pyrrole where n is 4–8. calix[m]pyrindino[n]pyrrole where m+n is 4–8; other than when each of m and n is 2, and other than when m is 1 and n is 3; or calix[m]pyridine where n is 4–8; where at least one substituent attached to a meso-carbon is carboxy or carboxyalkyl, or at least one subsituent attached to a β- or γ-carbon is other than hydrogen, or at least one substituent attached to a β- or γ-carbon is carboxy, carboxyalkyl, ester or carboxyamide.

Further preferred embodiments of the present invention include a calix[n]pyrrole; a calix[m]pyridino[n]pyrrole where n is 4–8 other than when each of m and n is 2, and other than when m is 1 and n is 3; or calix[m]pyridine where m is 4–8; where at least one of the nitrogen atoms is bound to hydrogen. A calix[4]pyrrole where all pyrrole nitrogen atoms are bound to hydrogen, where meso-carbons are bound to methyl, and one β-substituent is $(CH_2)_tCOOH$ where $0 \leq t \leq 10$. Another preferred calix[4]pyrrole has each of three meso-carbons bridged to itself in a spirocyclohexyl substituent, one meso-carbon is bonded to a methyl group and to a —$CH_2CH_2CH_2COOH$ group, β-subsituents are hydrogen and pyrrolic nitrogens are bound to hydrogen.

Most preferred macrocycles of the present invention are as follows.

| Compound # | Macrocycle |
|---|---|
| 3 | meso-monoester-mono-methyl-tri-spirocyclohexylcalix[4]pyrrole |
| 4 | meso-monoacid-mono-methyl-tri-spirocyclohexylcalix[4]pyrrole |
| 5 | meso-tetravinyltetramethylcalix[4]pyrrole |
| 6 | mesooctabenzylcalix[4]pyrrole |
| 7 | meso-tetraspirotetrahydrothiopyrancalix[4]pyrrole |
| 8 | meso-octanonylcalix[4]pyrrole |
| 9 | meso-tetramethyl-meso-tetraferrocenylcalix[4]pyrrole |
| 10 | β-monoester-meso-octamethylcalix[4]pyrrole |
| 11 | β-diester-meso-octamethylcalix[4]pyrrole |
| 12 | β-monoacid-meso-octamethylcalix[4]pyrrole |
| 13 | β-octamethoxy-meso-tetraspirocyclohexylcalix[4]pyrrole |
| 14 | β-octabromo-meso-octamethylcalix[4]pyrrole |
| 15 | meso-p-tert-butyl-calixarene-tetramethylcalix[4]pyrrole pseudo dimer |
| 16 | calixarene-tetramethylcalix[4]pyrrole-calixarene pseudo trimer |
| 17 | meso-decamethylcalix[5]pyrrole |
| 18 | meso-dodecamethylcalix[6]pyrrole |
| 19 | meso-tetradecamethylcalix[7]pyrrole |
| 20 | meso-hexadecamethylcalix[8]pyrrole |
| 22 | β-octaethyl-meso-octamethylcalix[4]pyrrole |
| 26 | meso-octamethyl-calix[3]pyridino[1]pyrrole |
| 27 | meso-octamethylcalix[4]pyridine |
| 28 | mono-β-butylamidocalix[4]pyrrole |
| 29 | mono-meso-butylamido-heptamethylcalix[4]pyrrole |
| 30 | mono-β-octadecyl-meso-octamethylamidocalix[4]pyrrole |
| 31 | propyl bridged β-amido-meso-octamethylcalix[4]pyrrole dimer |
| 32 | β-amidobenzo-15-crown-5-meso-octamethylcalix[4]pyrrole |
| 33 | Mono-meso-ferroceneamido-mono-methyl-tri-spirocyclohexylcalix[4]pyrrole |
| 34 | Mono-β-ferroceneamido-meso-octamethylcalix[4]pyrrole |
| 35 | meso-tetrakispolyethyleneglycol-meso-tetramethyl substituted calix[4]pyrrole |
| 36 | 2-amido-2-deoxy-1,3,4,6-tetra-O-acetyl-β-D-glucopyranosecalix[4]pyrrole conjugate (chiral) |
| 37 | 2-amido-2-deoxy-β-D-glucopyranosecalix[4]pyrrole conjugate (chiral) |
| 38 | meso-tetraspiro-4-cholesten-3-onylcalix[4]pyrrole (chiral) |
| 39 | meso-tetrabinaphthal-meso-tetramethylcalix[4]pyrrole (chiral) |
| 40 | β-(R)-(+)-α-methylbenzylamidocalix[4]pyrrole (chiral) |
| 41 | meso-N-protected-guanine-meso-trispirocyclohexylcalix[4]pyrrole conjugate |
| 42 | meso-N-protected-cytosine-meso-trispirocyclohexylcalix[4]pyrrole conjugate |

Most preferred are macrocycles 3, 4, 10, 12 and solid supported materials Gel M and Gel B.

While the cited calix[n]pyrroles, calix[m]pyridino[n]pyrroles or calix[m]pyridines are presently preferred for use in the present invention, the invention is not limited thereto and any calix[n]pyrrole, calix[m]pyridino[n]pyrrole or calix[m]pyridine may be used.

Synthetic Methods for Macrocycles of the Present Invention

The present disclosure provides a number of different methods for making macrocycles of the present invention. The following preferred embodiments are described.

Calix[n]pyrroles having an ester functionality at a meso-carbon. A method of making a calix[n]pyrrole having an ester functionality at a meso-carbon comprises reacting a ketone having one or more ester functionalities with a pyrrole in the presence of a Brønsted acid. The method of invention additionally comprises reacting a mixture of ketones containing one or more ester functionalities and ketones not containing ester functionalities with a Brønsted acid to provide a range of ester functionalities. Examples of ketones having one or more ester functionalities include, but are not limited to, methylacetylbutyrate, acetylpropionate and acetylpentanoate. Examples of pyrroles include, but are not limited to, pyrrole, 3,4-diethylpyrrole, 3,4-dimethoxypyrrole or 3-butylpyrrole. Examples of Brønsted acids include, but are not limited to HCl, methanesulfonic acid, toluenesulfonic acid, benzenesulfonic acid, $HClO_4$, formic acid, acetic acid, sulfuric acid or phosphoric acid.

As demonstrated in Example 2, methylacetylbutyrate was reacted with pyrrole and cyclohexanone in the presence of a Brønsted acid to form a macrocyclic structure comprised of n pyrrole units, where n is 4, 5, 6, 7, or 8 and the number of ester functionalities is equal to 1 to n.

Calix[n]pyrroles having an acid functionality at a meso-carbon. This method embodiment for making calix[n]pyrroles having an acid functionalities at a meso-carbon comprises de-esterifying an ester-functionalized calix[n]pyrrole where n is 4, 5, 6, 7 or 8. De-esterifying may be accomplished by heating the ester-functionalized calix[n]pyrrole in a water/ethanol solution in the presence of sodium hydroxide and subsequent acidification and extraction of the calixpyrrole acid.

Addition of an electrophile to a calix[n]pyrrole to form a β-substituted calix[n]pyrrole. This method embodiment comprises activating a calix[n]pyrrole, where n is 4, 5, 6, 7 or 8 and reacting the activated calix[n]pyrrole with an electrophile to make a β-substituted calix[n]pyrrole. Examples of activation include, but are not limited to, deprotonation with a Brønsted base such as n-butyl lithium, tert-butyl lithium, or phenyl lithium, or a Brønsted base in conjunction with a complexing agent such as tetramethylethylenediamine. Examples of electrophiles include, but are not limited to, ethylbromoacetate, methylbromoacetate, acrylonitrile, methyl acrylate, acyl chloride, alkyl halide, functionalized alkyl halides or carbon dioxide. An exemplary method is found in Example 3.

β-Subtituted calix[n]pyrroles. A method of making a β-subtituted calix[n]pyrrole where n is 4, 5, 6, 7, or 8 comprises reacting a β-substituted pyrrole with a ketone in the presence of a Brønsted acid to produce a β-substituted calix[n]pyrrole where n is 4, 5, 6, 7 or 8. Examples of β-substituted pyrroles include, but are not limited to, 3,4-dimethoxypyrrole, 3,4-diethyl pyrrole 3,4-dimethylpyrrole, 3,4 diphenylpyrrole, or 3-butylpyrrole. Examples of ketones include, but are not limited to, acetone, pentan-3-one, dibenzyl acetone, 5-nonone, 4-heptanone, cyclohexanone, or cyclopentanone. Examples of Brønsted acids have been described herein. A method of making a β-substituted calix[n]pyrrole where n is 4, 5, 6, 7 or 8 comprising producing a calix[n]pyrrole radical where n is 4, 5, 6, 7, or 8; and reacting the radical with a radical acceptor molecule such as iodine, methyl acrylate or iodoacetamide. An exemplary method is described in Example 3.

Lewis acid condensation. A pyrrole and a ketone are reacted in the presence of a Lewis acid to form a calix[n]pyrrole where n is 5, 6, 7, or 8. Examples of ketones and pyrroles have been described herein. Examples of Lewis acids include, but are not limited to, electron pair acceptors containing empty orbitals such as aluminum trichloride, boron trifluoride, gallium trichloride, or high valent metals such as titanium (IV), vanadium (V), tin (IV), manganese (III), or $UO_2^{2+}$. Exemplary methods include the methods described in Example 5.

Heterogeneous condensation. A synthetic method for heterogeneous condensation to form calix[n]pyrroles where n is 4, 5, 6, 7 or 8 comprises reacting a pyrrole and a ketone in the presence of a heterogeneous catalyst. Examples of pyrroles and ketone have been described herein. Examples of heterogeneous catalysts include, but are not limited to, montmorrilonite, zeolite, silica gel, alumina, or a cation-exchange solid support. Exemplary methods include those methods found in Example 5.

Calix[n]pyrroles from pyrrole alcohols. A method of synthesis of calix[n]pyrroles using pyrrole alcohols comprises reacting a ketone-functionalized pyrrole with an alkyl metal or aryl metal to form a pyrrole alcohol; condensing the pyrrole alcohol with a Lewis acid, a Brønsted acid or a heterogeneous catalyst to form a cyclizable pyrrole oligomer; and repeating the condensing n-2 times to form a calix[n]pyrrole. Examples of pyrrole ketones include, but are not limited to, 2-acetyl-3,4-diethylpyrrole, 2-acetylpyrrole, 2-acetyl-3,4-dimethylpyrrole, 2-alkylacetyl-3,4-disubstituted pyrrole, 2-alkylacetyl-3-substituted pyrrole, or 2-alkylacetyl-4-substituted pyrrole. Examples of alkyl metals include, but are not limited to, alkyllithium, Grignard reagent, organocuprates, organozincs or organotin compounds. Examples of aryl metals include, but are not limited to, phenyllithium.

Using 2-acetylpyrrole and an alkyl lithium to illustrate the method described herein, 2-acetylpyrrole is reacted with butyl lithium to produce 1-butyl-1-methyl-1-(2-pyrrolo)methanol. 1-Butyl-1-methyl-1-(2-pyrrolo) methanol is condensed with 2-acetylpyrrole in the presence of a Brønsted acid. The reaction is repeated twice to form a calix[4]pyrrole.

Non-Covalent Template synthesis. This synthetic method embodiment comprises reacting a ketone and pyrrole in the presence of a Lewis acid, a Brønsted acid or a heterogeneous catalyst in the presence of a template. Examples of pyrroles, ketones, Lewis acids. Brønsted acids, and heterogeneous catalysts have been given herein. Examples of templates include, but are not limited to, tetraphenylporphyrin, hydrogen bonding neutral molecules, such as sugars, cyclodextrins, alcohols or amines or anionic species such as, halides, carboxylates, sulfonates or phosphates.

Using halides to illustrate, but not limit, the methods of template synthesis of calix[n]pyrroles, pyrrole and acetone would be condensed using a Brønsted acid, a Lewis acid or a homogeneous catalyst in the presence of a halide. By varying the size of the halide, it would be possible to "tune" the size of calix[n]pyrrole where n is 4, 5, 6, 7, or 8.

Pyrrole Ring Expansion. This synthetic method embodiment comprises reacting a calixpyrrole or calixpyridinopyrrole with a halocarbene in a cycloaddition reaction, converting a pyrrole to a pyridine and forming a calixpyridinopyrrole or a calixpyridine. Exemplary procedures for this cycloaddition are found herein in Example 6.

Dihalocarbenes can also be generated from chloroform or bromoform in the presence of a strong base (e.g. tert-BuOK) or under phase transfer catalysis conditions (e.g. in the presence of triethylbenzylammonium bromide) in chloroform or bromoform with a concentrated sodium hydroxide solution (50%).

Calix[n]pyrroles having different substituents at meso-carbons. A method of synthesizing a calix[n]pyrrole where n is 5, 6, 7, or 8 having different substituents at a meso-carbon comprises reacting at least two ketones with a pyrrole in the presence of a Lewis acid. Examplary ketones and Lewis acids are described herein.

Covalent Template synthesis. A method of synthesizing a calix[n]pyrrole where n is 4, 5, 6, 7, or 8 comprising reacting pyrrole or a β-substituted pyrrole with an n-fold cyclic ketone template having n ketone groups is a further embodiment of this invention. n-Fold cyclic ketone templates include, but are not limited to, calix[n]arenes, resorcin[n] arenes, CTV, and cyclic sugars such as the α-, β- or γ-cyclodextrins. Alternatively, benzene rings substituted with ketone groups, or azacrown ethers with N-pendant ketone moieties may serve as templates in the synthesis of the present invention. In one aspect of the invention, it is preferred that the ketone groups of the template all be pointing in the same direction. For example, in the case of calixarenes, the calixarene is in a cone conformation.

One skilled in the art of organic synthesis, in light of the present disclosure, could extend and refine the referenced basic synthetic chemistry to produce calix[n]pyrroles having various substituents. For example, polyether-linked polyhydroxylated groups, saccharide substitutions in which the saccharide is appended via an acetal-like glycosidic linkage, an oligosaccharide or a polysaccharide may be similarly linked to a calix[n]pyrrole. A carboxylated calix[n]pyrrole, calix[m]pyridino[n]pyrrole or calix[m]pyridine in which the acid groups are linked to the calix[n]pyrrole, calix[m]pyridino[n]pyrrole or calix[m]pyridine core via aryl ethers or functionalized alkyl substituents could be converted to various amido products wherein the amide linkages serve to append further substituents. Saccharide moieties may be appended via amide bonds.

Calixarene-calixpyrrole Pseudo Dimers, Multimers and Polymers

Calix[n]arenes are macrocyclic molecules composed of phenol rings linked by methylene groups. According to one aspect of the present invention, calix[n]pyrroles are useful as anion binding agents. A method of the invention comprises reacting a cyclic ketone-containing compound with pyrrole. The number of ketones and the number of pyrroles will be equal to n. The cyclic ketone-containing compound acts as a template upon which the calixpyrrole is formed, after which the synthesized calixpyrrole may be detached from the ketone-containing template. Alternatively, where the template is a calixarene, the resulting cylindrical calix[n]arene-calix[n]pyrrole pseudo dimer may be kept intact.

The cyclic ketone-containing compound may be selected from any cyclophane molecule having n ketone groups. Examples of such molecules include, but are not limited to, calix[n]arenes, resorcinarenes, CTV, and cyclic sugars such as the cyclodextrins. Alternatively, benzene rings substituted with ketone groups, or azacrown ethers with N-pendant ketone moieties may serve as templates in the synthesis of the present invention. In one aspect of the invention, it is preferred that the ketone groups of the template all be pointing in the same direction. For example, in the case of calixarenes, the calixarene is in a cone conformation.

In order to detach a templated calix[n]pyrrole, a cleavable group is present between the template and the ketone. This cleavable group may be covalently linked or non-covalently linked. The cleavage group may be, for example, an ester that can be subsequently hydrolyzed, or a benzyl group that can be hydrogenated or removed with a de-benzylating agent such as $Me_3SiI$. Non-covalent interactions may also be employed, such as carboxylic acid dimerization or metal complexation between the template and the ketone.

In the synthesis, the pyrrole condensation must be acid catalysed; the acid may be selected from a Brønsted acid, such as methanesulfonic acid, HCl, $HClO_4$, $H_2SO_4$, $HNO_3$, TFA, $HCO_2H$, $H_3PO_4$; a Lewis acid such as $VOCl_3$, $Mn(OAc)_3$, $SnCl_4$, $AlCl_3$, or $UO_2(OAc)_2$; and a clay such as montmorrilonite. The synthesis is carried out in an organic solvent that is compatible with the particular ketone-containing template utilized. Solvents such as chloroform, dichloromethane, acetonitrile, carbontetrachloride, toluene, benzene, and mixtures of these solvents with methanol, ethanol, propanol, and the like may be used. The linker to the ketone could also be changed to include any spacer such as benzyl groups, alkynes, alkenes, ethers, polyethers, thioethers, bipyridyl, phenanthroline, anthracene, naphthalene, any polyaromatic, quinone, ferrocene, cobaltocenium or other metallocene, and the like.

Using calixarenes to illustrate the method of the present invention, the calix[4]arene skeleton is used as a template, around which a calix[4]pyrrole forms. Although calixarene-linked and calixarene-capped porphyrins as well as calixarenes linked to pyrrole groups are known, to the best of the present inventors knowledge, compound 15 represents the first example of a calixarene-capped calixpyrrole.

Calc[n]pyrroles Derivatives, Multimers, and Conjugates.

Example 8 provides for the synthesis of different and exemplary derivatives, multimers or conjugates of calix[n] pyrroles. With use of either the meso-"monohook" acid 4 or the β-"monohook" acid 12 there exist possibilities of substitution through various functional groups. Formation of an amide bond, for example, could lead to attachment of natural nucleotides as well as the "unnatural" nucleotide analogues. Using nucleotide-functionalized calixpyrroles, it may be possible to do through-membrane transport of nucleotide analog drugs such as AZT, acyclovir, and the like (Example 11). Using the case of calix[4]pyrrole by way of illustration, one skilled in the art in light of the present invention would appreciate that in addition to one "hook", one may add two, three, four, five, six, seven, or eight "hooks" at the meso- or β-positions of the calixpyrrole. Arrays of calixpyrroles spanning membranes and acting as anion channels analogous to cation channels are contemplated by the present inventors. By using poly-amine-containing compounds, dimers, trimers and tetramers of calixpyrrole could be used as carriers for transporting polyanionic species through aliphatic membranes. Through NMR work and work with HPLC, it has been determined that calix[4]pyrroles show a higher affinity for phosphate anions than other oxyanions. With this in mind, arrays of calixpyrroles could be used to encircle RNA and DNA molecules, thus providing anti-viral activity. Specificity of binding could be gained by attaching specific nucleotides to the calixpyrrole oligomer. Attachment of known nucleotide cleaving agents such as Fe-EDTA could facilitate the site directed cleavage of RNA. Calix[4]pyrrole also binds to carboxylic acid groups by HPLC and could be used for extraction of pesticide and herbicide metabolites. Additionally, with the addition of a cation-binding functionality, amino acid recognition and transport are possible. A solid silica-supported calix[4]pyrrole has shown selectivity of various N-benzyl protected amino acids. This could lead to specific binding of proteins and interuption of enzymatic pathways. The attachment of sugars, and mono- and polysaccharides to the calixpyrrole could allow for recognition of compounds such as glucose-6-phosphate.

By attachment of a redox-active reporter group; calix[n]pyrrole, calix[m]pyridino[n]pyrrole or calix[m]pyridine macrocycles may function as potentiometric or amperometric sensors for cations, anions, or neutral molecules.

By attachment of a fluorophoric reporter group; calix[n]pyrrole, calix[m]pyridino[n]pyrrole or calix[m]pyridine macrocycles may function as fluorescent sensors for cations, anions, or neutral molecules.

By attachment of a chromophoric reporter group; calix[n]pyrrole, calix[m]pyridino[n]pyrrole or calix[m]pyridine macrocycles may function as chromophoric sensors for cations, anions, or neutral molecules.

Calix[n]pyrroles, Calix[m]pyridino[n]pyrroles and Calix[m]pyridines as Separation Media Separation of closely similar molecules from highly complex mixtures requires high resolution techniques. Ion exchange, affinity chromatography, reverse phase chromatography and gel filtration represent current types of separation techniques. The present macrocycles provide a new type of separation media due to non-covalent, primarily hydrogen bonding, interaction between the macrocycle and a guest.

In ion exchange, separation is based on charges carried by the solute molecules. An ion exchanger includes an insoluble matrix or solid support to which charged groups have been covalently bound. The charged groups are associated with mobile counterions. The counter ions can be reversibly exchanged with other ions of the same charge without altering the matrix. It is possible to have both positively and negatively charged exchangers. Positively charged exchangers have negatively charged ion (anions) available for exchange and are so termed cation exchangers. Negatively charged exchangers have positively charges counterions and are termed cation exchangers. The matrix may be based on inorganic compounds, synthetic resins, polysaccharides, silicas, aluminas, or polymeric supports. The nature of the matrix determines its physical properties, such as its mechanical strength and flow characteristics, its behavior towards test samples, and to some extent, its capacity.

Affinity chromatography is a type of adsorption chromatography in which the molecule to be purified is specifically and reversibly adsorbed by a complementary binding substance (ligand) immobilized on an insoluble support (matrix). Cyanogen bromide activation has been the most common method for coupling ligands to a matrix. A successful separation requires that a ligand is available and that it can be covalently attached to a chromatatographic bed material. It is also important that the immobilized ligand retain its specific binding affinity for the substance of interest and that methods are available for selectively desorbing the bound substances in an active form, after washing away unbound material.

Reverse phase chromatography relies on hydrophobic surfaces, especially silylated alkyl ($R_1$, $R_2$, $R_3$, SiO), on the solid support to bind hydrophobic molecules. More polar molecules pass through the column unimpeded. The hydrophobic media may include aromatic molecules, long chain aliphatic hydrocarbons, or cyclic hydrocarbons.

Separation in gel filtration depends on the different abilities of the various sample molecules to enter pores in a stationary phase. As a solute passes down a chromatographic bed, its movement depends upon the bulk flow of the mobile phase and upon the Brownian motion of the solute molecules which causes their diffusion into and out of the stationary phase. Very large molecules that never enter the pores move through the chromatographic bed fastest. Smaller molecules that can enter the gel pores move more slowly through the column since they spend a proportion of their time within the pores. Molecules are, therefore, eluted in the order of decreasing molecular size.

In contrast to the known methods of chromatography, the macrocycles of the present invention provide new principles for separation of ions and molecules. Interactions between macrocycles of the present invention and ions and molecules are noncovalent, primarily hydrogen bonding. As a result, surprising and unexpected affinities and selectivities are observed for the separation of very similar molecules. For instance, the following sets of anions or neutral molecules were successfully separated (Example 10):

Phenyl arsenate, benzene sulfonate, benzoate, and phenyl phosphate;

5'-Adenosine monophosphate, 5'-adenosine diphosphate and 5'-adenosine triphosphate;

Uridine, phenol, aniline, benzene, and 4-iodo-nitrobenzene;

Cbz-N-protected-serine, -glutamine, -alanine, -phenylalanine, -tryptophan, -aspartate, and -glutamate;

4-Fluorobiphenyl, 4,4'-difluorobiphenyl, 2,2',3,3',5,5',6,6',-octafluorobiphenyl, and perfluorobiphenyl;

A mixture of polydeoxythymidylates oligomers containing between (12) and (18) bases;

A mixture of polydeoxythymidylates oligomers containing between (19) and (24) bases;

TCTAGA, GCATGC, and CCCGGG;

Phthalate, isophthalate and teraphthalate;

Benzoate, isophthalate, and 1,3,5-tricarboxybenzene; and

Carbofuran, carbendazim, bromacil, bentazon, carboxin, and norflurazon.

A method of use of the present invention comprises separating a first molecule, a first anion or a first cation from a mixture of a first molecule, first anion or first cation, and other species, using a form of solid support-immobilized calix[n]pyrrole, calix[m]pyridino[n]pyrrole or calix[m]pyridine by contacting the solid support with the mixture to separate a first molecule, first anion or first cation from a mixture of first molecule, first anion or first cation and other species. Examples of solid supports include, but are not limited to, silica gel, aminopropyl silica gel, carboxylalkylated silica gels, chloromethylated silica gel, chloroalkylated silica gel, other functionalized silica gels, alumina, polyacrylamide polymer beads, polystyrene polmer beads, sepharose, sephadex, agarose, clays, or zeolites coupled to calix[n]pyrroles, calix[m]pyridino[n]pyrroles or calix[m]pyridines. Examples of forms of solid supports include, but are not limited to chromatography columns, thin-layer chromatographic supports, electrophoresis gels, or capillary electrophoresis tubes. Examples of ions or neutral molecules to be separated are neutral aromatic or aliphatic species (polymeric, oligomeric and monomeric), a polyhalobiphenyl (including polychlororbiphenyl), or anionic species (polymeric, oligomeric and monomeric) such as nucleotides, oligonucleotides, pertechnetate, polyoxometalates or inorganic phosphate.

The inventors' discovery that calix[n]pyrroles recognize and bind phosphate anions led the inventors to reason that such macrocycles would be ideal for use in techniques to separate and purify oligonucleotides. Data provided in Example 10 demonstrate that this is the case.

The present inventors realized that for a solid support to be most useful, it must not only separate similar nucleotides and oligonucleotides from one another, it must do so rigorously and correctly based on chain length or size. Unfortunately, prior to the present invention, there were no suitable phosphate chelating agents which made this an achievable goal for use in either HPLC or electrophoretic separation systems. As described in Example 10, the inventors designed and constructed calixpyrrole-based supports and used them to achieve the separation of nucleotides and oligonucleotides, thus overcoming many of the existing drawbacks.

A further utility of such calixpyrrole-substituted materials is their use as tools in the removal of phosphorylated environmental contaminents from ground water, soil, foodstuffs, and the like. They may therefore be employed to analyze and separate pesticides such as, but not limited to, carbofuran, carbendazim, bromacil, bentazon, carboxin and norflurazon. Calixpyrrole-substituted silica gels and columns may be employed in the rapid detection and analysis of organophosphorus chemical warfare agents, allowing them to be disposed of where necessary.

Another technical area in which significant improvements could be made is in oligonucleotide analysis. For example, automated gene sequencing is currently carried out using either radio- or fluorescent labeled nucleic acid gel electrophoresis. This technique is limited by the requirement for either slab or tubular polyacrylamide gels. An alternative approach, currently being considered on a research basis, is to use capillary electrophoresis. Unfortunately, this is limited when it comes to achieving separations based purely on electrostatics and oligomer size. A technique, such as the present invention, which would allow for such separation would therefore represent a significant improvement in this area.

A method of making a solid-supported calix[n]pyrrole, calix[m]pyridino[n]pyrrole or calix[m]pyridine macrocycle comprising attaching the macrocycle having a functionalized group to a solid support, the solid support reactive with the functionalized group, or to a tether-functionalized solid support, the tether reactive with the functionalized group is a further embodiment of this invention. An exemplary method is described in Example 10.

Two new derivatized silica gels have been produced. Gel M is aminopropyl silica gel linked to the attached calixpyrroles via a calixpyrrole meso-carbon and Gel B is aminopropyl silica gel linked to the appended calixpyrrole via a calixpyrrole β-carbon. Both gels have been demonstrated to separate mixtures of anions such as oligonucleotides ($dT_{12-24}$), nucleotides, aromatic polycarboxylates, phenyloxoanions, halides, phosphates and sulfates in an HPLC column (Example 10). Additionally, the calixpyrrole-modified silica gels can separate mixtures of neutral molecules such as polyfluorobiphenyls and other aromatic species. Thus, the calixpyrrole modified column supports offer a wide range of separatory ability.

The macrocycle modified solid support in the form of a chromatography column or capillary electrophoresis tube or a contacting process involving the macrocycle modified solid support in a batch process is an embodiment of this invention.

A method of forming a complex of a calix[n]pyrrole or a calix[m]pyridino[n]pyrrole and an anion or a neutral molecule, comprising contacting the calix[n]pyrrole or the calix[m]pyridino[n]pyrrole with the anion or neutral molecule under conditions effective to allow the formation of the complex is another embodiment of this invention.

Another embodiment of this invention is a method of transporting a molecular or ionic species through a membrane comprising incorporating a calix[n]pyrrole or a calix[m]pyridino[n]pyrrole into the membrane; and contacting the membrane with the molecular or ionic species in the presence of a gradient of the molecular or ionic species, or a counter gradient of a further species. The transporting may result in the purification of the molecular or ionic species.

Additionally binding a cation comprising contacting the cation with a calix[n]pyrrole or calix[m]pyridino[n]pyrrole having a cation-binding functionality, or with a calix[m]pyridino[m]pyrrole or calix[m]pyridine is an embodiment of this invention.

Removal of pertechnetate from pertechnetate-containing nuclear waste comprising contacting the waste with a calix[n]pyrrole or a calix[m]pyridino[n]pyrrole to form a calix[n]pyrrole- or a calix[m]pyridino[n]pyrrole-pertechnetate complex; and removing the complex from the waste is an embodiment of this invention.

A method of removal of an environmental pollutant from an environmental source, comprising contacting the environmental source with a calix[n]pyrrole or a calix[m]pyridino[n]pyrrole to form a calix[n]pyrrole- or a calix[m]pyridino[n]pyrrole-pollutant complex, and removing the complex from the environmental source is a further embodiment of this invention. See Example 12 for examples of removing pertechnetate from nuclear waste. Environmental pollutants such as, but not limited to nitrates, phosphates, polychlorobiphenyls, and fluoride are damaging to the environment. See Example 12 for examples of removing environmental pollutants using macrocycles.

A sensor comprising a solid support bound to a macrocycle of the present invention is a further embodimnt of the present invention. A sensor can be made by either electropolymerizing the macrocycle onto the surface of the solid support or encapsulating the macrocycle into a membrane attached to the surface of the solid support is envisioned to act as an electrochemical sensor for ionic or molecular species.

The calix[n]pyrrole where n is 5, 6, 7, or 8 may be associated with a metal that is bound by substituents on the periphery of the macrocycle. Heterocyclic macrocyles containing free electron pairs chelate cations. Pyridine is known to coordinate to certain cations. Calix[m]pyridines also contain nitrogen atoms that are expected to donate electron density to cations. This donation would require that the cations stay in close proximity to the pyridine units, thereby, binding the cations to the core of the ring.

In Vivo Applications

Calix[n]pyrroles, calix[m]pyridino[n]pyrroles or calix[m]pyridines in DNA recognition and modification. Water-soluble calix[n]pyrroles, calix[m]pyridino[n]pyrroles or calix[m]pyridines may be particularly advantageous for use in a number of ways, such as in cellular recognition, targeting, and in the transport of biologically important molecules. Generally, water-soluble calix[n]pyrroles are preferred for biomedical applications. "Water soluble" means soluble in aqueous fluids to about 1 mM or better.

Anionic phosphorylated entities are ubiquitous in biology. They play a critical role in a variety of fundamental processes ranging from gene replication to energy transduction. In addition, certain phosphate-bearing nucleotide analogues, such as, e.g., 9-(β-D-xylofuranosyl)guanine-5'-monophosphate (xylo-GMP), are known to display antiviral activity in vitro. However, xylo-GMP, like a considerable number of phosphorylated nucleotide analogues which exhibit antiviral activity in cell-free extracts, is inactive in vivo due to its inability to cross lipophilic cell membranes.

The anti-herpetic agent, acyclovir (9-[(2-hydroxyethoxy) methyl]-9H-guanine), is active in vivo. Acyclovir can enter the cell only in its uncharged nucleoside-like form. Once in the cytoplasm, it is phosphorylated, first by a viral encoded enzyme, thymidine kinase, and then by relatively non-specific cellular enzymes to produce an active ionic triphosphate nucleotide-like species. There, it functions both as an inhibitor of the viral DNA polymerase and as a chain terminator for newly synthesized herpes simplex DNA.

The biological limitations of many other potential antiviral agents, including xylo-G, arise from the fact they are not phosphorylated once inside the cell and are therefore largely or completely inactive. If, however, the active monophosphorylated forms of these putative drugs could be transported into cells, it would be possible to fight viral infections with a large battery of otherwise inactive materials. If such specific into-cell transport were to be achieved, it would therefore greatly augment the treatment of such debilitating diseases as, for example, AIDS, herpes, hepatitis and measles. Given the fact that AIDS is currently a major world health problem of frightening proportions, and that something so nominally benign as measles still claims over 100,000 lives per year world-wide, treatment of these diseases would be particularly timely and worthwhile.

A major aim of the inventors' studies has been therefore to provide a means of transporting active mono- and poly-phosphorylated forms of these and other agents into cells. This would allow a wide range of otherwise inactive compounds, such as antivirals, to be employed therapeutically, and would also create new possibilities for gene therapy.

Calix[n]pyrrole- or calix[m]pyridino[n]pyrrole-based systems may be made effective as neutral regime carriers, say, e.g., for GMP by constructing a of polytopic receptor system in which a nucleobase recognition unit, in this case, a cytosine-like group, is appended directly to a phosphate-chelating calix[n]pyrrole or calix[m]pyridino[n]pyrrole macrocycle. Nucleobase recognition units are demonstrated herein for use in the specific binding and transport of complementary nucleobases and nucleobase-containing compounds.

To synthesize multitopic receptors, calix[n]pyrrole conjugates were developed to address the following objectives: (i) the independent development of molecular recognition strategies for the complexation of two very different kinds of substrates (charged anionic and neutral nucleobase); (ii) subsequent co-combination so as to provide receptors bearing both kinds of binding subunits; and (iii) various alternative methods of receptor oligomerization so as to provide oligomeric species bearing numerous combinations of multitopic receptors.

Pursuing these strategies led to the development of the calix[n]pyrrole-based ditopic receptor systems of the present invention, capable of recognizing both the anionic phosphate and the neutral portions of the nucleotide derivatives, such as the purine or pyrimidine moieties. The present inventors envisage expanding this theme to the preparation of oligomeric, multitopic receptors capable of recognizing multiple phosphate anions and nucleobase portions of nucleotide derivatives arranged in specific sequences.

Ditopic receptor systems are ideal vehicles for the intracellular transport of oligonucleotides and their derivatives, including anti-viral agents. The multitopic receptors, likewise, are contemplated to be of use in binding to oligonucleotides and specific sections of DNA or RNA and in transporting such nucleic acid segments into cells.

Pharmaceutical Preparations

For in vivo and ex vivo uses, calix[n]pyrroles, calix[m]pyridino[n]pyrroles and calix[m]pyridines are provided as pharmaceutical preparations. A pharmaceutical preparation of a calix[n]pyrrole, calix[m]pyridino[n]pyrrole or calix[m]pyridine may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining a calix[n]pyrrole, calix[m]pyridino[n]pyrrole or calix[m]pyridine of the present invention and the pharmaceutically acceptable carriers are then easily administered in a variety of dosage forms. Administration may be intravenous, intraperitoneal, parenteral, intramuscular, subcutaneous, oral, or topical, with intravenous administration being preferred.

Solutions of the calix[n]pyrroles, calix[m]pyridino[n]pyrroles or calix[m]pyridines in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Topical creams, emulsions, solutions, and the like are contemplated for applications to surface areas of the body. Topical application may also be by iontophoresis.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy use with a syringe exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars such as mannitol or dextrose or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, permeation enhancers, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Calix[n]pyrroles, calix[m]pyridino[n]pyrroles or calix[m]pyridines may be incorporated into liposomes for use in the present invention. Liposomes may be prepared by any number of techniques that include freeze-thaw, sonication, chelate dialysis, homogenization, solvent infusion, microemulsification, spontaneous formation, solvent vaporization, reverse phase, French pressure cell technique, or controlled detergent dialysis, for example. Preparation may be carried out in a solution, such as a phosphate buffer solution, containing calix[n]pyrrole-, calix[m]pyridino[n]pyrrole or calix[m]pyridine-lipophilic molecule conjugates so that the conjugate is incorporated into the liposome membrane. Alternatively, the conjugate may be added in already formed liposomes. Liposomes employed in the present invention may be of any one of a variety of sizes, preferably the less than about 100 rim in outside diameter, more preferably less than about 50 nm.

Micelles may be prepared by suspension of a calix[n]pyrrole-, calix[m]pyridino[n]pyrrole- or calix[m]pyridine-lipophilic molecule and lipid compound(s) in an organic solvent, evaporation of the solvent, resuspension in an aqueous medium, sonication and then centrifugation. Alternatively, the calix[n]pyrrole-, calix[m]pyridino[n]pyrrole- or calix[m]pyridine-lipophilic molecule may be added to pre-formed micelles.

Techniques and lipids for preparing liposomes and micelles are discussed in U.S. Pat. No. 5,466,438, incorporated herein by reference.

Use of Calix[n]pyrroles, Calix[m]pyridino[n]pyrroles, or Calix[m]pyridines in Ex Vivo and in In Vivo Treatment of Body Tissues.

Use of macrocycles of the present invention includes the dialysis of bodily fluids. Examples of dialyzable substrates include, but are not limited to, phosphate-containing molecules or halide waste. Examples of conditions for treatment include gout, diabetes, or drug overdoses.

Using kidney dialysis to illustrate an ex vivo treatment, bodily fluid would be contacted with a calix[n]pyrrole, a calix[m]pyridino[n]pyrrole, or a calix[m]pyridine. Phosphate bound by the macroycle is removed from the blood.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Novel Crystal Structures of Complexed Prior-Art meso-Substituted Calixpyrrole Macrocycles The present inventors have crystallized anion- and neutral molecule-complexed forms of known calix[4] pyrrole macro cycles and have studied the coordination properties of calixpyrroles in solution and in the solid state. As a result, the present inventors have demonstrated unexpected crystalline forms of calixpyrrole macrocycles and the existence of a conformational change between an unbound macrocycle and a macrocycle bound to an anion or a neutral substrate. In the solid state, uncomplexed calix[4]pyrrole macrocycles adopt an alternate conformation where adjacent pyrrole rings are oriented in opposite directions. Solid-state complexed calix[4]pyrrole macrocycles are shown herein to adopt a cone conformation such that the four NH protons of the pyrrole rings hydrogen bond to the bound substrate forming a supramolecular ensemble. In solution, a dynamic equilibrium exists where the bound anionic or neutral substrate is reversibly bound to all or less than all of the pyrrole NH groups. Such a conformational change would alter the properties of the calixpyrrole, for example, groups on the meso- or β-positions would be brought into closer proximity in the cone configuration. This conformational change may be taken advantage of in the design of a sensor, for example.

meso-Octamethylcalix[4]pyrrole 1 was prepared using prior art procedures in the following manner. Pyrrole (20 g) and acetone (20 g) were introduced into a stirred 500 mL round-bottomed flask fitted with a reflux condenser. Methanesulfonic acid (1 mL) was added down the reflux condenser, causing a violent reaction. CARE!—The acid must be added slowly! Once the acid was added, the solid mass formed was broken up and a further 20 mL of acetone was added. The mixture was then heated at reflux for 30 min. After this time, the mixture was allowed to cool and the white precipitate was filtered off.

The white precipitate was crystallized from acetone to give a crude crystalline material. This was recrystallized from acetone, giving crystals of the product meso-octamethylcalix[4]pyrrole 1, suitable for single crystal X-ray diffraction studies.

meso-Tetraspirocyclohexylcalix[4]pyrrole 2 was prepared according to prior art procedures as follows. A solution of 16.2 g (0.242 mol) of pyrrole and 20 mL of absolute ethanol was placed in three-necked 500 mL flask. The flask, fitted with a reflux condenser, was placed in an ice bath. To the stirred solution was added dropwise 1 mL of 37% aqueous hydrochloric acid solution, followed by 23.7 g (0.242 mol) of cyclohexanone over a period of 20 min. The stirrer was stopped by the solid formed in the flask when the addition of cyclohexanone was complete. After standing at room temperature for 1 hour, the product was washed with 50 mL of cold water. The solid was removed from the flask by partial dissolution in ether. The total yield of the crude synthesis was 12.86 g (9.0%).

Several crystallizations of the product from benzene and then from hexane save white crystals of tetraspirocyclohexylcalix[4]pyrrole 2, m.p. 272.0–272.5°.

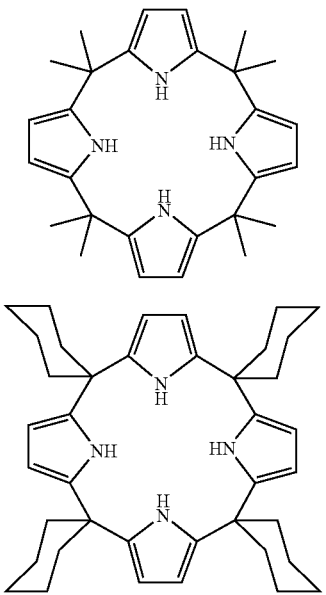

Figure 1B:
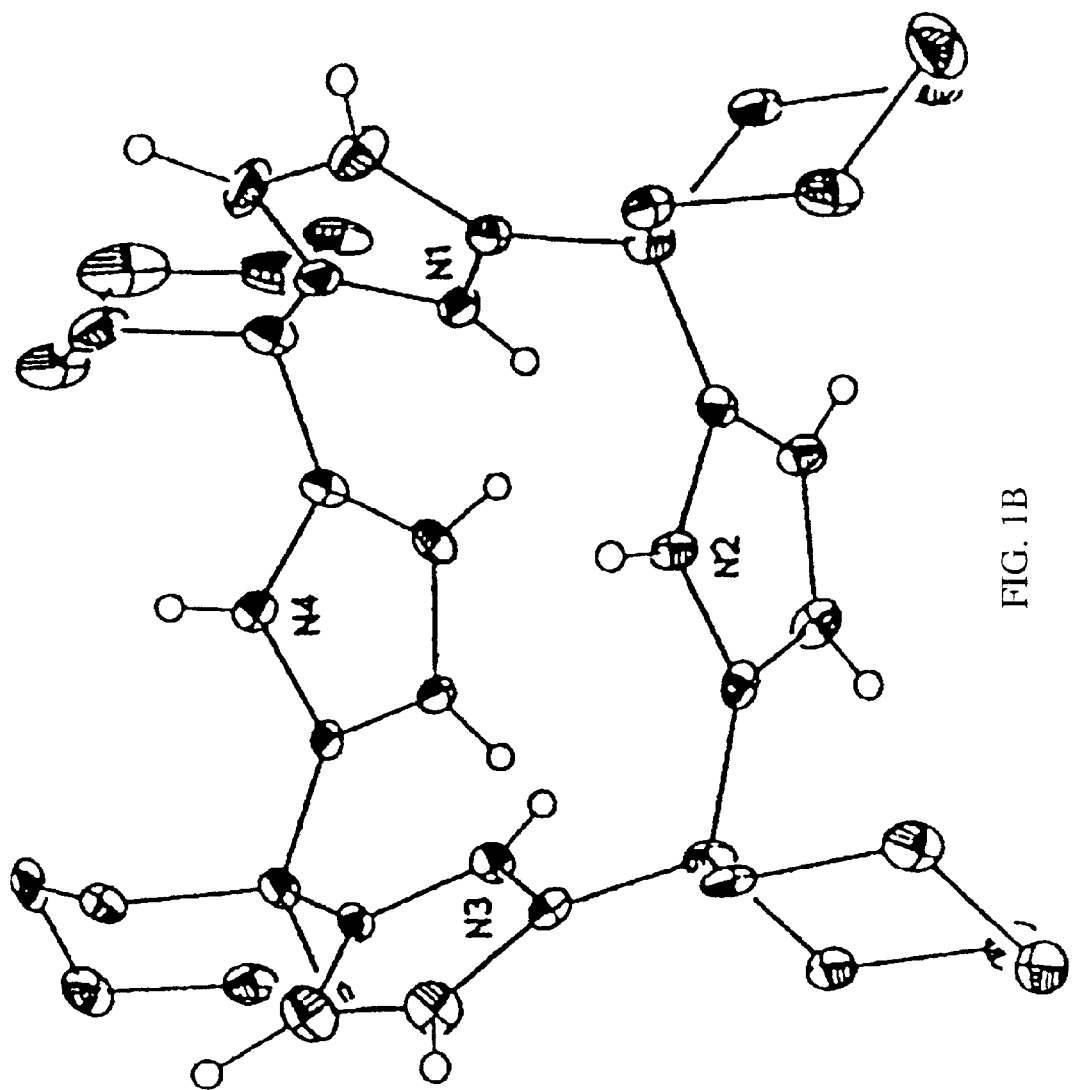
FIG. 1B illustrates the X-ray crystal structure of meso-tetraspirocyclohexylcalix[4]pyrrole, 2, adopting a 1,3-alternate conformation. Thermal ellipsoids are at the 30% probability level.

X-ray Crystallographic Data. Single crystals suitable for X-ray crystallographic analysis were obtained by slow evaporation of acetone and acetone/dichloromethane (1:1 v/v) solutions of calixpyrroles 1 and 2, respectively. The crystallographic summary for 1 is as follows. Pale yellow crystals, tetragonal, P4$_1$, Z=2 in a cell of dimensions a=10.097(1) Å, c=23.764(1) Å, V=2422.7(4)Å$^3$. $\rho_{calc}$=1.18 g cm$^{-3}$. F(000)=928. Data were collected at 198K on a Siemens P4 diffractometer, equipped with a Nicolet LT-2 low-temperature device and using graphite monochromatized Mo Kα radiation (λ=0.71073 Å). Data were collected using ω scans with a scan range of 1° in ω. 3733 unique reflections, 2552 with F$_0$>4(σ(F$_0$)). The final R=0.0556, R$_w$=0.132, goodness of fit=0.999 for 290 parameters. The crystallographic summary for 2.(CH$_2$Cl$_2$) is as follows. Colorless crystals, monoclinic, P2$_1$/c, Z=4 in a cell of dimensions a=10.993(2) Å, b=14.250(3) Å, c,=23.466(4) Å, β=97.254(14)°, V=3646.5(11) Å$^3$. $\rho_{calc}$=1.23 g cm$^{-3}$, F(000)=1448. Data were collected on a Siemens P3 diffractometer. 5562 unique reflections, 2285 with F$_0$>4(σ(F$_0$)). The final R=0.0762, Rw=0.141, goodness of fit=0.995 for 424 parameters. As illustrated in FIG. 1A and FIG. 1B, molecules 1 and 2 adopt a 1,3-alternate conformation in the solid state wherein adjacent rings are oriented in opposite directions similar to a previously-reported octaethyl analogue.

Crystals of anion complexes of the calixpyrroles 1 and 2 were then prepared in order to study the conformational changes from the free ligand to the complexed ligand. Crystals of the tetrabutylammonium chloride complex of calixpyrrole 1 were obtained by slow evaporation of a dichloromethane solution containing an excess of the chloride salt. The crystallographic summary for 1.(n-Bu$_4$NCl). CH$_2$Cl$_2$, is as follows: Colorless crystals, Orthorhombic, Pna2$_1$, Z=4 in a cell of dimensions a=21.247(3) Å, b=19.937 (2) Å, c=10.691(1) Å, V=4528.7(9) Å$^3$, $\rho_{calc}$=1.16 g cm$^{-3}$, F(000)=1720 6027 unique reflections, 3566 with F$_0$>4(σ (F$_0$)). The final R=0.0959, Rw=0.246, goodness of fit=1.224 for 478 parameters. Crystals of the tetrabutylammonium fluoride complex of compound 2 were obtained using a similar procedure and the crystallographic summary for 2.(n-Bu$_4$NF) is as follows. Colorless crystals, tetragonal, P4/nnc, Z=4 in a cell of dimensions a=15.732(1) Å, c=20.076(1) Å, V=4968.7(5) Å$^3$, $\rho_{calc}$=1.14 g cm$^{-3}$, F(000)= 1872. 3634 unique reflections, 2220 with F$_0$>4(σ (F$_0$)). The final R=0.064, Rw=0.171, goodness of fit=1.029 for 152 parameters.

Figure 2A:
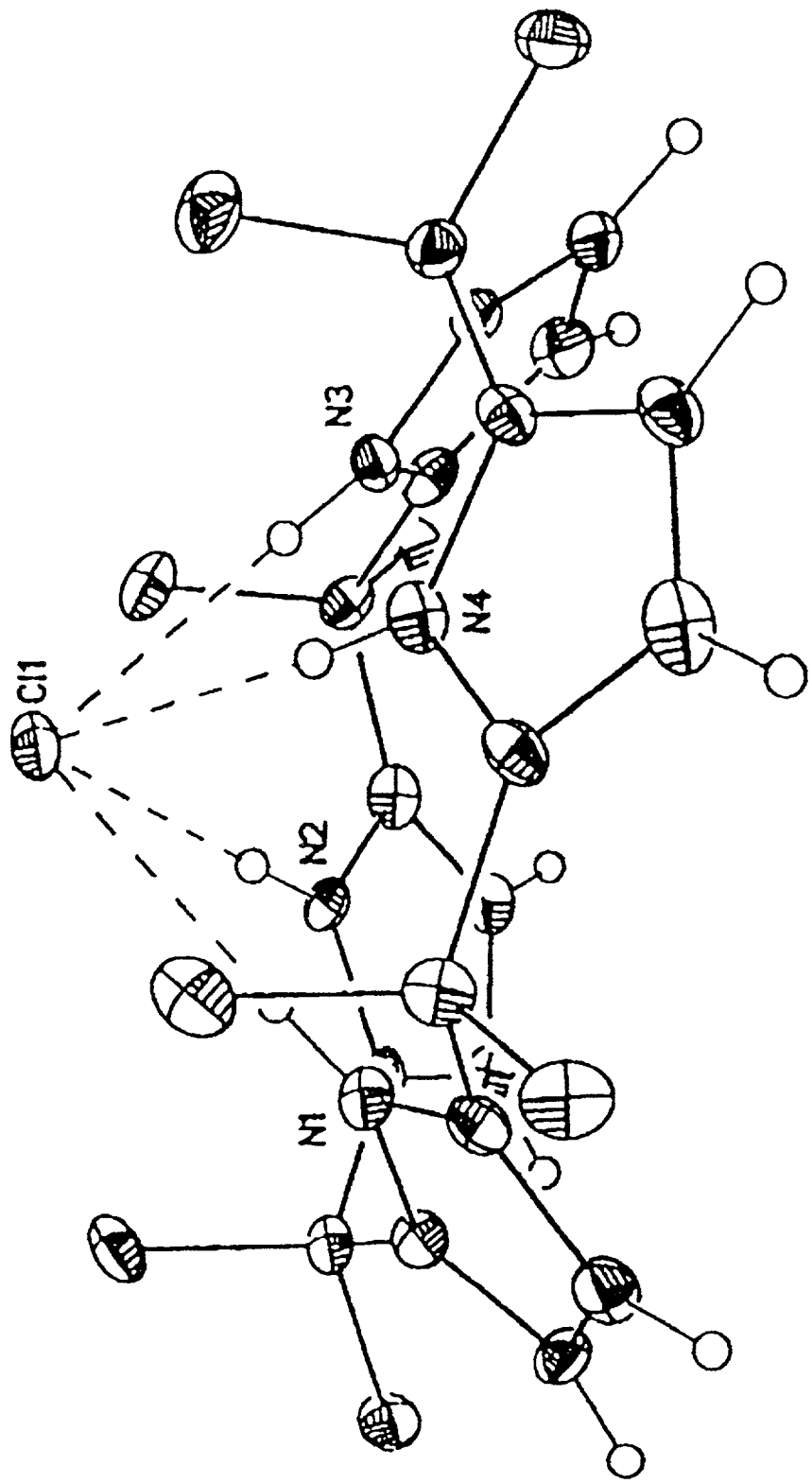
FIG. 2A illustrates the X-ray crystal structure of meso-octamethylcalix[4]pyrrole tetra-butylammonium chloride complex, 1.Cl⁻. The meso-octamethylcalix[4]pyrrole adopts a cone conformation wherein all four pyrrole NH groups are hydrogen-bonded to the bound chloride anion. The counter cation is omitted for clarity. Thermal ellipsoids are at the 30% probability level.
Figure 2B:
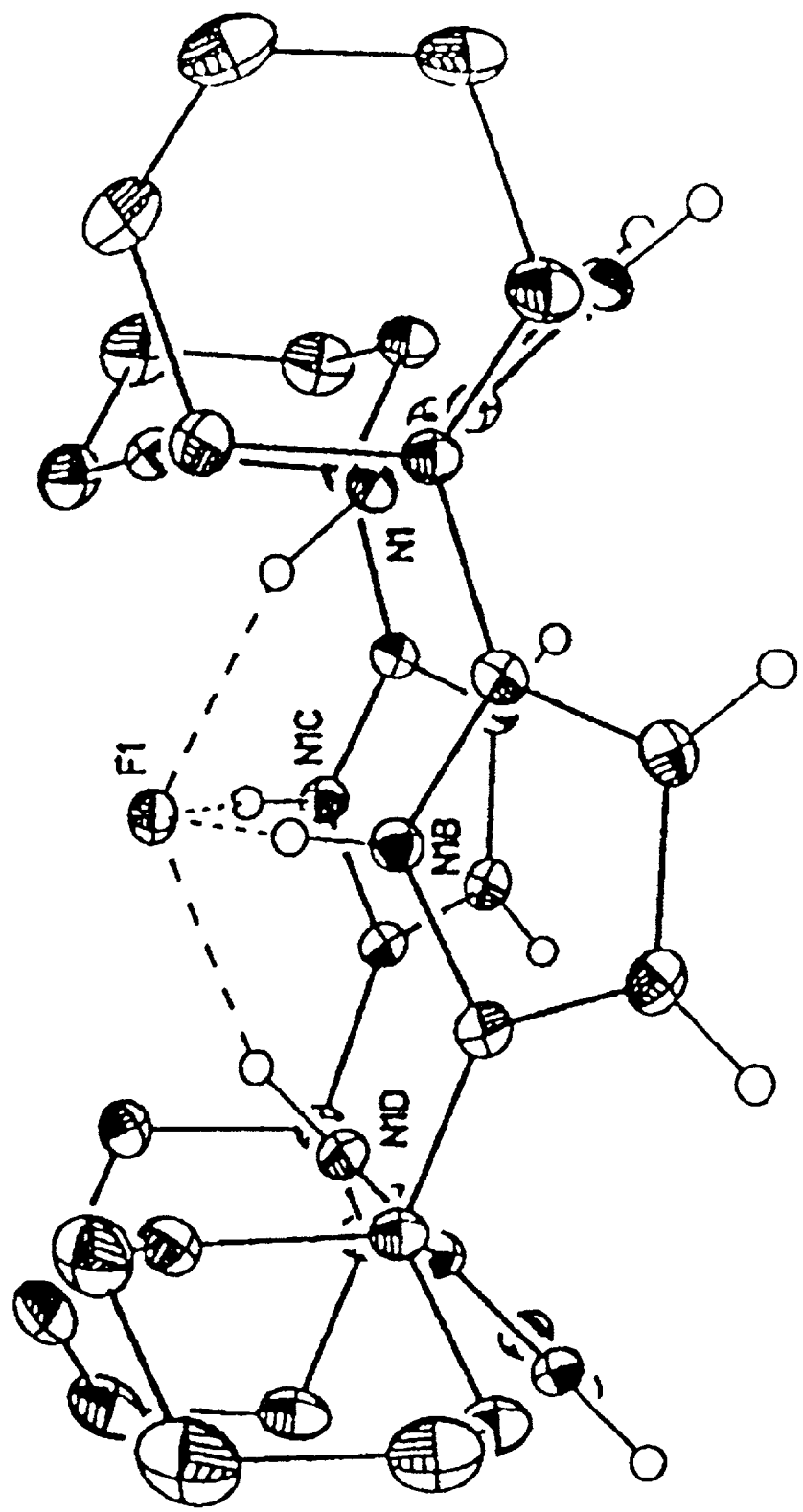
FIG. 2B illustrates the X-ray crystal structure of meso-tetraspirocyclohexylcalix[4]pyrrole tetrabutylammonium chloride complex, 2.Cl⁻. The meso-tetraspirocyclohexylcalix[4]pyrrole adopts a cone conformation wherein all four pyrrole NH groups are hydrogen-bonded to the bound chloride anion. The counter cation is omitted for clarity. Thermal ellipsoids are at the 30% probability level.

The structures so obtained (FIG. 2A and FIG. 2B) reveal that in both cases the calix[4]pyrrole ligand adopts a cone-like conformation such that the four NH protons can hydrogen bond to the bound halide anion. While these two structures are thus grossly similar, in the case of the chloride complex (FIG. 2A) the nitrogen-to-anion distances are in the range of 3.264(7)–3.331(7) Å, while for the corresponding fluoride complex they are 2.790(2) Å (FIG. 2B) (the four pyrrole groups are equivalent by symmetry). As a result, in these two complexes the chloride and fluoride anions reside 2.319(3) Å and 1.499(3) Å above the N$_4$ root mean square planes of calixpyrroles 1 and 2, respectively. Thus, fluoride anion appears to be more tightly bound in the solid state.

Expanding the range of potential guests, complexes of neutral species were then prepared. Crystal complexes of calixpyrrole 1 and N,N-dimethylformamide ("1.2(DMF)") were grown by dissolution of compound 1 in DMF and subsequent crystallization. The N$_{pyrrole}$ . . . O$_{DMF}$ distances are 2.908(2) and 2.924(2) Å, with associated N—H . . . O angles of 167(2)° and 166(2)°, respectively. The unsaturated portion of the amide lies 3.363(3) Å above the plane of a third pyrrole ring (the planar twist angle between these two moieties is 7.1(1)°), suggesting that a π-stacking interaction helps to stabilize 1.2(DMF). The crystallographic summary for 1.2(DMF) is as follows: colorless prisms from DMF, triclinic space group P$\bar{1}$, Z=1, a=9.473(1) Å, b=9.573(1) Å, c=10.316(1) Å, α=66.428(4)°, β=80.987(5)°, γ=72.025(4)°, V=815.00(14) Å$^3$, $\rho_{calc}$=1.17 g cm$^{-1}$, F(000)=312. Final R=0.0390, R$_w$=0.0952, GOF=1.061 for 291 parameters. The NH protons of 1.2(DMF) were obtained from a ΔF map and refined with isotropic thermal parameters.

Crystal complexes of calixpyrrole 1 and methanol ("1.2 (CH$_3$OH)") have also been studied by X-ray crystallography. The crystals were prepared by slow evaporation of a methanol/dichloromethane solution of the ligand. The calixpyrrole unit in 1.2(MeOH) was found to assume a 1,3-alternate conformation in the solid state. Single molecules of the alcohol lie above and below the macrocycle, each one held in place by hydrogen bonds to two pyrrolic NH groups. The four symmetry-equivalent H-bonds (N$_{pyrrole}$ . . . O$_{MeOH}$) are 3.155(4) Å long, a value which is very close to the N$_{pyrrole}$ . . . O$_{MeOH}$ distances (ca. 3.0–3.2 Å) found in a methanol complex of a tetrapyrrolic "expanded porphyrin." Further evidence that methanol is bound to 1, rather than merely occupying space in the lattice, is given by the inward tilt of the pyrroles of 1.2(MeOH). This effect compresses the "cross ring" N$_1$ . . . N$_{1C}$ and N$_{1A'}$ . . . N$_{1B}$ distances by ca. 0.15 Å relative to those in free 1, although it is not sufficient to allow for a linear alignment of the three hydrogen bonding atoms (N$_{pyrrole}$—H . . . O$_{MeOH}$=152.1(4)°). Crystal data for 1.2(MeOH): yellow prisms from CH$_2$Cl$_2$—MeOH, tetragonal space group I$\bar{4}$, Z=2, a=10.383(2) Å, b=10.383(2) Å, c=13.232(5) Å, V=1426.6(6) Å$^3$, $\rho_{calc}$=1.15 g cm$^{-1}$, F(000)= 536. Final R=0.0787, R$_w$=0.205, GOF=1.099 for 84 parameters. The NH proton of 1.2(MeOH) was calculated in an idealized postion (N—H=0.90 Å) with U$_{iso}$ set to 1.2 U$_{eq}$ for the attached N atom.

Crystal complexes of calixpyrrole 1 and dimethylsulfoxide ("1.(DMSO)") have also been studied by X-ray crystal lography. The crystals also undergo a phase change as they are cooled, at room temperature there is one crystallographically distinct calixpyrrole in the unit cell, at −75° C. there are two. In both phases the calixpyrrole adopts a 1,3-alternate conformation wherein a DMSO molecule is hydrogen bonded to one pyrrole NH group (at low temperature N . . . O=2.962, 2.985 Å; H . . . O=2.089, 2.024 Å and N—H . . . O=176.2° and 174.5° and at room temperature N . . . O=2.996 Å, H . . . O=2.099 Å and N—H . . . O=174.5°). Crystallographic data for 1.(DMSO): There are two crystallographic modifications of 1.(DMSO). The room temperature modification is monoclinic, $P2_1/c$, Z=4, in a cell of dimensions: a=10.423(2), b=23.599(6), c=12.480(2) Å, β=107.72(1)°, V=2924(1) Å$^3$, $\rho_{calc}$=1.15 g cm$^{-3}$, F(000)= 1096. 6720 unique reflections, 2161 with $F_0$>4(σ($F_0$)). The final R(F)=0.0866, Rw(F$^2$)=0.253, goodness of fit=0.981 for 335 parameters refined on F$^2$. The low-temperature modification (−75° C.) is triclinic, $P\overline{1}$, Z=4, in a cell of dimensions: a=10.362(3), b=12.373(7), c=23.468(10) Å, α=89.77 (4), β=88.35(3), γ=72.36(4)°, V=2866(2) Å$^3$, $\rho_{calc}$=1.17 g cm$^{-3}$, F(000)=1096. 10061 unique reflections, 5213 with $F_0$>4(σ($F_0$)). The final R(F)=0.0819, Rw(F$^2$)=0.212, goodness of fit=1.075 for 700 parameters refined on F$^2$.

Figure 3A:
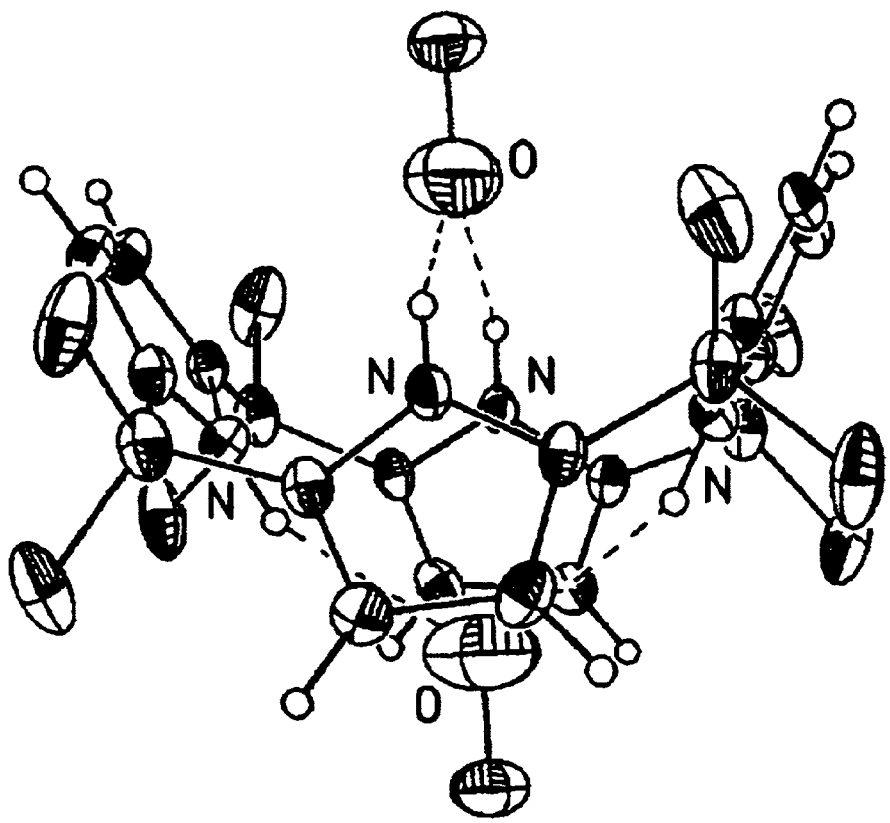
FIG. 3A illustrates the X-ray crystal structure of meso-octamethylcalix[4]pyrrole bis-methanol complex, 1.2 MeOH. The meso-octamethylcalix[4]pyrrole adopts a 1,3-alternate conformation wherein two NH groups bind to each methanol. Thermal ellipsoids are at the 30% probability level.
Figure 3B:
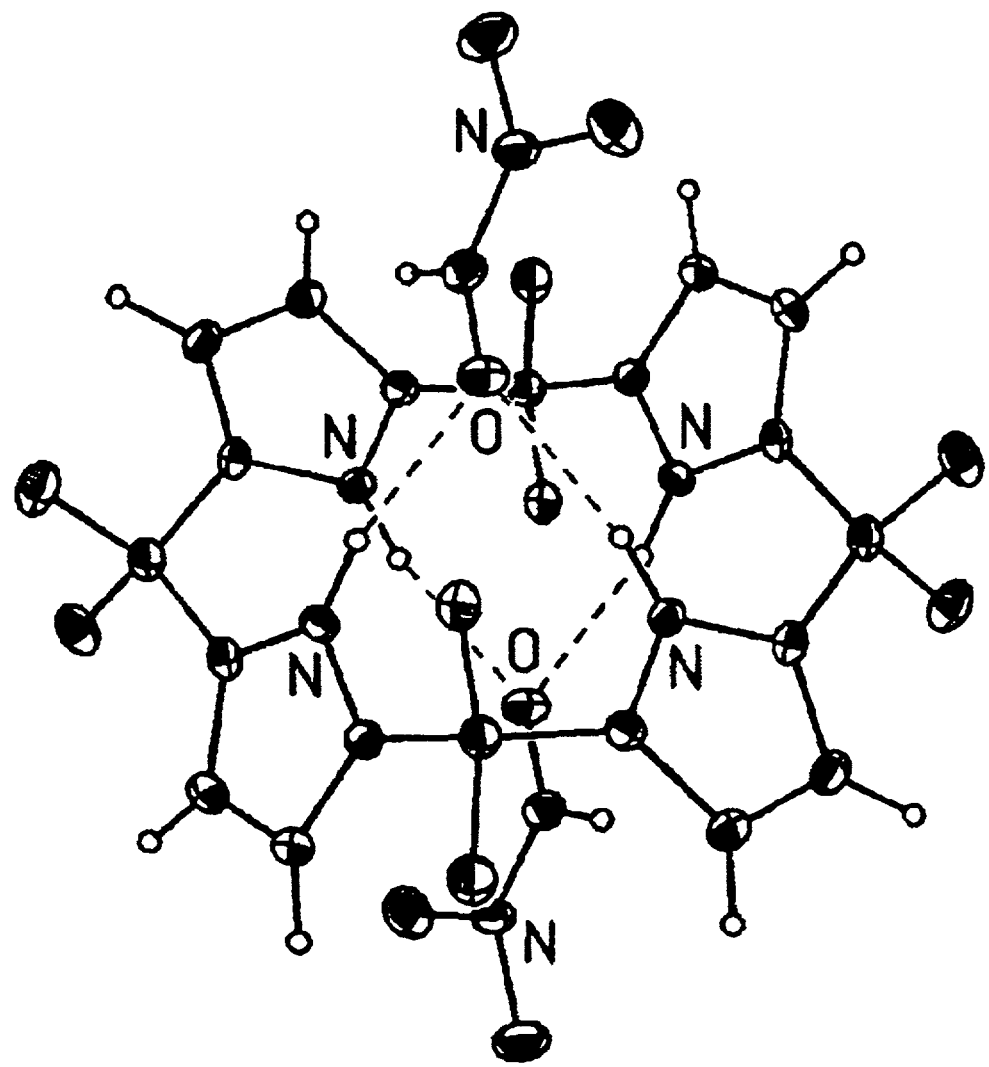
FIG. 3B illustrates the X-ray crystal structure of meso-octamethylcalix[4]pyrrole bis-dimethylformamide complex, 1.2 DMF. The meso-octamethylcalix[4]pyrrole adopts a 1,2-alternate conformation wherein two NH groups bind to each dimethylformamide. Thermal ellipsoids are at the 30% probability level.
Figure 3C:
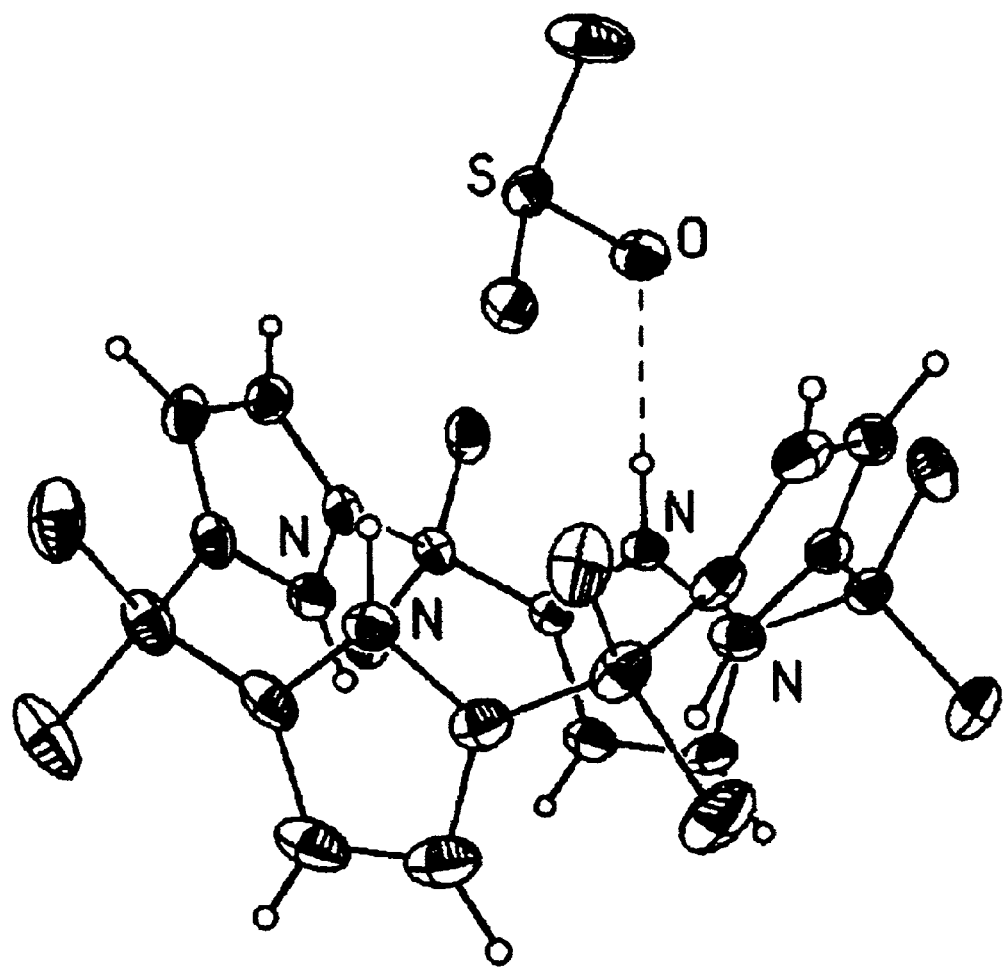
FIG. 3C illustrates the X-ray crystal structure of meso-octamethylcalix[4]pyrrole dimethylsulfoxide complex, 1.DMSO. The meso-octamethylcalix[4]pyrrole adopts a 1,3-alternate conformation wherein one NH group binds to a dimethylsulfoxide. Thermal ellipsoids are at the 30% probability level.

The complex of calix[4]pyrrole 1 and N,N-dimethylformamide ("1.2(DMF)") indicates that individual symmetry-equivalent guests are found above and below the host, and that each amide is hydrogen bonded to adjacent pyrroles (FIG. 3B). The conformation of the calixpyrrole is therefore 1,2-alternate. To the present inventors' knowledge, 1.2(DMF) is the first calixpyrrole in this conformation to be unambiguously characterized. The complexes of 1.2 (CH$_3$OH) (FIG. 3A) and 1.(DMSO) (FIG. 3C) both adopt the 1,3-alternate conformation in the solid state. However in the case of 1.2(CH$_3$OH) all the pyrrole NH groups are involved in hydrogen bonding, whereas in the case of 1.(DMSO) only one pyrrolic NH group hydrogen bonds to the calixpyrrole.

While cone, 1,3-alternate, 1,2-alternate and partial cone conformations for calixpyrrole macrocycles have been proposed previously, the present studies provide the first demonstration of the crystalline forms of anion-complexed molecules. Solution phase data are provided in Example 10.

EXAMPLE 2

Novel meso-Substituted Calix[4]pyrrole Macrocycles

The present example provides meso-substituted calix[4] pyrrole macrocycles that have not previously been known. In particular, calix[4]pyrrole macrocycles having functional groups for further derivatization have proved particularly useful as provided for in later examples.

Calix[4]pyrrole meso-monoester 3. 4-Acetylbutyric acid (3.8 g, 29 mmol) was dissolved in methanol (50 mL) in a 100 mL round bottomed flask with magnetic stirring. Concentrated hydrochloric acid (1 mL, 37%) was added and the mixture heated at reflux for 12 hr. The solvent was then removed in vacuo and the residue redissolved in dichloromethane (50 mL). The solution was then washed with saturated NaHCO$_3$ (aq) solution (2×50 mL) and then brine (1×100 mL). The organic layer was separated and then dried over MgSO$_4$ and reduced in vacuo to give the methyl ester, methyl-4-acetylbutyrate, as a yellow oil (3.5 g, 24.3 mmol) corresponding to a yield of 84%. $^1$H NMR (CDCl$_3$) 3.64 (s, 3, OCH$_3$), 2.49 (t, J=7.2 Hz, 2, CH$_2$), 2.32 (t, J =7.2 Hz, 2, CH$_2$), 2.12 (s, 3, CH$_3$), 1.86 (m, 2, CH$_2$). $^{13}$C NMR (CDCl$_3$) 207.0, 172.8, 50.7, 41.7, 32.3, 29.1, 18.25. CI MS m/z @ 145 (MH$^+$)

Methyl-4-acetylbutyrate (0.80 g, 5.6 mmol) was dissolved in methanol (50 mL) in a 100 mL round bottomed flask. Cyclohexanone (0.55 g, 5.6 mmol) and pyrrole (0.75 g, 11.1 mmol) were added and the mixture cooled in an ice bath to 0° C. The flask was fitted with a reflux condenser and magnetically stirred. Methanesulfonic acid (20 drops) was added dropwise over the course of five minutes, and the mixture was stirred at 0° C. for 1 hr, and then at room temperature overnight. The solvent was removed in vacuo. FAB mass spectrocopic analysis showed the presence of mono-, di-, tri- and tetrahook material in the crude reaction mixture as well as tetraspirocyclohexylcalix[4]pyrrole. The residue was purified by column chromatography on silica gel using dichloromethane as eluant. This yielded the monohook calixpyrrole methyl ester 3 as a white powder (211 mg, 0.33 mmol) corresponding to a yield of 11.8%. $^1$H NMR (CDCl$_3$) 7.07 (br. m, 4, NH), 5.88 (m, 8, CH(py)), 3.63 (s, 3, OCH$_3$), 2.22 (t, J=7.2 Hz, 2, CH$_2$), 1.93 (v. br., 14, 6CH$_{2(cyclohexyl)}$+CH$_{2(hook)}$) 1.56–1.35 (v. br., 23, CH$_{2(hook)}$+ 9CH$_{2(cyclohexyl)}$+CCH$_3$). $^{13}$C NMR (CDCl$_3$) 173.8, 137.169, 136.5, 136.3, 130.7, 103.6, 103.5, 103.2, 53.4, 51.37, 39.7, 39.5, 39.4, 38.5, 37.5, 37.2, 36.9, 36.8, 34.0, 26.1, 25.9, 22.75, 22.70, 19.9. CI MS m/z @ 635 (MH$^+$). High Resolution Mass Spectrum: Mass=634.4236 mDa 1.1 ppm 1.8 Calc. mass 634.4247 DBE 17.0 C$_{41}$H$_{54}$N$_4$O$_2$.

3

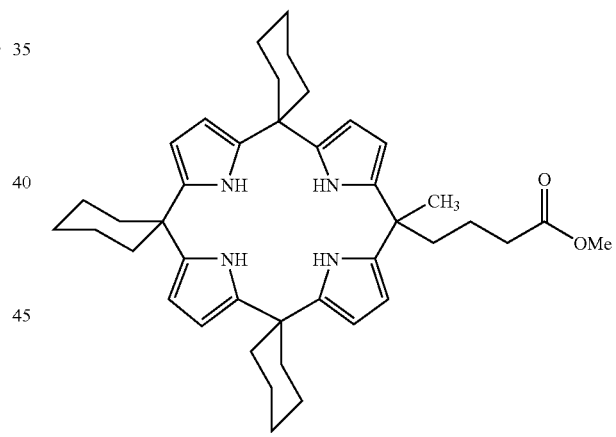

Calix[4]pyrrole meso-monoacid 4. The calixpyrrole methyl ester (211 mg, 0.33 mmol) (compound 3) was dissolved in 20 mL ethanol in a 100 mL round bottomed flask with magnetic stirring. The flask was fitted with a reflux condenser and the solution heated to reflux. An aqueous solution of sodium hydroxide (20 mL, 2.0 M) was added and the mixture heated at reflux for 4 hr. The solution was then allowed to cool and the ethanol present in solution was removed in vacuo. The remaining aqueous solution was acidified to pH 1 with perchloric acid (70%). The product was then extracted from this aqueous phase with dichloromethane (50 mL). The dichloromethane layer was washed with water (100 mL) and dried over MgSO$_4$. Removal of the solvent afforded the "monohook" calixpyrrole acid 3 as an off-white powder (187 mg, 0.30 mmol) corresponding to a yield of 90.6%. $^1$H NMR (CDCl$_3$) 7.02 (br. m, 4, NH), 5.89

(m, 8, CH$_{(py)}$), 2.26 (t, 2, CH$_2$), 1.91 (br., 14, 6CH$_{2(cyclohexyl)}$+CH$_{2(hook)}$), 1.44 (br. m., 24, 9CH$_{2(cyclohexyl)}$+CH$_{2(hook)}$+CCH$_3$)+0.5H$_2$O) $^{13}$C NMR (CDCl$_3$) 179.4, 137.3, 136.6, 136.2, 103.7, 103.6, 103.5, 103.2, 53.4, 39.7, 39.4, 39.3, 38.5, 37.4, 37.2, 36.9, 36.8, 33.8, 26.0, 25.9, 22.7, 22.6, 19.5. FAB MS m/z @ 620 (MH$^+$). High Resolution Mass Spectrum: Mass=620.4073 mDa 1.7 ppm 2.8 Calc. mass 620.4090 DBE 17.0 C$_{40}$H$_{52}$N$_4$O$_2$.

4

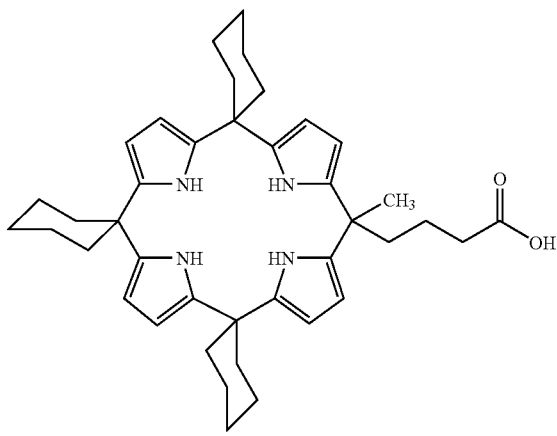

Figure 4:
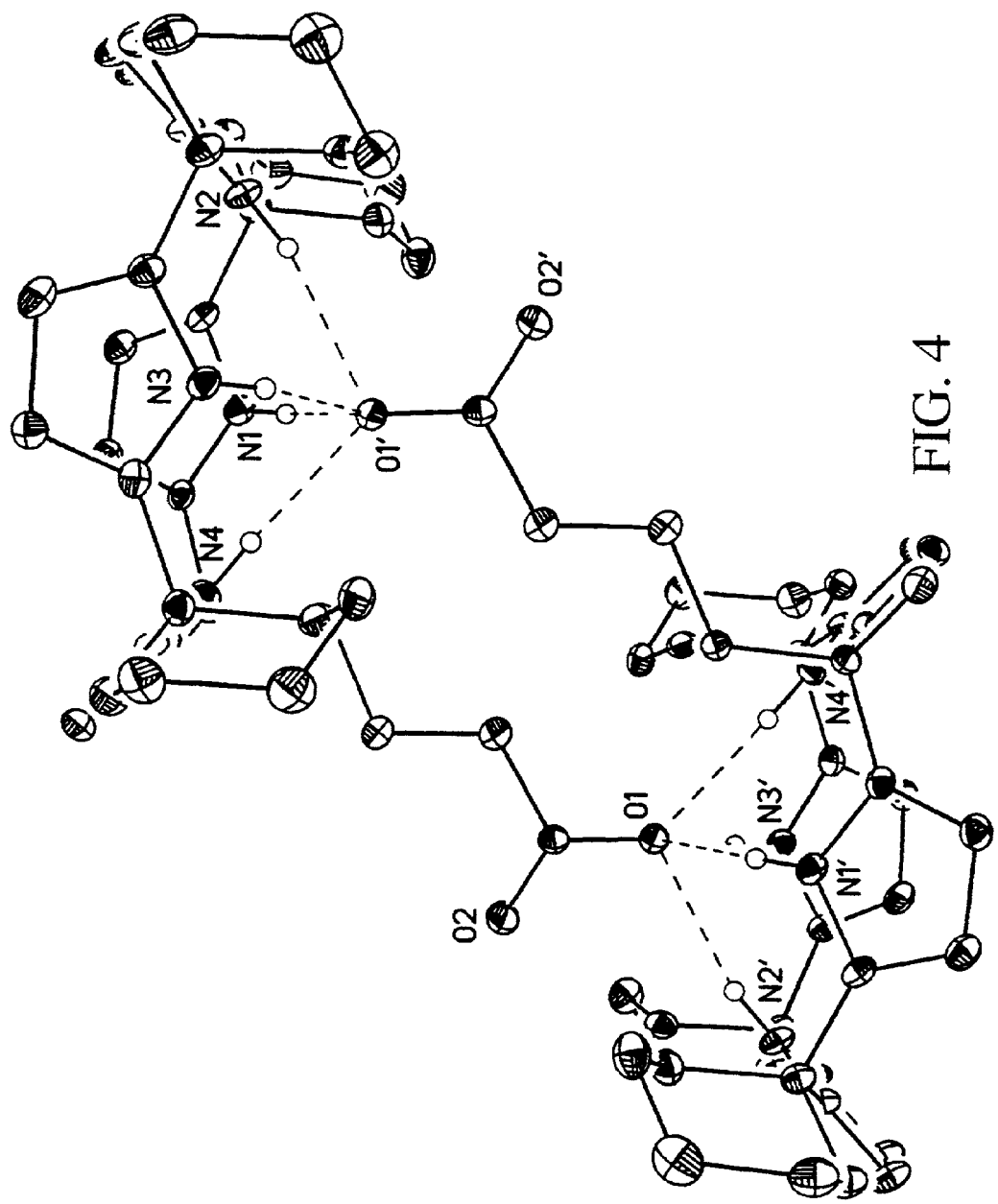
FIG. 4 illustrates the X-ray crystal structure of tetrabutylammonium salt of calix[4]pyrrole, 4. Calix[4]pyrrole anions self-assemble in the solid state forming dimers. Thermal ellipsoids are at the 30% probability level. Counter cations are omitted for clarity.

X-ray quality crystals of the tetrabutylammonium salt of calix[4]pyrrole carboxylate 4 were obtained by slow evaporation of a dichloromethane solution of 4 in the presence of excess tetrabutylammonium fluoride trihydrate. The resulting crystal structure demonstrated that this anionic calix[4]pyrrole self-assembles into dimers in the solid state forming a cyclic structure. The carboxylate moiety is hydrogen bonded to the pyrrole array of an adjacent calix[4]pyrrole (FIG. 4). Therefore the calix[4]pyrrole 4 adopts a cone conformation in the dimer. The separation between the root mean square planes of the nitrogen atoms in each macrocycle is 7.41(1) Å. Crystallographic summary for (C$_{40}$H$_{51}$N$_4$O$_2$)$^{1-}$(C$_{16}$H$_{36}$N)$^{1+}$·2CH$_2$Cl$_2$, colorless needles were grown from CH$_2$Cl$_2$, triclinic, P$\bar{1}$, Z=2 in a cell of dimensions: a=12.682(2), b=13.127(2), c=17.871(2) Å, α=99.913(9), β=90.527(9), γ=98.49(1)°, V=2896.7(6) Å$^3$, ρ$_{calc}$=1.18 g cm$^{-3}$, F(000)=1116. A total of 11364 reflections were measured, 10078 unique (R$_{int}$=0.044) on a Siemens P4 diffractometer using graphite monochromatized Mo Kα radiation (λ=0.71073 Å). The structure was refined on F$^2$ to an R$_w$=0.220, with a conventional R=0.084, with a goodness of fit=1.031 for 661 refined parameters. The geometry of the interaction is: N1-H1N . . . O1 (related by 1-x, 1-y, 1-z), N . . . O 2.975(5) Å, H . . . O 2.19(4) Å, N—H . . . O 162(4)°; N2-H2N . . . O1, N . . . O 2.980(5) Å, H . . . O2.18(5) Å, N—H . . . O 167(4) °; N3-H3N . . . O1, N . . . O 2.950(5) Å, H . . . O2.14(4) Å, N—H . . . O 163(4)0; N4-H4N . . . O1, N . . . O 2.916(5) Å, H . . . O 2.09(4) Å, N—H . . . O 176(4)°.

"Monohook" acid 4 is particularly useful as a synthon for the production of calix[4]pyrrole derivatives, conjugates, modified silica gels and the like. Additionally the present inventors expect that compound 4 may be used as a zwitterion binding agent as cations may coordinate to the carboxylate functionality and anions to the calixpyrrole core.

Tetravinylcalix[4]pyrrole 5. Pyrrole (0.745 g, 11.12 mmol) and 5-hexan-2-one (1.09 g, 11.12 mmol) were dissolved in methanol (100 mL). Methanesulfonic acid (0.5 mL) was added and the reaction was stirred in the dark for 12 hr. The solvent was then removed in vacuo and the reaction mixture was purified by column chromatography on silica gel using dichloromethane as eluant. The first fraction from the column was collected and, upon removal of the solvent, afforded a colorless oil (1.05 g, 64% yield).

The product 5 is a mixture of conformers of tetravinylcalix[4]pyrrole where the groups in the meso-positions are each in one of two orientations, with the bulkier alkene group either above or below the plane of the meso-carbon atoms (see Example 7). $^1$H NMR (CDCl$_3$): 7.02 (br. s, 4H, NH), 5.91 (m. 8H, CH$_{(pyrrole)}$) 5.71 (m, 4H, =CH—), 4.90 (m, 8H, =CH$_2$), 2.22 (br. m., 16H, CH$_2$CH$_2$). $^{13}$C NMR (CD$_2$C$_2$): (139.4, 139.3, 139.2), (137.83, 137.80, 137.70, 137.63, 137.58), (114.5, 114.4, 114.35), (104.4, 104.3, 104.26, 104.2, 104.1, 104.0), (40.02, 39.98), (39.2, 39.0), 29.2, (26.45, 26.43, 26.23, 26.15, 26.04, 25.97).

5

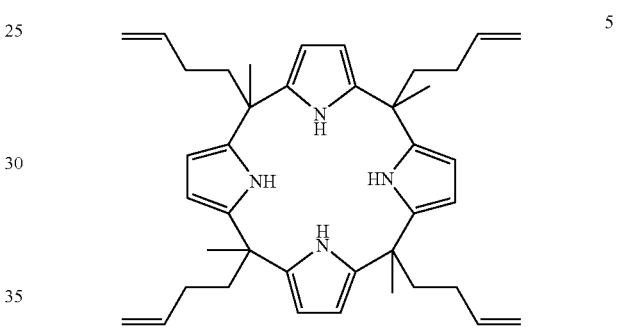

Calix[4]pyrrole 5 may prove to be particularly useful as a monomer for use in the synthesis of calixpyrrole polymer materials. A known method uses pyrrole, a C$_4$–C$_6$ saturated alicyclic ketone and an acid containing vinyl groups or triple bonds to form a polymerized resin. In this case, the resulting products are undefined since it appears to be unknown where the modifying group is attached to the product. In contrast, the present method allows synthesis of monomer 5 which can then be subjected to polymerization. This method of forming a defined calix[n]pyrrole polymer is applicable for n=4–8.

Meso-octabenzylcalix[4]pyrrole 6. Pyrrole (0.745 g, 11.12 mmol) and 1,3-diphenylacetone (2.34 g, 11.12 mmol) were dissolved in methanol (250 mL). Methanesulfonic acid (0.5 mL) was added and the reaction was stirred in the dark for twelve hours. The solvent was then removed in vacuo and the reaction mixture was purified by column chromatography. The first fraction from the column was collected and, upon removal of the solvent, afforded a yellow oil. Acetone (10 mL) was added and the flask was swirled in order to dissolve the oil. After 20 min, white crystals of the meso-octabenzylcalix[4]pyrrole 6 (278 mg, 9.6% yield) had formed; they were collected and dried. $^1$H NMR (CDCl$_3$): 7.19 (m, 24H, ArH), 6.83 (m, 16H, ArH), 6.22 (br. s. 4H, NH), 5.62 (d, 8H, CH$_{(pyrrole)}$), 2.90 (m, 16H, ArCH$_2$. $^{13}$C NMR (CDCl$_3$): 138.3, 134.1, 130.9, 127.7, 126.4, 106.5, 44.7. High Resolution negative FAB calc. for C$_{76}$H$_{67}$N$_4$ (1035.53674) found 1035.4720 (1.8 ppm).

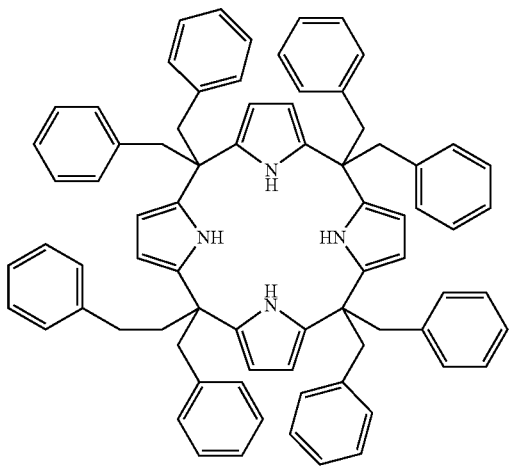

6

Figure 5:
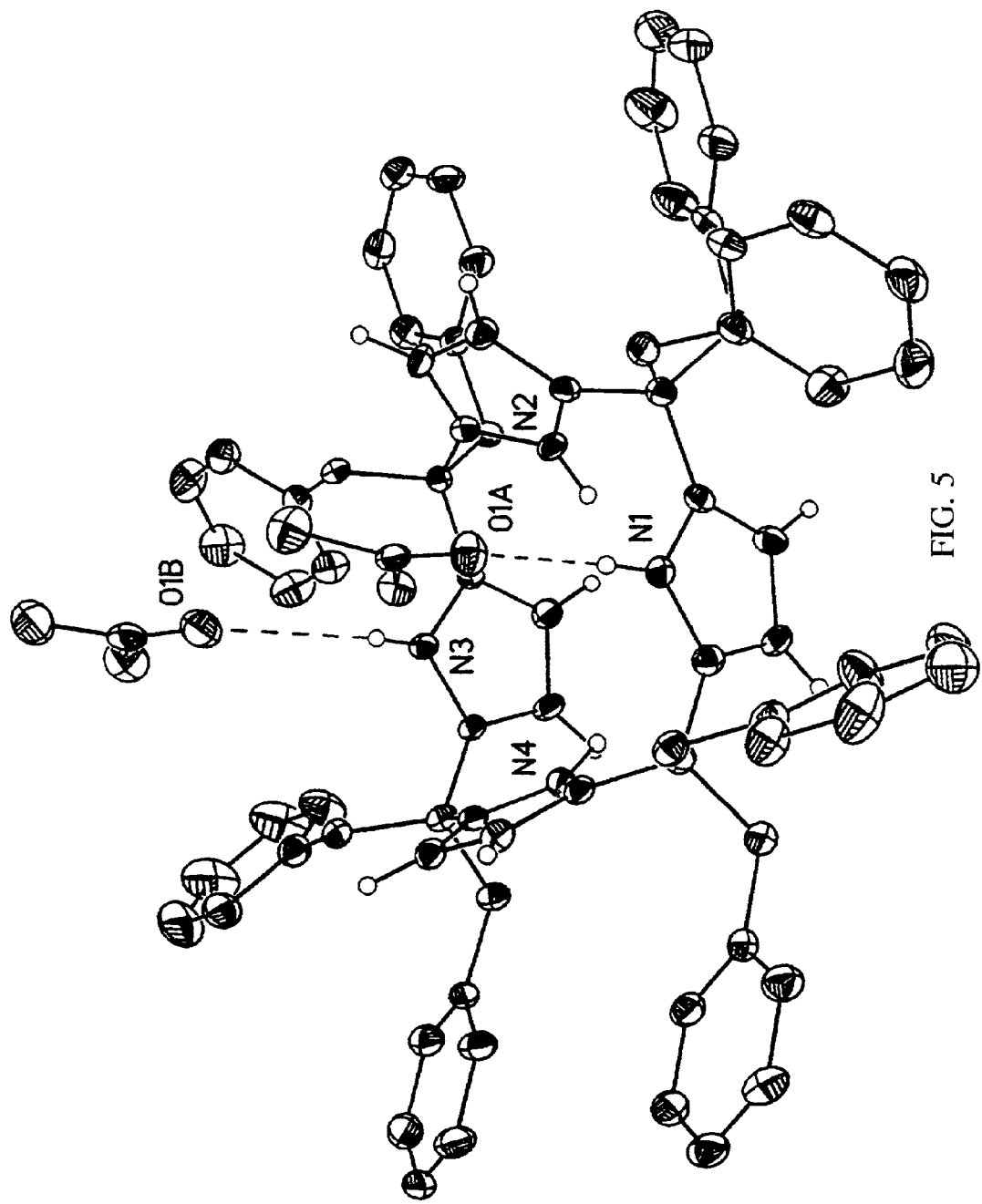
FIG. 5 illustrates the X-ray crystal structure of a meso-octabenzylcalix[4]pyrrole acetone complex, 6.3(acetone). The octabenzylcalix[4]pyrrole adopts a 1,3-alternate conformation wherein one NH group binds to an acetone. An unbound acetone molecule in the crystal lattice is omitted for clarity. Thermal ellipsoids are at the 30% probability level.

Crystals of octabenzylcalix[4]pyrrole 6 suitable for X-ray study were grown from acetone. The conformation of the macrocycle in 6.2(acetone).acetone$_{lattice}$ is 1,3-alternate (as in 1.2(MeOH)), but the two acetone guests are both located on the same face of the ligand, held in place by single H-bonds (FIG. 5). One of the acetone moieties lies much closer to the macrocycle than the other ($N_{pyrrole}$ . . . $O_{acetone}$=2.972(6) Å vs. 3.359(6) Å), reflecting an almost colinear (177(5)°) arrangement of $N_{pyrrole}$-H . . . $O_{acetone}$ atoms in the former case. By contrast, the N—H . . . O angle formed with the more distant ketone measures 159(4)°. Octabenzylcalix[4]pyrrole may prove useful as a phase transfer catalyst for anions, or as a starting material for the synthesis of calix[4]pyrrole aryl-transition metal complexes which could be used as catalysts for various reactions or as a sensor for anions. This material is also a potential precursor to pyridine-containing systems (Example 6).

meso-Tetraspirotetrahydrothiopyrancalix[4]pyrrole 7. Tetrahydrothiopyran-4-one (0.50 g, 4.3 mmol) and pyrrole (0.288 g, 4.3 mmol) were dissolved in ethanol (30 mL) and 10 drops of methanesulfonic acid were added. The mixture was stirred for 12 hours in the dark, after which time a white precipitate had formed. The solvent was removed in vacuo and the residue purifed by column chromatography (SiO$_2$, CH$_2$Cl$_2$ eluant) affording the tetra sulfide macrocycle as a white powder (540 mg, 76 % yield). $^1$H NMR (250 MHz, CD$_2$Cl$_2$) δ: 7.10 (s, 4H, NH), 5.97 (m, 8H, CH$_{pyrrole}$), 2.61 (m, 12H, CH$_{pyran}$) 2.28 (m, 12H, CH$_{pyran}$). $^{13}$C NMR (62.90 MHz. CD$_2$Cl$_2$) δ: 136.0, 105.0, 39.5, 37.9, 24.9. High resolution FABMS calc for C$_{36}$H$_{44}$N$_4$S$_4$ 660.2449; found 660.2437 (Δ1.7 ppm).

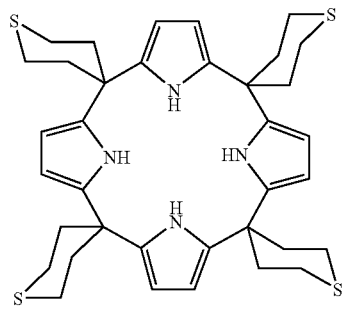

7

Figure 6:
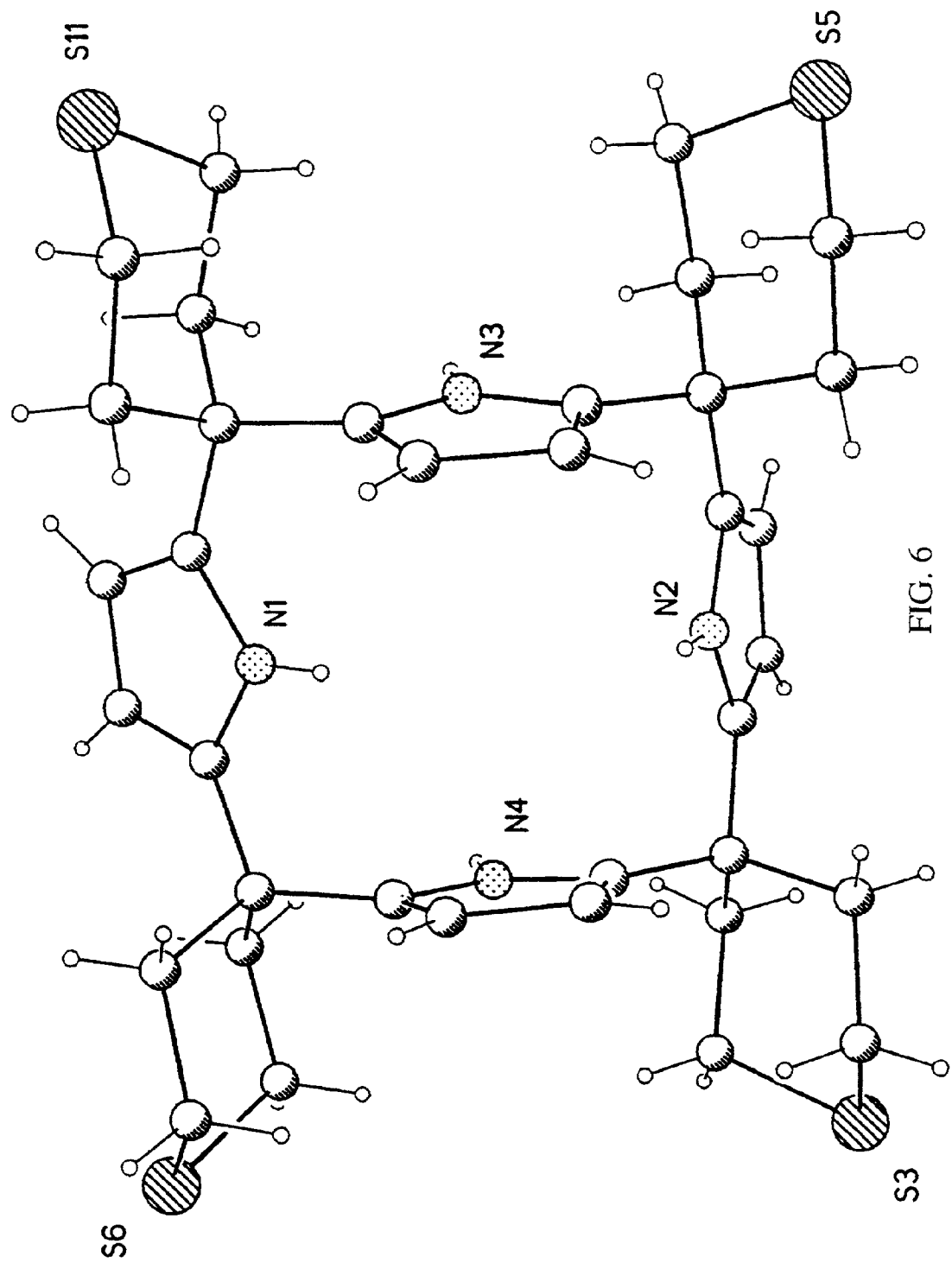
FIG. 6 illustrates the X-ray crystal structure of meso-tetrakis-tetrahydrothiopyranyl-calix[4]pyrrole, 7, adopting a 1,3-alternate conformation. Thermal ellipsoids are at the 30% probability level.

Crystals of macrocycle 7 suitable for analysis by X-ray diffraction techniques were grown by slow evaporation of a dichloromethane solution of the macrocycle (FIG. 6). Crystallographic data for 7: Colorless crystals, triclinic, P$\bar{1}$, Z=2, in a cell of dimensions: a=11.059(2), b=15.023(3), c=15.874 (3) Å, α=112.21(1), β=102.64(1), γ=103.07(2)°, V=2238.9 (7)Å$^3$, ρ$_{calc}$=1.42 g cm$^{-3}$, F(000)=998. 3987 unique reflections, 2991 with F$_0$>4(σ(F$_0$)). The final R(F)=0.0545, Rw(F$^2$)=0.126, goodness of fit=1.133 for 336 parameters refined on F$^2$. Calix[4]pyrrole 7 is a useful synthon for the synthesis of transition metal complexes on the periphery of the calixpyrrole which complexes are contemplated to be useful as sensors. Oxidation of macrocycle sulfide groups to sulfoxide or sulfone introduces further polarity into the macrocycle and renders it more water soluble, thus allowing use in biomedical applications (see Example 11). Additionally, the present inventors envision that analogous macrocycles containing NH, NH$_2^+$, NHCH$_3^+$, N(CH$_3$)$_2^+$, NOH, NNH$_2$ and NN(CH$_3$)$_2$ functionalities instead of sulfur will be water soluble.

meso-Octanonylcalix[4]pyrrole 8. 10-Nonadecanone (3.14 g, 11.12 mmol) and pyrrole (0.745 g, 11.12 mmol) were dissolved in a mixture of ethanol (100 mL) and dichloromethane (50 mL). Methanesulfonic acid (20 drops) was added and the mixture was stirred for 12 hours. The solvent was then removed in vacuo and the product was purified by column chromatography on silica gel (hexane eluant) affording the product as a white powder (650 mg, 17% yield). $^1$H NMR (250 MHz, CDCl$_3$) δ: 6.99 (s, 4H, NH), 5.86 (s, 8H, CH), [1.77, 1.54, 1.21, 0.86 (br. multiplets, 152H, CH$_2$,CH$_3$). $^{13}$C NMR (62.90 MHz, CDCl$_3$) δ: 136.2, 104.6, 42.4, 37.7, 31.9, 30.3, 29.78, 29.75, 29.4, 24.0, 22.7, 14.1. High resolution FABMS calc for C$_{92}$H$_{165}$N$_4$ 1326.3034; found 1326.3015 (Δ1.4 ppm).

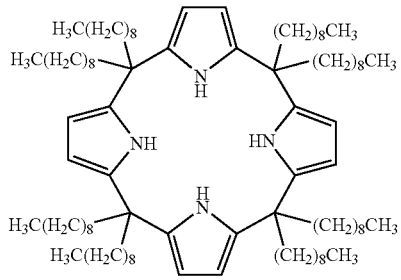

8

Due to hydrophobic alkyl groups, calixpyrrole 8 is designed to have particular affinity for lipid bilayer membranes and is expected to serve as an insertion agent, i.e. insertion of macrocycle 8 is expected to allow passage of charged species (such as phosphorylated anti-viral agents) through cell membranes, thereby increasing the effectiveness of the agent (Example 11).

meso-Tetramethyl-mesotetraferrocenylcalix[4]pyrrole 9. Pyrrole (0.373 g, 5.56 mmol) and acetylferrocene (1.27 g, 5.56 mmol) were dissolved in methanol (50 mL) and stirred. Methanesulfonic acid (20 drops) was added and the reaction stirred for twelve hours. Triethylamine (30 drops) was then added to the reaction mixture followed by aspartic acid (2 g) and the solvent removed in vacuo. The residue was purified by column chromatography (silica gel, CH$_2$ Cl$_2$ eluant) yielding the product as a yellow foam (390 mg, 25% yield). 1 H NMR (CD$_2$ Cl$_2$) 1.801–1.997 ppm (12H, m, CH$_3$), 3.931–4.198 ppm (36H, m, C$_{10}$ H$_{9(ferrocene)}$), 5.625–5.927 (8H, m), 7.929 (s, 4H, NH). $^{13}$C NMR (CD$_2$ Cl$_2$) 28.958, 31.016, 39.841, 39.857, 67.343, 67.525, 67.818, 69.031, 69.141, 69.356, 98.224, 104.588, 104, 932, 105.814, 136.866, 137.348, 137.482, 137.572

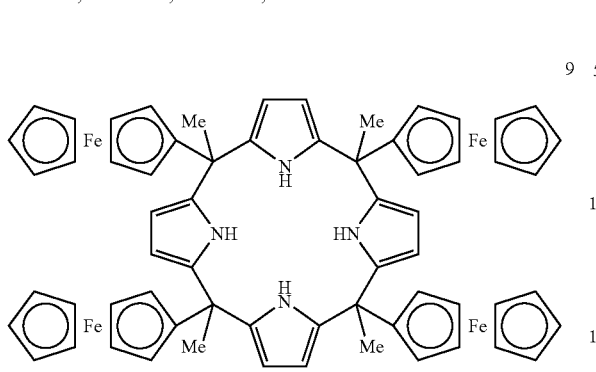

Calix[4]pyrrole 9 can be used as a reporter molecule or sensor for detecting anions or neutral molecules. The complexation of an anion in the calixpyrrole core will perturb the electronic states of the ferrocene moieties, thereby causing a shift in the ferrocene redox potential which can be detected by electrochemical techniques, including, but not limited to, cyclic volatmmetry and Osteryoung-type square wave voltammetry.

While the present example demonstrates ester (3), acid (4), alkenyl (5), aryl (6), sulfide (7), and alkyl (8) substituents for calix[4]pyrroles, one of skill in the art would be able to synthesize further meso-substituted calix[4]pyrrole macrocycles in light of the teachings herein and using standard organic chemical synthesis reactions as described herein.

EXAMPLE 3

Novel β-Substituted Calix[4]pyrrole Macrocycles

Calix[4]pyrrole macrocycles with functional groups in the 5-position (i.e., on the β-carbon of a pyrrole ring), and the syntheses thereof, are provided in the present example. Such β-substituted calixpyrroles may have substitution at one or more of the β-positions. To prepare such compounds of the present invention, either meso-octamethylcalix[4]pyrrole 1 is deprotonated and the substituent to be added at the β-position is then reacted with the activated calixpyrrole, or the calixpyrrole is synthesized from a β-substituted pyrrole.

Initially, sodium hydride was tried as a base to deprotonate the calixpyrrole. Sodium hydride was added to a solution of the macrocycle in DMF, after which bromoethylacetate was added in order to introduce an ester functionality to the calixpyrrole. However, this produced no reaction.

A stronger base (n-BuLi) was then tried; 4 equivalents of the base were added dropwise to a THF solution of the macrocycle at −78° C. under an argon atmosphere. After 2 hours stirring at −78° C., 4 equivalents of bromoethylacetate were added and the solution was allowed to warm up to room temperature over 90 minutes. The THF was then removed in vacuo and the residue was purified using column chromatography on silica gel by eluting with $CH_2Cl_2$. Several fractions were isolated from the column. The first proved to be unreacted calix[4]pyrrole. The second was the β-monosubstituted ester 10 and the third, the β-diester 11.

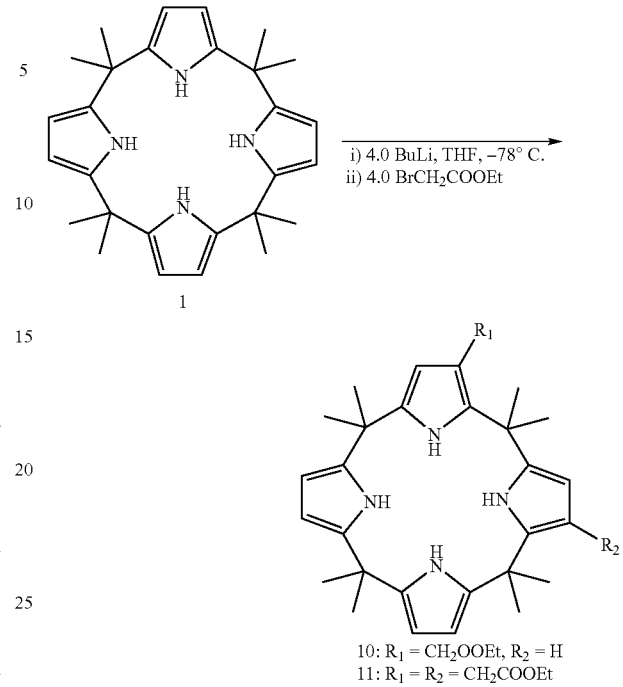

10: $R_1$ = $CH_2OOEt$, $R_2$ = H
11: $R_1$ = $R_2$ = $CH_2COOEt$

Calix[4]pyrrole β-mono- and disubstituted ester 10 and 11. meso-Octamethylcalix[4]pyrrole (1.0 g, 2.34 mmol; preparation described in Example 1) was dissolved with stirring in THF (100 mL, dry) under an argon atmosphere. The solution was cooled to −78° C. using a $CO_2$/acetone bath, n-Butyllithium (5.83 mL, 9.34 mmol, 1.6 M in hexane) was added to the solution dropwise. After 2 hours, ethylbromoacetate (1.95 g, 11.68 mmol) was added dropwise to the solution. The reaction was then removed from the $CO_2$ bath and allowed to warm to room temperature. After 90 minutes, the solvent was removed in vacuo and EtOH (100 mL) was added to the flask. Water (100 mL) was slowly added with swirling, causing a white precipitate to form. The precipitate was collected by filtration, dried under high vacuum and then purified by column chromatography on silica gel eluting with $CH_2Cl_2$. The monoester 10 (310 mg, 26%) and diester 11 (40 mg, 2.8%) were the second and third main products to be eluted from the column. Mono-ester 10: $^1$H NMR (500 MHz, $CD_2Cl_2$) δ: 8.55 (s, 1H, NH), 7.15 (s, 1H, NH), 7.04 (s, 1H, NH), 7.00 (s, 1H, NH), 5.94–5.88 (overlapping multiplets, 5H, $CH_{py}$), 5.83 (m, 1H, $CH_{py}$), 5.72 (m, 1H, $CH_{py}$), 4.24 (q, J=7.15 Hz, 2H, $CH_2CH_3$), 3.65 (s, 2H, $CCH_2$), 1.62–1.47 (overlapping singlets, 24H, $CCH_3$), 1.33 (t, 3H, J=7.15 Hz). $^{13}$C (DEPT) NMR (500 MHz, $CD_2Cl_2$) δ: 174.93 (C=O), 140.42 ($C_{py}$), 139.69 ($C_{py}$), 139.31 ($C_{py}$), 138.92 ($C_{py}$), 138.50 ($C_{py}$), 137.98 ($C_{py}$), 137.20 ($C_{py}$), 134.06 ($C_{py}$), 109.95 ($CH_{py}$), 107.07 ($CCH_2COOEt$), 103.41 ($CH_{py}$), 103.10 ($CH_{py}$), 102.90 ($CH_{py}$), 102.66 ($CH_{py}$), 101.37 ($CH_{py}$), 61.40 ($CH_2CH_3$), 37.16 ($CCH_3$), 35.50 ($CCH_3$), 35.43 ($CCH_2$), 35.17 ($CCH_3$), 33.95 ($CCH_3$), 29.20 ($CCH_3$), 29.05 ($CCH_3$), 28.90 ($CCH_3$), 28.68 ($CCH_3$), 14.47 ($CH_2CH_3$). High resolution FABMS calc for $C_{32}H_{42}N_4O_2$ 514.3308; found 514.3302 (Δ1.2 ppm) Bis-ester 11: $^1$H NMR (500 MHz, $CD_2Cl_2$) δ: 8.61 (s, 1H, NH), 8.52 (s, 1H, NH), 7.20 (s, 1H, NH), 7.00 (s, 1H, NH), 5.85–5.54 (several multiplets—overlapping, 4H, $CH_{py}$), 5.63 (d, 1H, $CH_{py}$), 5.55 (d, 1H, $CH_{py}$), 4.19 (m, 4H, CH$_2$CH$_3$), 3.60 and 3.59 (two singlets, total 4H, CCH$_2$), 1.58 (s, 6H, CCH$_3$), 1.52 (s, 6H, CCH$_3$), 1.49 (s, 6H, CCH$_3$), 1.44 (s. 6H, CCH$_3$), 1.29 (t, 2H, CH$_2$CH$_3$), 1.27 (t, 2H, CH$_2$CH$_3$). $^{13}$C (DEPT) NMR (500 MHz, CD$_2$Cl$_2$) δ: 175.51 (C=O), 175.21 (C=O), 141.21 (C$_{py}$), 140.36 (C$_{py}$), 138.98 (C$_{py}$), 137.94, (C$_{py}$) 137.70, (C$_{py}$) 137.68 (C$_{py}$), 134.3 (C$_{py}$), 133.89 (C$_{py}$), 109.64 (C$_{py}$CH$_2$), 109.09 (C$_{py}$CH$_2$), 106.73 (CH$_{py}$), 105.08 (CH$_{py}$), 103.23 (CH$_{py}$), 102.90 (CH$_{py}$), 101.93 (CH$_{py}$), 100.72 (CH$_{py}$), 61.42 (CH$_2$CH$_3$), 37.21 (CCH$_3$), 36.89 (CCH$_3$), 35.52 (CCH$_3$), 35.19 (CCH$_3$), 33.97 (CCH$_2$), 33.93 (CCH$_2$), 29.05 (CCH$_3$), 28.90 (CCH$_3$), 14.41 (CH$_2$CH$_3$). High resolution FABMS calc for C$_{36}$H$_{48}$N$_4$O$_4$ 600.3676; found 600.3663 (Δ2.1 ppm). This reaction may also be accomplished using other bases including but not limited to alkyllithium or alkyllithium or in the presence of a coordinating ligand such as but not limited to tetramethylethylenediamine with an aryllithium or alkyllithium base. Alternately other electrophiles may be attached to the activated calixpyrrole macrocycle (e.g. CO$_2$, ethylchloroformate, acrylonitrile). β-Substituted calix[4]pyrrole esters are useful as a reagent for the synthesis of other calixpyrrole derivatives as described herein.

Calix[4]pyrrole β-acid 12. Compound 10 was de-esterified to produce calix[4]pyrrole β-acid 12 by refluxing in a solution of NaOH in EtOH/H$_2$O. The acid was clarified by adding perchloric acid to the cooled reaction solution and then collected by filtration. This yielded a white powder.

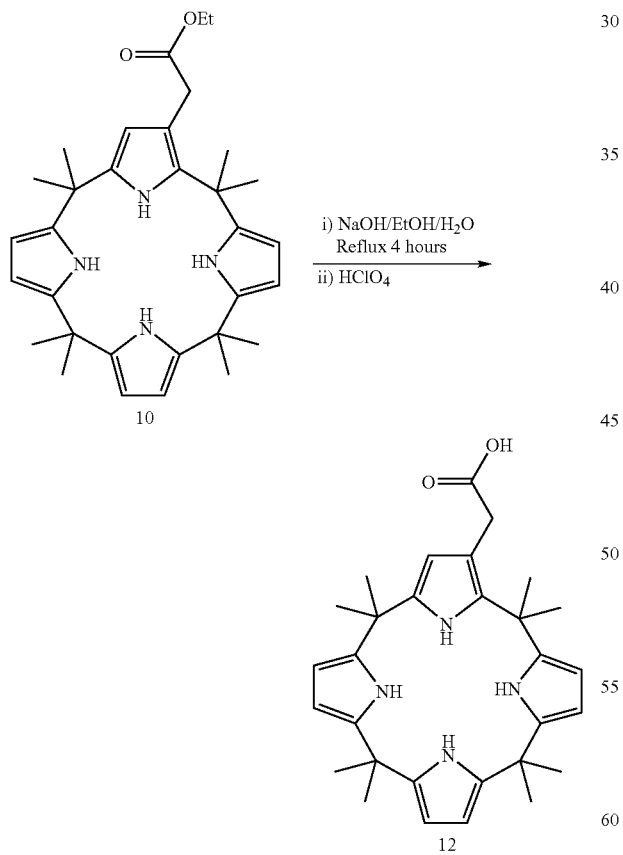

10 i) NaOH/EtOH/H$_2$O Reflux 4 hours
ii) HClO$_4$

12

Compound 10 (200 mg, 0.38 mmol) was stirred in 20 mL ethanol. The slurry was heated to reflux and NaOH$_{aq}$ (20 mL, 2.0 M) was added. The reaction was heated at reflux until all the ester had been consumed (approximately 4 hours). The ethanol was then removed in vacuo and a further 50 mL of cold water was added to the solution. The solution was then acidified with concentrated perchloric acid to pH 1. The monoacid 12 then precipitated out as a white powder was collected by filtration and dried under high vacuum to yield 146 mg (79%). $^1$H NMR (500 MHz, CD$_2$Cl$_2$) δ: 7.84 (s, 1H, NH), 7.24 (s, 1H, NH), 7.01 (coincident singlets, 2H, NH), 5.90–5.76 (overlapping multiplets, 5H, CH$_{py}$), 3.71 (s, 2H, OCH$_2$), 1.51 (s, 6H, CCH$_3$), 1.50 (s, 6H, CCH$_3$), 1.48 (s, 6H, CCH$_3$), 1.47 (s, 6H, CCH$_3$), $^{13}$C NMR (500 MHz, CD$_2$Cl$_2$) δ: 179.13 (C=O), 139.96 (C$_{py}$), 139.20 (C$_{py}$), 139.09 (C$_{py}$), 138.60 (C$_{py}$), 138.52 (C$_{py}$), 137.45 (C$_{py}$), 133.96 (C$_{py}$), 109.27 (C$_{py}$) 107.11 (CH), 103.21 (CH), 103.14 (CH), 103.05 (CH), 102.91 (CH), 102.75 (CH), 102.14 (CH), 37.20 (CCH$_3$), 35.49 (CCH$_3$), 35.40 (OCH$_2$), 35.23 (CCH$_3$), 33.68 (CCH$_3$), 30.38 (CCH3), 29.16 (CCH$_3$), 29.09 (CCH$_3$), 29.00 (CCH$_3$), 28.85 (CCH$_3$). High resolution FABMS calc for C$_{30}$H$_{38}$N$_4$O$_2$486.2989; found 486.2995 (Δ1.1 ppm).

β-substituted "monohook" calix[4]pyrrole 12 is particularly useful for further substitution as described in Examples 8, 9, 10, and 11.

β-Octamethoxy-meso-tetraspirocyclohexylcalix[4]pyrrole 13. 3,4-Dimethoxypyrrole (0.568 g, 4.5 mmol) and cyclohexanone (437 mg, 4.5 mmol) were dissolved in glacial acetic acid (10 mL), and the solution was stirred for 3 hours in the dark under argon, forming a black solution. The acid was then removed in vacuo and the residue purified by column chromatography (SiO$_2$, CH$_2$Cl$_2$ eluant). The product was collected as the second fraction from the column having an R$_f$=0.33 (81 mg, 0.097 mmol) in a yield of 8.6%. Following chromatographic purification, the solvent was immediately reduced in vacuo and the product 13 stored under argon in the freezer. $^1$H NMR (300 MHz, CD$_2$Cl$_2$) δ: 6.11 (s, 4H, NH), 3.77 (s, 24H, OCH$_3$), 2.08 (s, br., 16H, CH2), 1.45 (s, br., 24H). $^{13}$C NMR (75.42 MHz, CD$_2$Cl$_2$) δ: 136.3, 75.73, 61.1, 42.5, 35.1, 26.3, 23.9. High resolution FABMS calc for C$_{48}$H$_{68}$N$_4$O$_8$ 828.5037 found 828.5025 (Δ1.5 ppm).

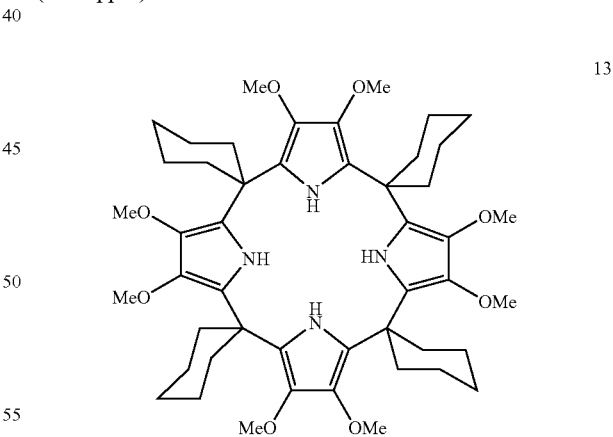

13

β-Substituted calix[4]pyrrole 13 shows decreased anion binding affinity relative to compound 2 due to electron donating properties of the methoxy substituents. These types of compounds are useful as HPLC column media since low affinity constants and fast complexation-decomplexation rates generally lead to efficient separation of substrates (see Example 10).

β-Octabromo-meso-octamethylcalix[4]pyrrole 14. An oven-dried 100 mL round-bottomed flask containing a stir bar was charged with meso-octamethylcalix[4]pyrrole (0.69 g, 1.6 mmol) and 50 mL of dry tetrahydrofuran. With stirring, N-bromosuccinimide (2.34 g, 13.1 mmol) was added all at once, causing the reaction mixture to turn yellow. A reflux condenser and argon balloon were affixed to the flask, which was heated to gentle reflux in the dark. After 48 h, the clear red-brown solution was allowed to cool to room temperature, and the THF was removed in vacuo. The tan solid which remained was triturated with 20 mL of dichloromethane, and the $CH_2Cl_2$ solution was flash chromatographed on silica gel (1:1 $CH_2Cl_2$-hexanes as eluent). Colorless-to-light-yellow fractions with $R_f$=0.73 were combined and evaporated to afford a white solid. Drying under high vacuum gave 1.53 g (90%) of the desired product 14. $^1$H NMR (CDCl$_3$): δ1.56 (s, 24H), 7.34 (br s, 4H). $^{13}$C NMR (CDCl$_3$): δ25.9, 38.2, 98.6, 130.4. LRMS (FAB$^+$): m/z 1059, 979, 901, 821, 741. Elemental analysis calc. for 14.2(DMSO) C, 31.61; H, 3.32; N, 4.61. Found C, 32.18; H, 3.31; N, 4.59.

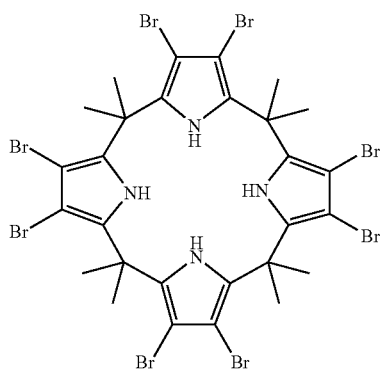

14

Figure 7:
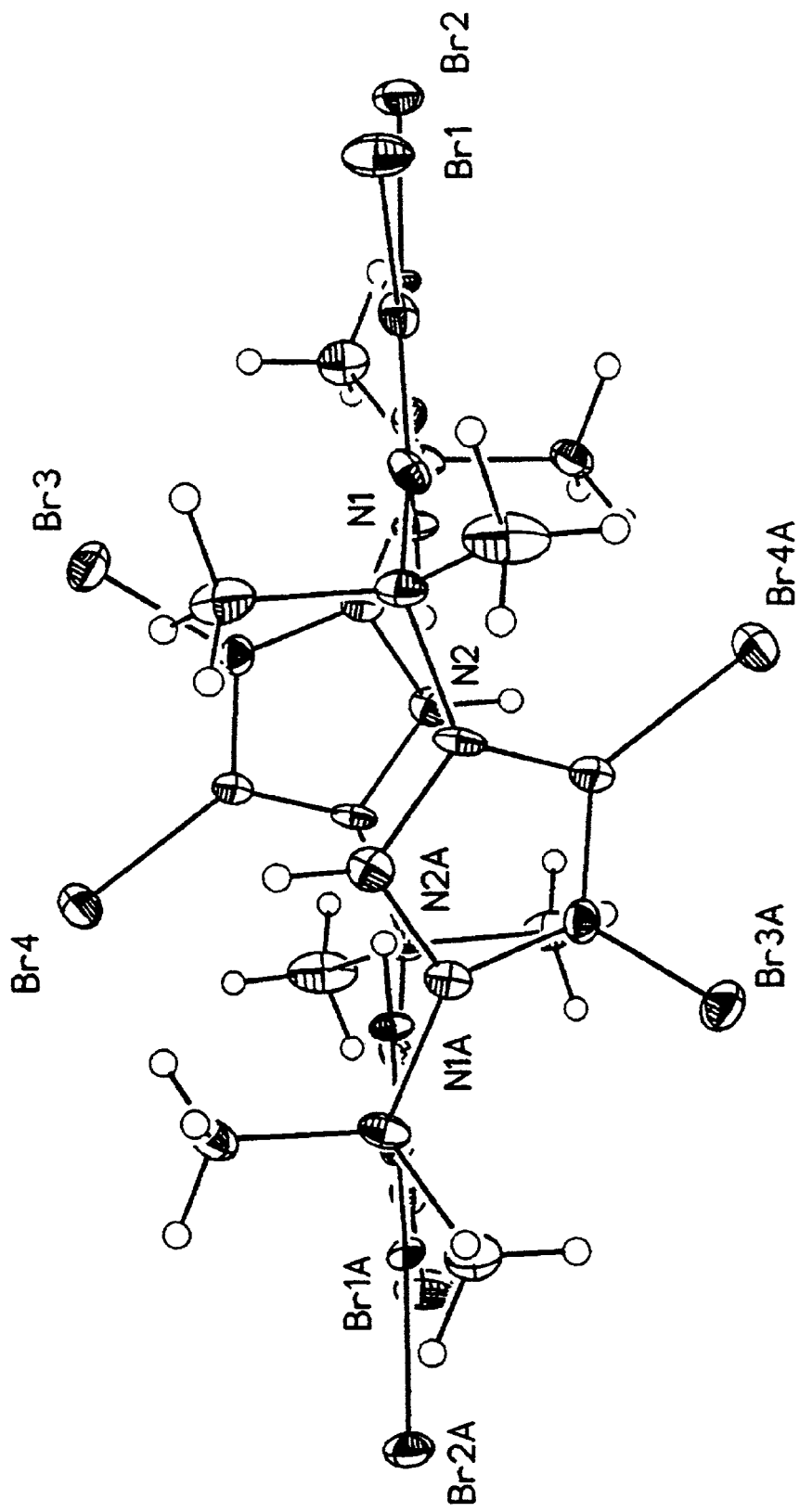
FIG. 7 illustrates an X-ray crystal structure of β-octabromo-meso-octamethylcalix[4]pyrrole. 14, adopting a 1,3-alternate conformation. Thermal ellipsoids are at the 30% probability level.

Single crystals of compound 14 were grown by slow evaporation of a dilute dichloromethane solution of the macrocycle (FIG. 7). The structure reveals that compound 14 exists in a chair-like flattened 1,2-alternate conformation in the solid state (i.e., the dihedral angles between pyrrole rings and plane through the calixpyrrole meso-carbon atoms are 66.8°, 5.8°, −66.8° and −5.8°). Crystallographic summary for $C_{28}H_{28}N_4Br_8$: Large, colourless prisms were grown by slow evaporation from $CH_2Cl_2$. Crystals were monoclinic, P2$_1$/n Z=2, in a cell of dimensions: a=10.819(4), b=12.042(4), c=12.746(4) Å, β=99.01(2)°, V=1640.1(10) Å$^3$, $\rho_{calc}$=2.15 gcm$^{-3}$, μ=98.07 cm$^{-1}$, F(000)=1008. A total of 7416 reflections were measured, 3763 unique ($R_{int}(F^2)$=0.091) on a Siemens P3 diffractometer using graphite monochromatised Mo Kα radiation (λ=0.71073 Å) at −75° C. The structure was refined on $F^2$ using SHELXTL/PC (ver 5.03, Siemens Analytical X-ray Instruments, Madison, Wis., USA) to an $R_w$=0.131, with a conventional R=0.0575 (2231 reflections with $F_0$>4[σ($F_0$)]), and a goodness of fit=1.105 for 182 refined parameters. The molecule lies on a crystallographic inversion centre at 0,0,0.

β-Substituted calix[4]pyrrole 14 shows increased anion binding affinity relative to the parent calix[4]pyrrole 1 due to the electron withdrawing properties of the bromine substituents (see Example 10). Receptors with an increased anion binding ability such as 14 are useful as anion sequestering agents (e.g., in removal of phosphate and nitrate pollutants from aqueous environments) (see Example 12) or as synthons in reactions to produce further modified calix[4] pyrroles. The present inventors envision this system will be useful as a precursor to a calix[m]pyridino[n]pyrrole or a calix[m]pyridine.

While the present example describes ester (10, 11), acid (12), alkoxy (13) and halo (14) β-substituents, one of skill in the art would be able to synthesize further modified β-substituted molecules in the light of the present disclosure and using standard organic chemical synthesis reactions as described herein.

β-Substituted calix[4]pyrrole macrocycles have similar utility to that of the meso-substituted molecules described herein.

EXAMPLE 4

Use of Calix[n]arene in the Synthesis of Calix[n]pyrrole, and Pseudo Dimers Thereof The present example provides the synthesis of a calix[n]arene-calix[n]pyrrole pseudo dimer. Reaction of p-tert-butylcalix[4]arene tetramethyl ketone (0.5 g, 0.57 mmol) with pyrrole (0.153 g, 2.29 mmol) in a dichloromethane/ethanol mixture, in the presence of methanesulfonic acid, followed by column chromatography on silica gel ($CH_2Cl_2$, eluant) afforded the calixpyrrole-calixarene pseudo dimer 15 in 32% yield. Compound 15 gave spectroscopic and analytical data in accord with the assigned structure. As a consequence of this template synthesis, the stereochemistry at the calixpyrrole meso-carbons is automatically defined. Thus this method of synthesis produces only one configurational isomer even though all four ketone groups involved in the synthesis of an individual calixpyrrole are asymmetrical (see Example 7).

Analytical and spectroscopic data for compound 15: Analysis for $C_{72}H_{84}N_4O_4$: Calculated C, 80.86%; H, 7.92%; N, 5.24%. Found C, 80.57%; H, 7.95%; N, 5.11%. High resolution positive ion FABMS: Calculated ($C_{72}H_{84}N_4O_4$) 1068.649; Found 1068.648 (Δ1.4 ppm). $^1$H NMR (CD$_2$Cl$_2$) δ: 11.22 (s, 4H, NH), 7.22 (s, 8H, ArH), 5.83 (d, J=2.5 Hz, 8H, CH), 4.35 (d, J=12.5 Hz, 4H, ArCH$_2$Ar), 3.80 (s, 8H, OCH$_2$), 3.37 (d, J=12.5 Hz, ArCH$_2$Ar), 1.58 (PyCCH$_3$), 1.18.(s, 36H, tert-Bu). $^{13}$C NMR (CDCl$_3$) δ: 151.3, 146.8, 137.2, 134.4, 126.1, 101.7, 90.2, 37.9, 34.1, 31.4, 29.6, 21.1.

Figure 8:
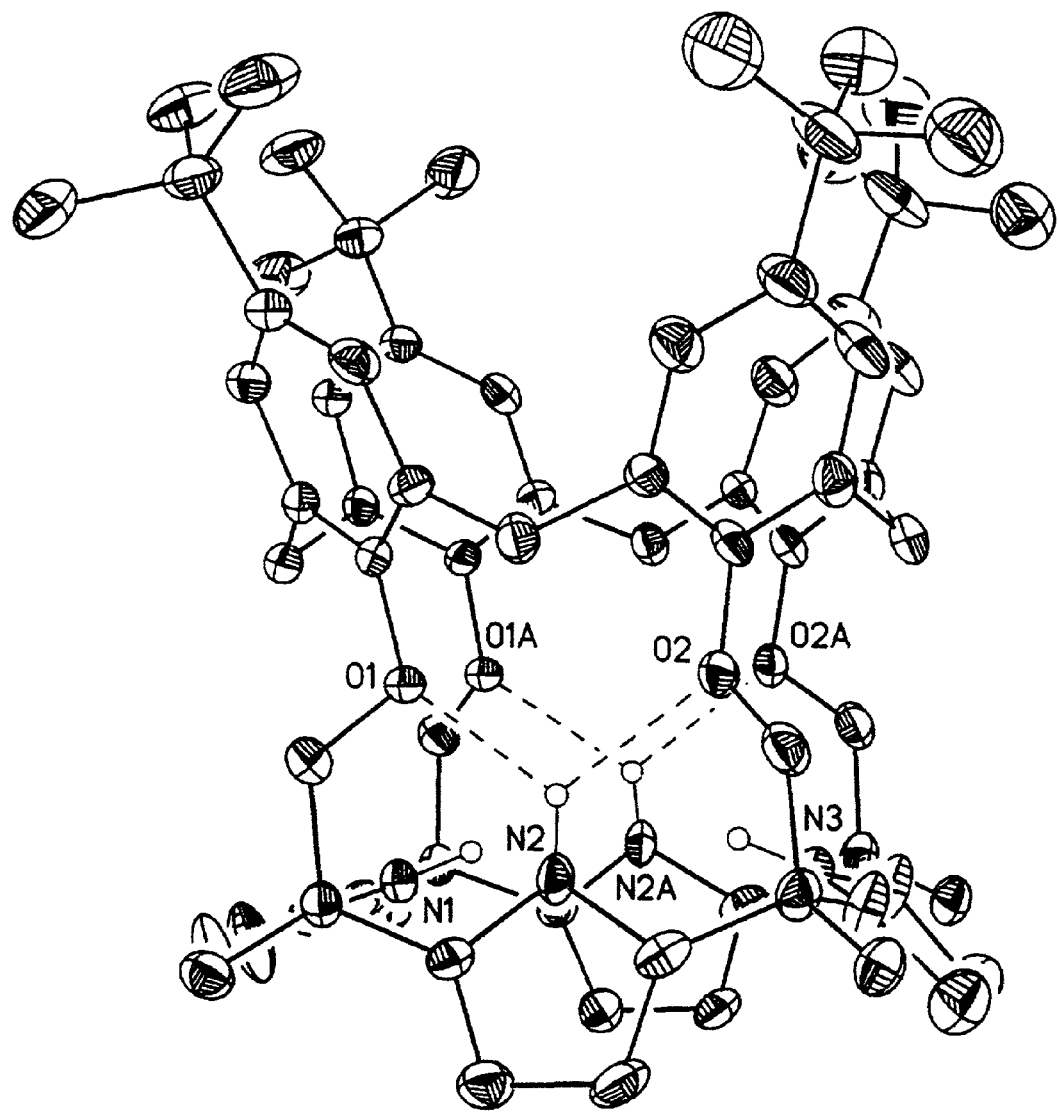
FIG. 8 illustrates an X-ray crystal structure of a meso-tetramethylcalix[4]pyrrole-p-tert-butylcalix[4]arene pseudo dimer, 15. Thermal ellipsoids are at the 30% probability level.

Crystals were obtained by slow evaporation of a dichloromethane solution of compound 15. The crystals were then subject to X-ray diffraction structural analysis. The resulting structure shows the calixarene in a cone conformation. The pyrrole NH groups are within hydrogen bonding distance of the lower rim calixarene oxygen atoms (FIG. 8).

Crystallographic summary for 15.xCH$_2$Cl$_2$. Large regions of disordered solvent of unknown stoichiometry in this structure presented difficulties with this analysis, however the structure of the calixarene-calixpyrrole pseudo dimer is a reliable description of this unique and interesting molecule. Faintly yellow crystals, monoclinic, C$_2$/m, Z=4 in a cell of dimensions a=25.836(5) Å, b=20.139(3) Å, c=15.46 (2) Å, β=106.0(1)°, V=7719(2) Å$^3$. $\rho_{calc}$: x=4; 1.21 gcm$^{-3}$; x=6, 1.36 gcm$^{-3}$. 9112 unique reflections of which 4121 were observed (I>2σ(I)). Data collected at −90° C. on a Siemens P3 diffractometer. The final R=0.148.

Figure 9:
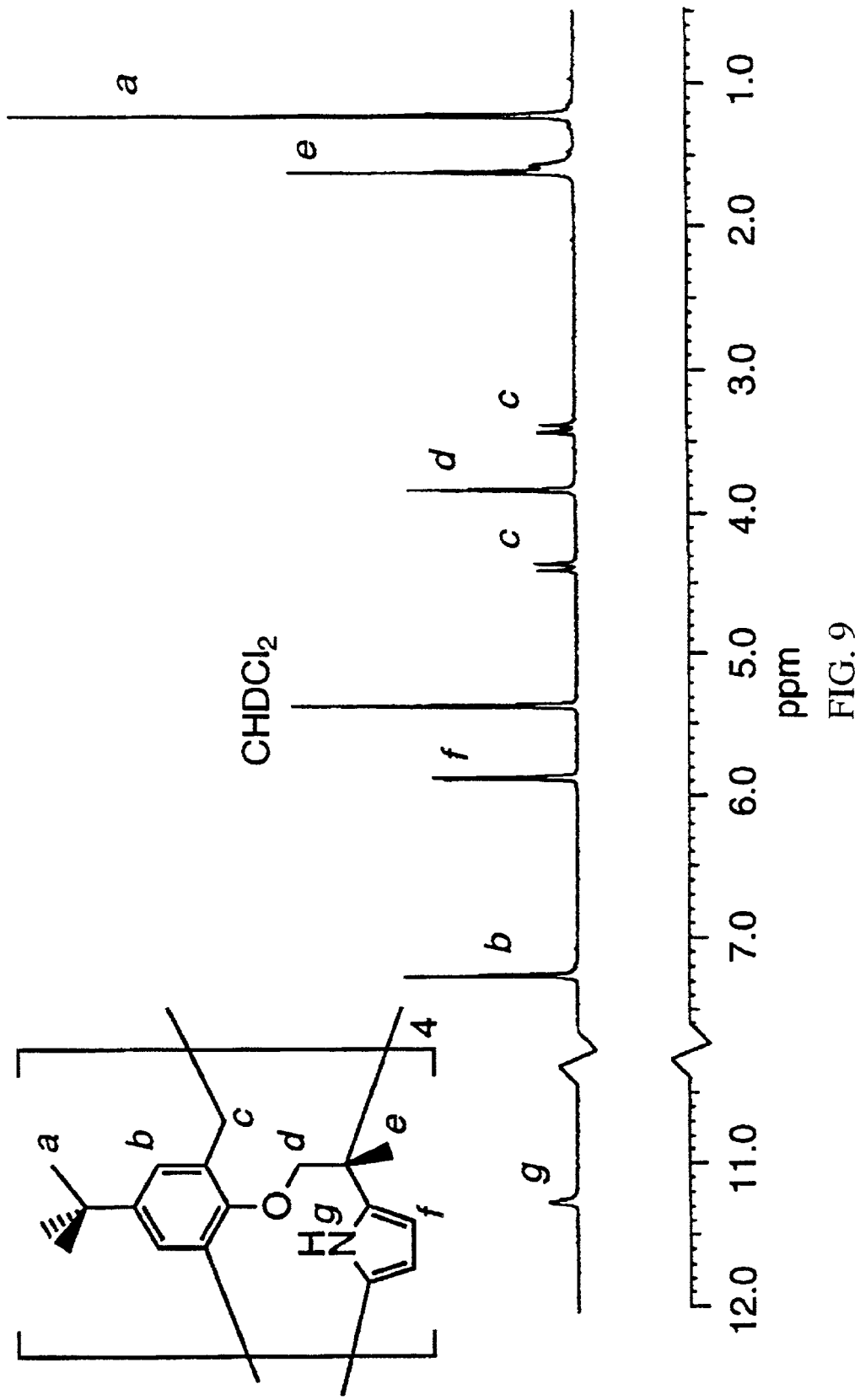
FIG. 9 illustrates a ¹H NMR of a meso-tetramethylcalix[4]pyrrole-p-tert-butylcalix[4]arene pseudo dimer in $CD_2Cl_2$.

The $^1$H NMR spectrum of 15 in dichloromethane-d$_2$ shows that the pyrrole NH protons, which are normally observed at around 7 ppm in other calix[4]pyrroles, resonate at 11.22 ppm (FIG. 9). This can be attributed to hydrogen bonding between the pyrrole NH groups and the calixarene oxygen atoms. CD$_3$OD was added to the NMR solution in an attempt to disrupt this hydrogen bonding interaction, however this had a negligible effect on the $^1$H NMR spectrum. Similarly, addition of 10.0 equiv. tetrabutylammonium fluoride (which has been shown to bind strongly to other calix[4]pyrroles) caused no changes in the NMR spectrum. Based on these findings, the present inventors conclude that the dimer is adopting a cylindrical conformation in solution due to these clearly favorable NH—O hydrogen bonds.

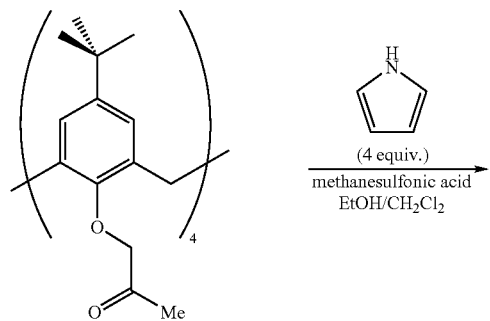

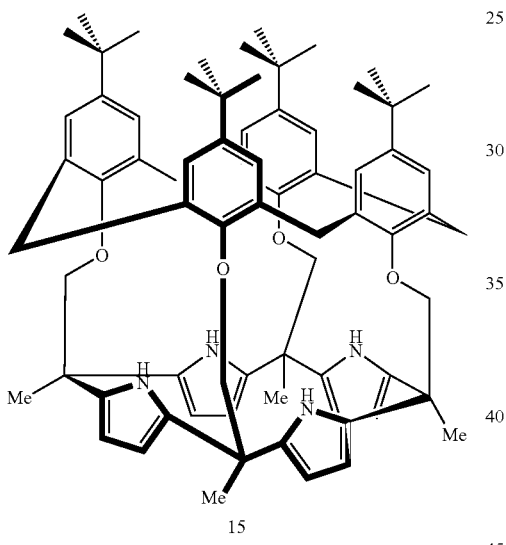

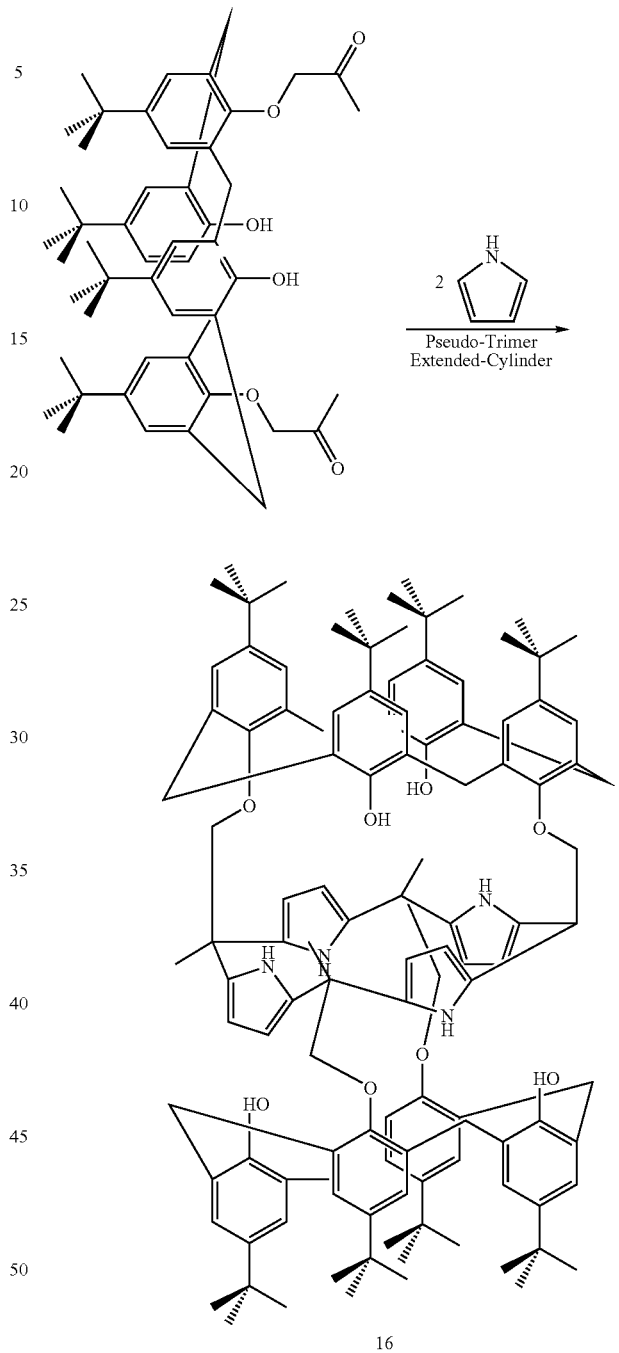

These types of calixarene-calixpyrrole molecular cylinders may be useful as receptors of neutral guests, as they possess a hydrophobic cavity. Additional functional groups could be appended to the free phenolic OH groups on the calixarene. These may be used to attach the molecule to a polymer or other solid support. Such solid supported compounds may be used in column chromatography, for example. Alternatively, an optical or electrochemical sensing group such as anthracene or ferrocene could be attached and may be able to sense the inclusion of neutral species in the cylinder and therefore act as a sensor. These materials may also be able to extract toxic organic substances (such as insecticides and PCBs) from aqueous solutions and, being potential receptors for zwitterions, aid in the purification of amino acids, peptides, proteins, and the like.

In addition to a dimer cylinder, trimers and larger tubular polymers may be prepared. The synthesis of a calixarene/calixpyrrole/calixarene pseudo trimer 16 is illustrated below:

Calix[4]arene tetra ketones in the 1,3-alternate conformation may be used to make calixarene-calixpyrrole tubular polymers which may have interesting properties, either alone or with a guest species bound within the polymer tube.

Other n-fold templates may be used around which a calix[n]pyrrole may be constructed. Examples of such molecules include, but are not limited to, calix[n]arenes, resorcinarenes, CTV, and cyclic sugars such as the α-, β- or γ-cyclodextrins. Alternatively, benzene rings substituted with ketone groups, or azacrown ethers with N-pendant ketone moieties may serve as templates in the synthesis of the present invention. In one aspect of the invention, it is preferred that the ketone groups of the template all be pointing in the same direction. For example, in the case of calixarenes, the calixarene is in a cone conformation.

EXAMPLE 5

Synthesis of Calix[n]pyrroles

Calix[n]pyrroles where n is greater than 4 have not previously been described. The present example provides methods for synthesis of higher order cyclic oligomers where n is 5–8. Prior art methodology for preparing calix[4]pyrroles involved the condensation of a ketone with a pyrrole using a Brønsted acid such as methanesulfonic acid or hydrochloric acid. This method produces exclusively calix[4]pyrrole. The present inventors have developed a methodology that employs Lewis acid catalysis of the condensation of pyrroles and ketones to yield novel calix[5, 6, 7, or 8]pyrroles having high yield and purity.

Synthesis of Calix[n]pyrroles where n=5, 6, 7, or 8. A pyrrole and a ketone may undergo Lewis acid-catalyzed condensation to form a generalized calix[n]pyrrole having structure I. The reaction conditions have been optimized for the preparation of higher calix[n]pyrroles (n>4) by varying pyrrole and the ketone ratios and employing $BF_3.Et_2O$ as a catalyst. Optimal conditions for the formation of higher order calix[n]pyrroles (n>4) are a 1:1 to a 1.25:1 molar ratio (ketone:pyrrole) with a 10% Lewis acid catalyst. The concentration of starting compounds ranged from 50 mM to 1 mM depending on the solvent used e.g. dichloromethane (dry), chloroform and acetonitrile, although it may be possible to use other solvents or solvent mixtures to obtain optimum yields of a given calix[n]pyrrole.

Lewis acids such as $BF_3.OEt_2$, $BF_3$methanol, $VOCl_3$, $TiCl_4$, and $Mn(OAc)_3$ have been used as catalysts and it has been found that $TiCl_4$ in dry dichloromethane produces higher yields of calix[n]pyrroles than the other catalysts. Lewis acids may also be used in doped zeolites, monymorillonites, clays, silica and alumina which can provide a convenient site for calix[n]pyrrole formation.

The conditions for the preparation of calix[n]pyrroles ranging from n=4 to 10 are: acetone (0.5808 g, 10 mmol) and pyrrole (0.67 g, 10 mmol) were dissolved in dry dichloromethane (150 mL) under an argon atmosphere with stirring under argon for 15 minutes. The catalyst, $BF_3.Et_2O$ (0.5 mL of 1M solution in dichloromethane, 0.5 mmol), was slowly added via syringe. The reaction mixture was stirred under argon for between 24 to 48 hours. HCl (3 mL of 3%) was then added and the mixture stirred for 10 minutes. The reaction mixture was transferred to a separators funnel and the organic phase was washed with water and dried over sodium sulfate. The solvent was evaporated and the crude reaction mixture was filtered over a short neutral alumina column using dichloromethane as the mobile phase. The calix[n]pyrrole products were purified by flash chromatography or by preparative HPLC using dichloromethane-hexane (3:1) a mobile phase. Yield 78% The ratio for n is as follows: 1, n=4, 60%; 17, n=5, 12%; 18, n=6, 9%; 19, n=7, 5%; 20, n=8, 3%. Separated calix[n]pyrroles were characterized by HRMS: Cyclic pentamer: 17, n=5, For $C_{35}H_{45}N_5$ calc. 535.367497, found. 535.367194. For [MH$^+$] $C_{35}H_{46}N_5$ calc. 536.375322, found 536.374278. Cyclic hexamer: 18 n=6 For $C_{42}H_{54}N_6$ calc. 642.440996, found 642.440390. Cyclic heptamer: 19 n=7 For $C_{49}H_{63}N_7$ calc 749.514496, found 749.514133. Cyclic octamer: 20 n=8 For $C_{56}H_{73}N_8$ calc. 857,5958, found 857.5923.

Chloroform and acetonitrile may also be used as solvents. $BF_3.MeOH$ was used as a catalyst with 73% overall yield. When 1-alkyl-, or 1-arylpyrrole were used, the reaction again produced cyclic systems; N-substituted calix[n]pyrroles where n is from 4 to 8, with the main product n=4, but with higher ratio for n>4 than in case of pyrrole (the ratio estimate is 35:12:9:7:5) for n=4–8, for 1-methylpyrrole and ratio 29:12:9:8:6 for 1-phenylpyrrole.

The procedure for the use of high valent Lewis acid catalysts (e.g. $TiCl_4$) in calix[n]pyrrole synthesis is as follows: acetone (0.581 g, 10 mmol) and pyrrole (0.67 g, 10 mmol) were dissolved in 100 mL of dry dichloromethane under argon. Titanium tetrachloride (1 mL of 1M solution in dichloromethane, 1 mmol) was then added to the solution under argon while stirring at room temperature. Immediately after addition, a precipitate was formed, which redissolved after 5 minutes stirring. The reaction mixture was stirred at room temperature for 20 hours, then washed with 3% HCl, water and dried over sodium sulfate. The product was purified by column chromatography on neutral alumina. Final separation was performed by flash chromatography on silica gel using dichloromethane-hexane 4:1. The overall yield was 67% with a calix[n]pyrrole distribution as follows: 88 (1, n=4), 8 (17, n=5), 6 (18, n=6), 3 (19, n=7), 2 (20, n=8).

The procedure has been repeated using analogous conditions to those used with titanium tetrachloride but using other Lewis acids such as $VOCl_3$, $Mn(OAc)_3$, $SnCl_4$, $AlCl_3$, or $UO_2(OAc)_2$ and also using a number of different solvents.

A variety of cation exchange resins (Dowex) were employed in their H$^+$ rich forms, however, the product was exclusively the cyclic tetramer.

Synthesis of Calix[n]pyrroles using clays. Montmorrilonite K10 (Aldrich) was added to a 250 mL flask and dried at 120° C./0.2 Torr for 2 hours. After cooling to room temperature under argon, dry dichloromethane (100 mL) was added, followed by acetone (0.0581 g. 1 mmol) and pyrrole (0.067 g, 1 mmol) successively. The reaction mixture (suspension) was vigorously stirred under argon for 8 hours. The solid material was filtered through Celite and washed with dichloromethane (25 mL). The combined dichloromethane filtrates were evaporated and the product was purified on a short neutral alumina column (dichloromethane eluant). The products separated by preparative HPLC on a silica gel column using dichloromethane-hexane as the mobile phase. Overall yield was 68% with the main product being calix[4]pyrrole 1 (59%). Additionally, calix[5]pyrrole 17 (6% yield and 3% of higher oligomers (n>6)) were isolated.

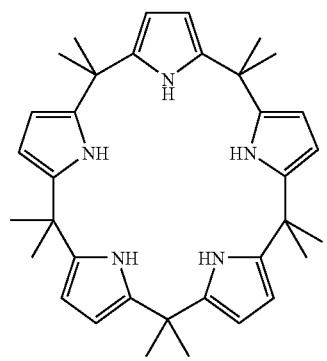

17

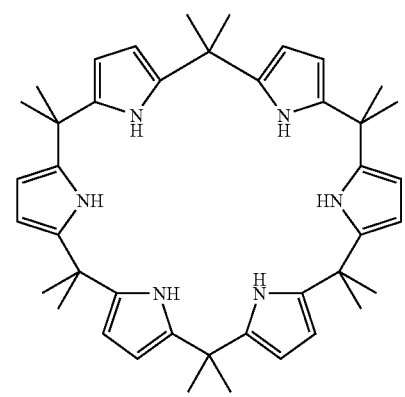

18

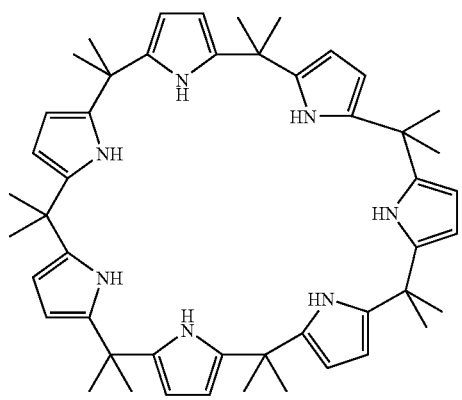

19

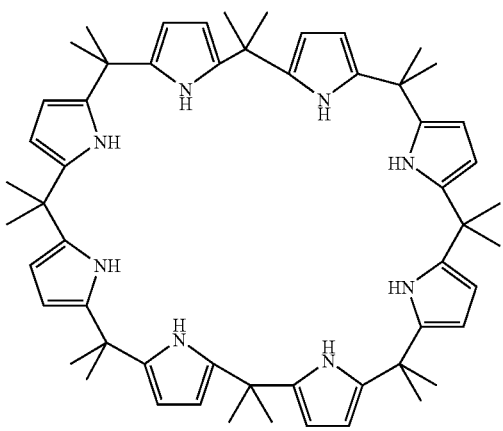

20

Synthesis of calix[n]pyrroles via cyclization of 2-[(dialkylhydroxy)methyl]pyrrole Calix[n]pyrroles may also be synthesized from 2-[(dialkylhydroxy)methyl]pyrroles. These molecules are cyclized using either a Brønsted acid or a Lewis acid. One approach for the preparation of 2-[(methylalkyl)hydroxymethyl]pyrrole derivative is based on the reaction of commercially available 2-acetylpyrrole with alkylmagnesiumbromides (Grignard reagents) affording the desired product 21 (R=alkyl) as a starting building block for Brønsted acid, or Lewis acid catalyzed cyclization.

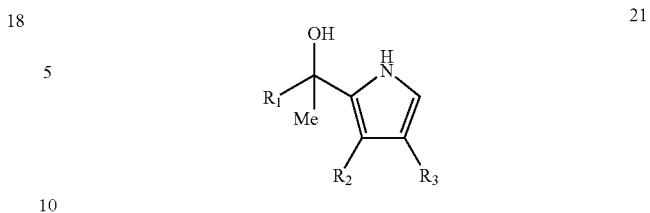

21

2-Acetylpyrrole (0.109 g, 1 mmol) was dissolved in 50 mL of dry THF under argon. The solution was then cooled to −78° C. A solution of MeMgBr (1 mL of a 1 M solution in diethylether) was added via syringe while stirring. The reaction mixture was allowed to warm up to −15° C. for 10 minutes. It was then cooled down and another 1.5 molar equivalents MeMgBr (1.5 mL of 1M solution; 1.5 mmol) was slowly added at −78° C. The reaction mixture was stirred at that temperature for 15 minutes and then slowly allowed to warm up to 0° C. After stirring for two hours at 0° C., the reaction was quenched with MeOH and evaporated to dryness. The residue was redissolved in dichloromethane (50 mL) and washed with a 5% solution of ammonium chloride and water. The 2-(dimethylhydroxymethyl)pyrrole was subjected to acid and Lewis acid catalytic macrocyclization giving mixture of calix[n]pyrroles at 65% yield with n =4–8 as the products with the main product being 1. The present inventors envision this synthesis could be extended to pyrroles with ketone groups in the α-position.

β-Octamethylcalix[4]pyrrole 22. 3,4-Diethylpyrrole (0.369 g, 3 mmol) was dissolved in dry THF (30 mL) under argon and the solution was cooled to −78° C. A MeMgBr solution (3 mL of 1 M solution in diethylether, 3 mmol) was slowly added and stirred at that temperature for 10 minutes. The solution was allowed to warm up to −10° C. for 10 minutes and was then cooled to −78° C. At this point, 1.2 molar equivalents of tert-BuLi was added (3.6 mL of a 1 M molar solution in hexane, 3.6 mmol) and the reaction mixture was kept at −78° C. for 30 minutes. The reaction mixture was allowed to warm up to −10° C. for 10 minutes and then cooled to −78° C. Acetone (0.29 g, 5 mmol) was added to the solution at that temperature and stirred for 30 min. at −78° C., then allowed slowly warm up to −10° C. and kept at that temperature for 1 hour. The reaction was quenched by addition of 1 mL of saturated water solution of ammonium chloride. After evaporation of the organic solvent, the product 21 ($R_1$=Me, $R_2$=$R_3$=Et) was extracted into dichloromethane and isolated by flash chromatography on silica gel with dichloromethane as the mobile phase. Yield 78%. HR MS for $C_{11}H_{19}NO$ calc. 181.146664, found 181.14781. 2-[(Dimethyl)hydroxymethyl]-3,4-diethylpyrrole 21 was subjected to acid and Lewis acid catalysed cyclization. The mixture of calix[n]pyrroles was isolated in 45% net yield. The main product has n=422: $(C_{11}H_{19}N)_4$ found 652; but a 5% total yield of higher analogues was also obtained.

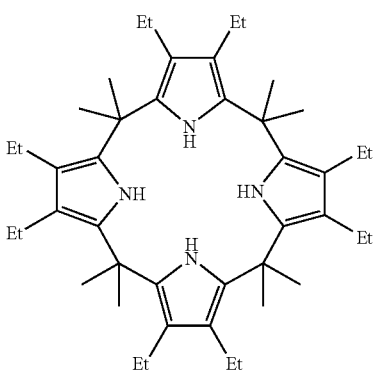

22

Pyrrole can be substituted for 3,4-diethylpyrrole in this procedure.

The present inventors envision that 1-alkyl pyrrole and 1-alkyl-3,4-diethylpyrrole and ketones could be used in a modification of the above procedure: 1-methylpyrrole or 1-methyl-3,4-diethylpyrrole (3 mmol) are dissolved in dry THF (30 mL) under argon and cooled to −78° C. 1.2 molar equivalents of tert-BuLi are added (3.6 mL of a 1 M molar solution in hexane, 3.6 mmol) and the reaction mixture kept at −78° C. for 30 minutes. The reaction is warmed to −10° C. for 10 min. and then cooled to −78° C. A general ketone (5 mmol) added and the reaction mixture was stirred for 30 min. at −78° C. The solution is allowed to slowly warm up to −10° C. and stirred at that temperature for 1 hour. The reaction is quenched with 1 mL of a saturated water solution of ammonium chloride. After evaporative removal of the organic solvent, the product is extracted to dichloromethane and isolated by flash chromatography on silica gel using dichloromethane as a eluent. The products: 2-[(dialkylhydroxy)methyl]pyrrole derivates were used for the preparation of calix[n]pyrroles using the methodology described above.

EXAMPLE 6

Conversion of Calix[m+n]pyrroles to Calix[m]pyridino[n]pyrrole

A general synthetic method for the preparation of calix[m]pyridino[n]pyrroles where m and n designate a number of pyridines and pyrroles in the macrocycle, respectively, is unknown to date. Calix[2]pyridino[2]pyrroles and calix[1]pyridino[3]pyrroles have been previously synthesized via an organometallic-mediated transformation using zirconium and other metals. However, calix[m]pyridino[n]pyrroles where m>2 have not been reported.

The synthetic approach provided by the present inventors differs from the prior art methods and provides access to a broad variety of calix[m]pyridino[n]pyrroles and calix[m]pyridines. The approach of the present synthetic protocol is based on a non organometallic-mediated pyrrole ring expansion involving one or more of the pyrrole rings contained in a calix[m+n]pyrrole macrocycle.

Expansion of pyrrole within an existing calix[m+n]pyrrole involves the cycloaddition of dichlorocarbene to a particular pyrrolic subunit followed by rearrangement to yield a corresponding pyridine. Dichlorocarbene may be generated under basic or neutral conditions. One or more pyrrolic subunits may react in this procedure specifically, varying the ratio of dichlorocarbene to calix[m+n]pyrrole allows control of the extent of conversion of pyrrole to pyridine which, in turn, determines the ratio of pyridine subunits to pyrrole subunits in the calix[m]pyridino[n]pyrroles.

The present inventors have also discovered a solvent dependence for the conversion of calix[m+n]pyrroles to calix[m]pyridino[n]pyrroles. The use of dioxane leads mainly to one and two converted units, while the use of 1,2-dimethoxyethane and prolonged reaction time provides for the full conversion of calix[m+n]pyrroles to calix[m]pyridines. Partial conversion of calix[m+n]pyrroles to calix[m]pyridino[n]pyrroles is also accomplished by the present methods.

Additionally, the present inventors have found that dichlorocarbene generated under neutral conditions (from sodium salts of trichloroacetic acid, for example) gives better yields than generating the dichlorocarbene under basic conditions (i.e. from the reaction of chloroform with sodium ethoxide).

A first method utilizes dichlorocarbene generated under neutral conditions and achieves fully converted calixpyridine product, meso-Octamethylcalix[4]pyrrole (10 mmol) was dissolved in dry 1,2-dimethoxyethane (75 mL). Four molar equivalents of dry sodium trichloroacetate were added per pyrrole ring. The reaction mixture was heated to reflux under an argon atmosphere for 20 hours. After cooling to room temperature, the solution was filtered and the organic solvent was evaporated in vacuo. The resulting residue was redissolved in dichloromethane, treated with charcoal, filtered over celite and evaporated to dryness. The crude product was purified over a short neutral alumina column (dichloromethane eluant). Final separation was achieved by flash chromatography on silica gel with dichloromethane and methanol (0–10%) as the mobile phase. Yield of fully converted product 27 is 35–50%. HRMS: For $C_{32}H_{33}N_4Cl_4$ [MH$^+$]: calc. 613. 145933, found 613.145490.

A second method employs a partial calix[4]pyrrole expansion process to form mixed calix[m]pyridino[n]pyrroles. Mixed systems were obtained using 1–3 molar equivalents of sodium trichloroacetate for each pyrrole ring in the macrocyclic system. The molar ratio of pyrrole/dichlorocarbene allows one to "tune" the number of pyrroles that are converted to pyridines. Using one molar equivalent of sodium trichloroacetate for each pyrrole unit, the main product was calix[1]pyridino[3]pyrrole 23 (76% yield). Using 2 equivalents, the main product was a mixture of the two calix[2]pyridino[2]pyrrole isomers 24 and 25 (83% yield). Using 3 molar equivalents, calix[3]pyridino[1]pyrrole 26 was obtained (56% yield). These compounds were isolated by flash chromatography and separation was obtained on semipreparative HPLC with dichloromethane-acetonitrile as a solvent and a gradient of acetonitrile from 0–5%. After column and HPLC separation, the following 3-chloropyridine macrocyclic products were characterized by HRMS: Monoconversion: HRMS For $C_{29}H_{35}N_4Cl$ calc. 474. 255025, found 474.254879. Bis conversion: HRMS For $C_{30}H_{34}N_4Cl_2$ calc. 520. 216053; found 520.215789 and 512. 215985. For tris conversion: HRMS For $C_{31}H_{33}N_4Cl_3$ calc. 566.177081, found 566.178902.

Mixed molecule systems were further obtained using a third procedure. Dioxane was used as a solvent under the conditions described which resulted in full conversion of the calix[4]pyrrole to calix[4]pyridine, the main products where calix[1]pyridino[3]pyrrole 23, calix[2]pyridino[2]pyrrole 24 and 25 and calix[3]pyridino[I]pyrrole 26. Conditions: reflux under argon for 15 hours, purification and separation of products as above.

Crystals of compound 24 were grown and the structure elucidated by X-ray diffraction. Crystallographic data for 24: Colorless crystals, triclinic, P$\bar{1}$, Z=4, in a cell of dimensions: a=12.544(1), b=15.406(2), c=16.770(3) Å, α=63.93 (1), β=82.957(9), γ=76.958(9)°, V=2835.0(9) Å$^3$, $\rho_{calc}$=1.23 g cm$^{-3}$, F(000)=1144. 4134 unique reflections, 2783 with $F_o$>4(σ($F_o$)). The final R(F)=0.113, Rw(F$^2$)=0.269, goodness of fit=4.30 for 668 parameters refined on F$^2$. Two crystallographically distinct molecules per unit cell. Dihedral angles of rings to root mean square plane through meso-carbons: pyrrole [1] 18.8°, pyridine [2] 113.2° (23.8°), pyrrole [3] 23.2°, pyridine [4] 67.2°(22.8'), and pyrrole [1] 21.7°, pyridine [2] 69.9°(20.1°), pyrrole [3] 161.7°(18.3°), pyridine [4] 67.0° (23.0°).

Sodium (1.15 g, 50 mmol) was dissolved in absolute ethanol (25 mL) in a flask fitted with a reflux condenser and a mechanical stirrer and the flask was flushed with argon. Calix[4]pyrrole (15 mmol) in chloroform (5 mL) was added and mixture was heated to 55° C. for 18 hours. The sodium chloride was filtered off, the residue was treated with charcoal and purified on a short neutral alumina column followed by flash chromatography on silica gel with dichloromethane-methanol (from 0–5%). The main product, was isolated as unreacted starting calix[4]pyrrole with only 3–9% conversion.

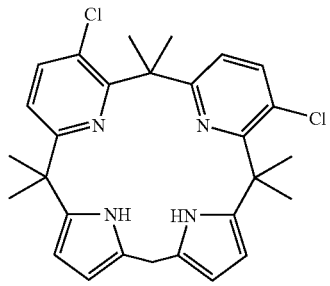

25

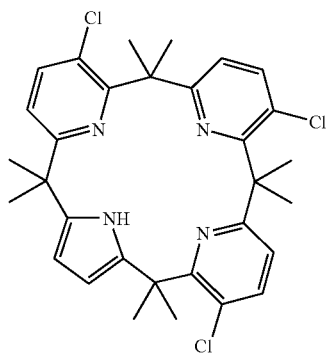

26

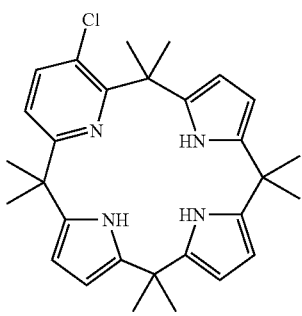

23

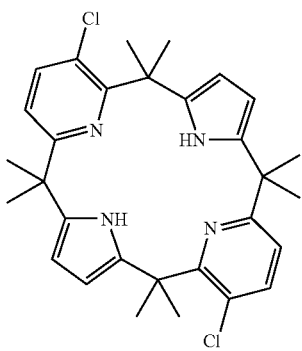

24

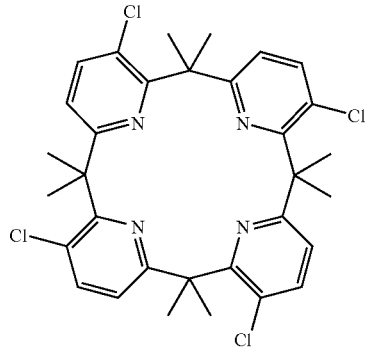

27

EXAMPLE 7

Configurational Isomers of Calixpyrrole

The structures of calix[4]pyrroles described herein are drawn two dimensionally. This representation obscures the fact that calixpyrroles containing more than one asymmetrically-substituted meso-position will be formed as a mixture of configurational isomers. For example, compound 5 (see Example 2), contains four asymmetrically substituted meso-positions and can exist as four different isomers which are chemically distinct from each other and may be separated via HPLC chromatographic techniques. A two dimensional representation is as follows.

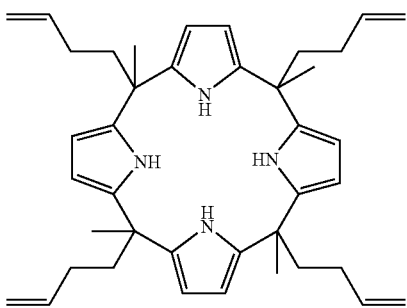

The four possible configurational isomers of compound 5 are as follows.

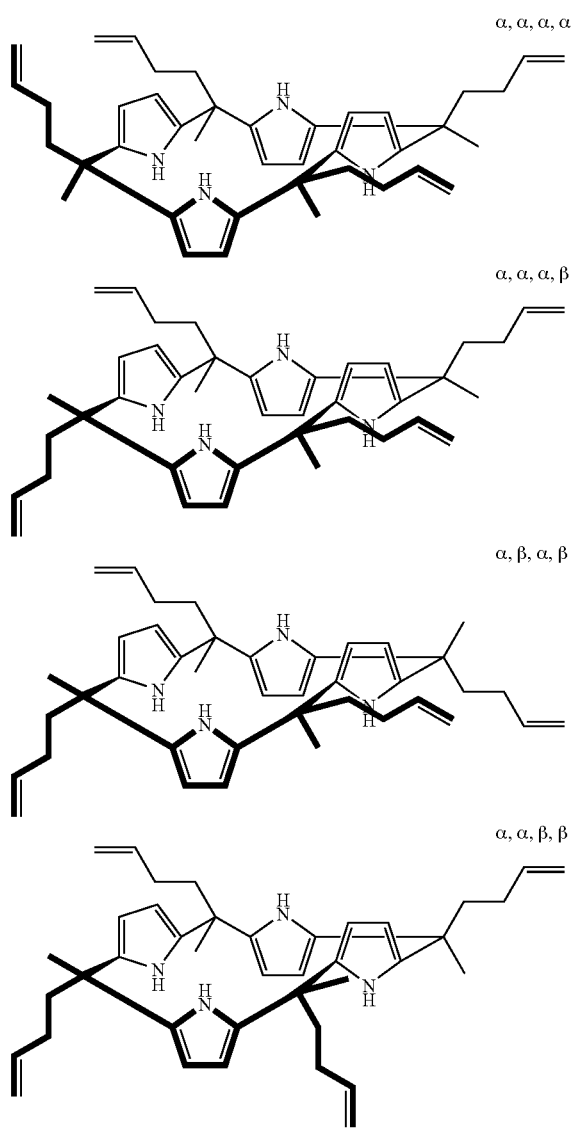

α, α, α, α

α, α, α, β

α, β, α, β

α, α, β, β

Therefore, as used herein, all two dimensional representations of calixpyrroles containing more than one asymmetrically substituted meso-position refer to all possible isomers (α,α,α,α), (α,α,α,β), (α,β,α,β) and (α,α,β,β) unless otherwise stated. For calix[5]pyrrole there will also be four possible configurational isomers (α,α,α,α,α), (α,α,α,α,β), (α,β,α,β, α) and (α,α,α,β,β), however for n>5 the number of possible configuarational isomers will increase above four.

EXAMPLE 8

Calix[n]pyrrole Derivatives, Multimers, Conjugates, and Synthesis Thereof

Calix[n]pyrrole derivatives, multimers and conjugates have been synthesized. Such molecules possess useful binding properties for ion, chiral substrate, or neutral molecule separation, for salt binding, for acting as sensors for ions or neutral guests and the like.

Amido-calixpyrroles 28 and 29 are particularly useful as anion binding agents. Additionally, they serve as model compounds for calixpyrrole modified silica gels wherein the calixpyrrole is linked to the modified silica gel via amide bonds.

Mono-β-butylamidocalix[4]pyrrole 28. Compound 12 ('β-hook' acid) (300 mg, 0.62 mmol) was dissolved in DMF (20 mL, dry) under and argon atmosphere, n-Butylamine (45 mg, 0.62 mmol) was added followed by BOP $PF_6$ (327 mg, 0.74 mmol) and triethylamine (125 mg, 1.2 mmol). The reaction mixture was stirred for 48 hours. The DMF was then removed in vacuo and the product purified by column chromatography ($SiO_2$, $CH_2Cl_2$: $CH_3OH$ 99:1 eluant) affording compound 28 as a white foam (331 mg, 99%). $^1H$ NMR (250 MHz, $CD_2Cl_2$) δ: 8.80 (s, 1H, NH), 7.24 (s, 1H, NH), 7.01 (coincident s, 2H, NH), 5.92–5.82 (m, 7H, $6CH_{py}$ and $NH_{amide}$), 5.70–5.69 (1H, d, $CH_{py}$), 3.51 (s, 2H, $OCH_2$), 3.29 (q, J=6.2 Hz, 2H, $CH_2$), 1.66–1.30 (coincident resonances, 28H, $8CH_{3\ meso}$, $2CH_{2\ hook}$), 0.96 (t, 3H, $CH_{3\ hook}$). $^{13}C$ NMR (62.9 MHz, $CD_2Cl_2$) δ: 173.0, 140.2, 139.7, 139.2, 138.9, 138.4, 138.1, 137.4, 134.2, 110.7, 106.9, 103.2, 103.2, 103.1, 102.7, 102.5, 101.6, 39.7, 37.1, 35.9, 35.5, 35.4, 35.2, 32.1, 29.2, 29.0, 28.7, 20.5, 14.0. High resolution FABMS calc for $C_{34}H_{47}N_5O$ 541.3781; found 541.3782 (Δ−0.2 ppm).

28

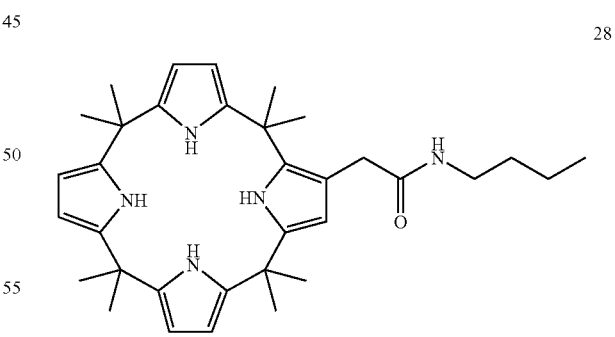

Mono-meso-butylamidocalix[4]pyrrole 29. Compound 4 ('meso-hook' acid) (268 mg, 0.43 mmol) was dissolved in DMF (20 mL, dry) under and argon atmosphere, n-Butylamine (31.6 mg, 0.43 mmol) was added followed by BOP $PF_6$ (230 mg, 0.52 mmol) and triethylamine (87 mg, 0.86 mmol). The reaction mixture was stirred for 48 hours. The DMF was then removed in vacuo and the product purified by column chromatography ($SiO_2$, $CH_2Cl_2$:$CH_3OH$ 99:1 eluant) affording compound 29 as a white foam (118 mg, 41%).

¹H NMR (250 MHz, CD₂Cl₂) δ: 7.26 (s, 2H, NH), 7.17 (s, 2H, NH), 5.93 (s, 2H, CH$_{py}$), 5.92 (s, 2H, CH$_{py}$), 5.90 (s, 2H, CH$_{py}$), 5.89 (s, 2H, CH$_{py}$), 5.46 (br.t, 1H, NH$_{amide}$), 3.17 (q, J=6.3 Hz, 2H, CH₂), 1.87 (br. coincident resoances, 18H, 9CH₂ $_{cyclohexyl}$), 1.45 (br. coincident resoances, 25H. 6CH$_{2cyclohexl}$–5CH$_{2\ hook}$+CH$_{3\ hook}$), 0.92 (t, J=7.2 Hz, 3H, CH₃). ¹³C NMR (62.90 MHz. CD₂Cl₂) δ: 172.6, 137.6, 137.2, 137.0, 136.9, 104.0, 103.9, 103.6, 40.0, 39.8, 39.5, 39.4, 38.8, 37.3, 37.0. 36.7, 32.2, 26.4, 25.6, 23.2, 20.9, 20.5, 14.0. High resolution FABMS calc for C₄₄H₆₁N₅O 675.4876; found 675.4879 (Δ1.2 ppm).

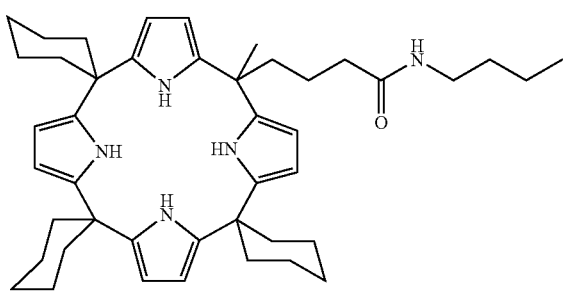

29

Mono-β-octadecylamidocalix[4]pyrrole 30. 'β-hook' acid 12 (250 mg, 0.51 mmol) was dissolved in DMF (20 mL, dry) under and argon atmosphere. Octadecylamine (139 mg, 0.51 mmol) was added followed by BOP PF₆ (273 mg, 0.61 mmol) and triethylamine (105 mg, 1.03 mmol). The reaction mixture was stirred for 72 hours. The DMF was then removed in vacuo and the product purified by column chromatography (SiO₂, CH₂Cl₂: CH₃OH 99:1 eluant) affording the product 30 as a yellow oil (330 mg, 87%). ¹H NMR (250 MHz, CD₂Cl₂) δ: 8.79 (s, 1H, NH$_{py}$), 7.50 (s, 1H, NH$_{py}$), 7.03 (s, 2H, NH$_{py}$), 5.89–5.80 (coincident multiplets, 7H, 6CH$_{py}$ and NH$_{amide}$), 5.67 (d, 1H, NH$_{py}$), 3.49 (s, 2H, CH₂CO), 3.26 (q, J=6.4 Hz, 2H, CH₂), 1.68 (m, 12H, 4CH₃), 1.49 (m, 12H, 4CH₃), 1.29 (m, 32H, CH₂), 0.90 (t, J=6.8 Hz, 3H, CH₃). ¹³C NMR (62.90 MHz, CD₂Cl₂) δ: 173.0, 140.2, 139.7, 139.2, 139.0, 138.4, 138.1, 137.4, 134.3, 110.8, 107.0, 103.3, 103.2, 102.7, 102.5, 101.7, 40.1, 37.2, 35.9, 35.50, 35.45, 35.2, 32.4, 30.2, 30.1, 29.8, 29.2, 29.0, 28.7, 27.4, 23.1, 14.3. High resolution FABMS calc for C₄₈H₇₅N₅O 737.5972; found 737.5957 (Δ2.0 ppm). The amide NH group of this receptor contributes to the calix[4] pyrrole anion binding process by providing a fifth hydrogen bond to the bound anion (see Example 10).

Molecules such as 30 are designed for insertion into lipid bilayers and are expected to be useful for transport.

Propyl bridged β-amidocalix[4]pyrrole dimer 31. A calix-pyrrole amide dimer compound 31 was formed by coupling 1,3-diaminopropane to the calixpyrrole acid 12. Again, this amide was formed as a DMF complex. This type of receptor is expected to be an effective host for poly-anionic guest species.

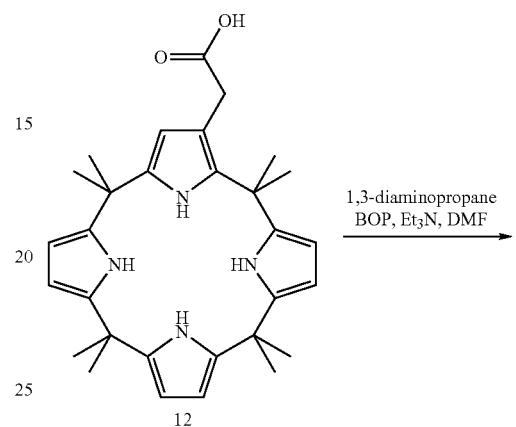

12

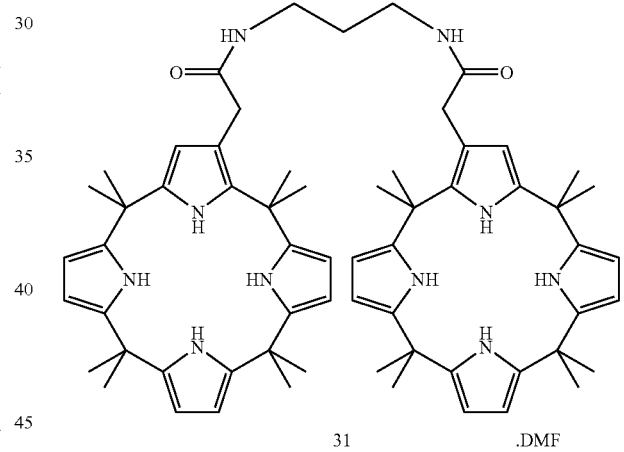

31 .DMF

Compound 12 (100 mg, 0.206 mmol) and 1,3-diamino-propane (7.62 mg, 0.103 mg) were dissolved in 5 mL DMF

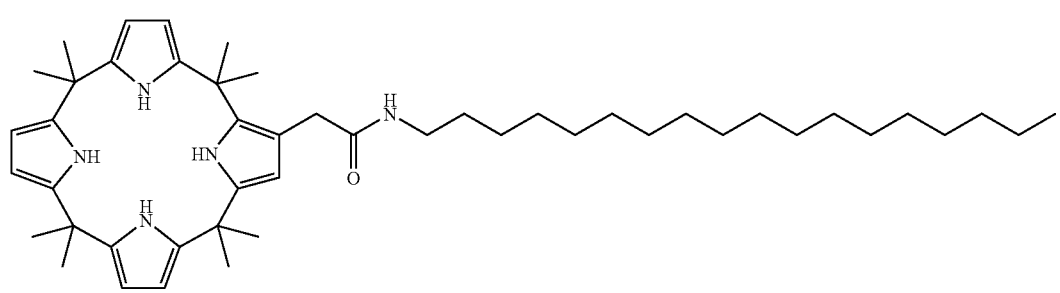

Figure 10:
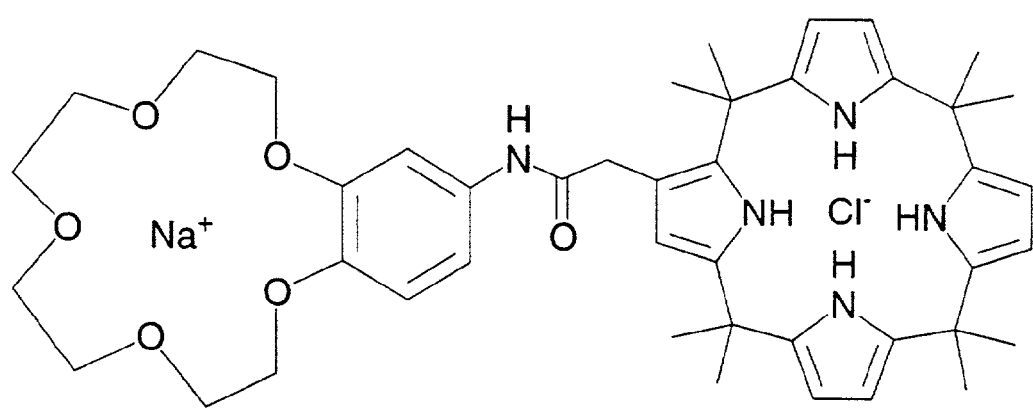
FIG. 10 illustrates a sodium chloride complex of calix[4]pyrrole-crown ether conjugate, 32.

30 under an argon atmosphere. BOP (109 mg, 0.247 mmol) and Et$_3$N (41 mg, 0.411 mmol) were added in 10 mL dry DMF, and the solution was stirred overnight. The solvent was then removed under high vacuum and the residue was purified by column chromatography (SiO$_2$, CH$_2$Cl$_2$–1.0% MeOH), affording the dimer 31 as a DMF complex (65 mg, 62%). $^1$H NMR (500 MHz, CD$_2$Cl$_2$) δ8.63 (s, 2H, NH), 7.93 (DMF), 7.35 (s, 2H, NH), 7.01 (s, 2H, NH), 6.35 (t, 2H, NH$_{amide}$), 5.88–5.67 (overlapping multiplets, 14H, CH$_{py}$), 3.51 (s, 4H, CCH$_2$), 3.25 (m, 4H, CH$_2$), 2.90 (DMF), 2.82 (DMF). High resolution FABMS calc for C$_{63}$H$_{82}$N$_{10}$O$_2$ 1010.6622; found 1010.6630 (Δ–0.7 ppm). This methodology can be extended to produce calixpyrrole trimers, networks of calixpyrroles, linear strings of calixpyrroles, or dendrimer type arrays of calixpyrroles. Additionally all these multimers could be synthesized using the meso-"monohook" acid 4 in a similar synthetic scheme as described herein for the β-substituted molecules.

β-Amidobenzo-15-crown-5-meso-octamethylcalix[4]pyrrole 32. 4'-Aminobenzo-15-crown-5 has been coupled to calix[4]pyrrole β-monoacid 12 to produce a ditopic receptor which is capable of binding a whole salt (i.e. Na$^+$—Cl$^-$) (FIG. 10) or a zwitterionic amino acid. The calixpyrrole provides an anion binding site and the crown ether a cation binding site, thereby providing a salt complexing agent.

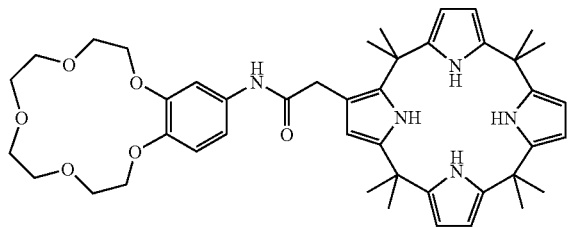

32 meso-Octamethylcalix[4]pyrrole β-monoacid 4 (281 mg, 0.58 mmol) and 4'-aminobenzo-15-crown-5 (164 mg, 0.58 mmol) were dissolved in dry DMF (20 mL) and stirred under an argon atmosphere. Benzotriazol-1-yloxytris(dimethylamino)phosphonium hexafluorophosphate (BOP PF$_6$) (0.306 g 0.69 mmol) and triethylamine (116 mg) in 20 mL DMF were added and the reaction mixture stirred overnight. The solvent was then removed under high vacuum and the residue purified by column chromatography (SiO$_2$, CH$_2$Cl$_2$–1 to 2% MeOH) affording the amide 32 as a white foam containing alkali metal cations (0.463 g). $^1$H NMR (250 MHz, CD$_2$Cl$_2$) δ: 8.74 (s, 1H, NH$_{py}$), 7.76 (s, 1H, NH$_{am}$), 7.45 (s, 1H, ArH), 7.34 (s, 1H, NH$_{py}$), 7.09 (s, 1H, NH$_{py}$), 7.02 (s, 1H, NH$_{py}$), 6.87 (m, 2H, ArH), 4.10 (m, 4H, 2OCH$_2$), 3.87 (m, 4H, 2OCH$_2$), 3.71 (m, 10H, 4OCH$_2$+CCH$_2$CO), 1.59 (s, 6H, 2CH$_3$), 1.57 (s, 6H, 2CH$_3$), 1.51 (s, 12H, 4CH$_3$). $^{13}$C NMR (62.5 MHz, CD$_2$Cl$_2$) δ: 171.48, 149.52, 145.96, 140.08, 139.56, 139.18, 138.78, 138.31, 138.14, 137.67, 134.48, 132.73, 114.66, 112.44, 109.97, 107.19, 106.91, 103.26, 103.13, 103.07, 102.83, 102.31, 101.71, 70.94, 70.40, 69.73, 69.57, 69.04, 37.12, 36.82, 35.45, 35.41, 35.19, 29.17, 28.97, 28.79. FABMS calc for C$_{44}$H$_{57}$N$_5$O$_6$ 751.4309; found 751.4310 (Δ–0.2 ppm). Further cation binding agents that may be coupled to calix[n]pyrrole include polyethers, texaphyrins and cryptands for example. Anion binding agents such as sapphyrin or other expanded porphyrins such as rubyrin, rosarin, amethyrin and turcasarin may also be appended to produce polyanionic receptors. Additionally neutral binding groups such as hydrogen bonding arrays may be appended to the calix[n]pyrrole.

Mono-meso-ferroceneamidocalix[4]pyrrole 33. The synthesis of new molecular devices designed to sense and report the presence of a particular substrate is an area of analytical chemistry which is attracting intense current interest. Ferrocene is a stable organometallic moiety that has been incorporated into meso- and β-pendant arms of calix[4]pyrrole macrocycles forming molecules which may be used as electrochemical sensors.

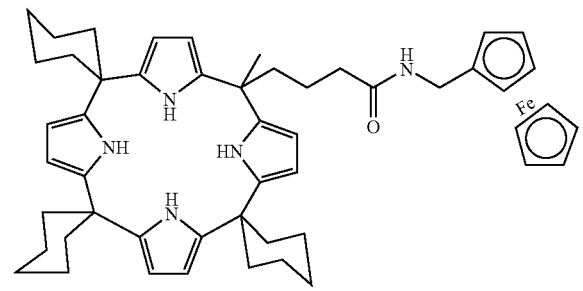

33

Compound 4 ('meso-hook' acid) (325 mg, 0.52 mmol) (see Example 2) was dissolved in DMF (20 mL, dry;) under an argon atmosphere. Methylaminoferrocene (112 mg, 0.52 mmol) was added followed by BOP PF$_6$ (278 mg, 0.63 mmol) and triethylamine (106 mg, 1.2 mmol). The reaction mixture was stirred for 48 hours. The DMF was then removed in vacuo and the product purified by column chromatography (SiO$_2$, CH$_2$Cl$_2$:CH$_3$OH 99:1 eluant) affording an orange foam 33 (288 mg, 67%). $^1$H NMR (250 MHz, CD$_2$Cl$_2$) δ: 7.24 (s, 2H, NH), 7.16 (s, 2H, NH), 5.93 (d, 4H, CH$_{py}$), 5.89 (d, 4H, CH$_{py}$), 5.61 (br.t, 1H, NH$_{amide}$), 4.16 (s, 7H, FcH+FcCH$_2$), 4.13 (m, 2H, FcH), 4.07 (m, 2H, FcH), 2.05 (t, 2H, CH$_2$), 1.94 (coincident resonances, 16H, 2CH$_2$ $_{hook}$+6CH$_2$ $_{cyclohexyl}$), 1.45 (br., 23H, CH$_2$ $_{hook}$ +CH$_3$+9CH$_2$ $_{cyclohexyl}$) $^{13}$C NMR (62.90 MHz, CD$_2$Cl$_2$) δ: 172.0, 137.6, 137.1, 137.0, 136.8, 104.0, 103.9, 103.8, 103.6, 85.7, 68.9, 68.5, 68.4, 40.0, 39.8, 39.5, 38.9, 38.8, 37.2, 37.1, 37.0, 36.9, 36.7, 26.4, 25.6, 23.2, 23.1, 20.9. High resolution FABMS calc for C$_{51}$H$_{63}$N$_5$O$^{56}$Fe 817.4382; found 817.4364 (Δ2.2 ppm).

Mono-β-ferroceneamidocalix[4]pyrrole 34. Compound 12 ('β-hook' acid) (250 mg, 0.51 mmol) was dissolved in DMF (20 mL, dry) under an argon atmosphere. Methylaminoferrocene (110 mg, 0.51 mmol) was added followed by BOP PF$_6$ (273 mg, 0.61 mmol) and triethylamine (105 mg, 1.03 mmol). The reaction mixture was stirred for 72 hours. The DMF was then removed in vacuo and the product purified by column chromatography (SiO$_2$, CH$_2$Cl$_2$:CH$_3$OH 99:1 eluant) affording an orange foam 34 (294 mg, 84%). $^1$H NMR (250 MHz, CD$_2$Cl$_2$) δ: 8.52 (s, 1H, NH), 7.38 (s, 1H, NH), 7.06 (s, 1H, NH), 7.01 (s, 1H, NH), 6.06 (s, 1H, NH$_{py}$), 5.91 (s, 6H, CH$_{py}$), 5.74 (1H, d, CH$_{py}$), 4.21 (m, 6H, FcH+FCCH$_2$), 4.14 (s, 5H, 5FcH), 3.54 (s, 2H, OCH$_2$), 1.58 (m, 12H, CH$_3$), 1.49 (m, 12H, CH$_3$). $^{13}$C NMR (62.90 MHz, CD$_2$Cl$_2$) δ: 172.6, 139.9, 139.4, 139.1, 138.9, 138.4, 138.3, 137.6, 134.3, 110.5, 107.1, 103.3, 103.2, 103.1, 102.9, 102.6, 102.1, 85.7, 68.9, 68.4, 68.3, 39.1, 37.1, 35.9, 35.5, 35.2, 29.2, 29.1. 29.0, 28.8. High resolution FABMS calc for C$_{41}$H$_{49}$N$_5$O$^{56}$Fe 683.3287; found 683.3280 (Δ1.0 ppm)

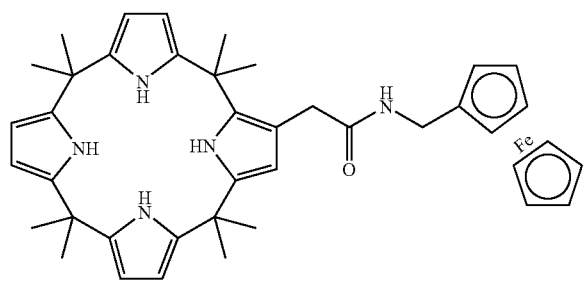

34

Figure 11A:
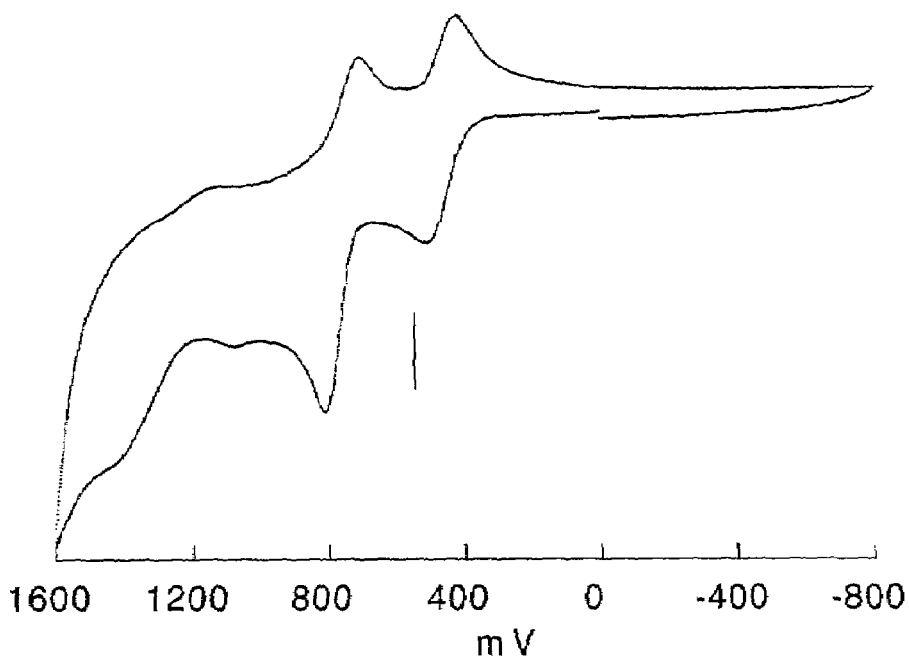
FIG. 11A illustrates a cyclic voltammogram of compound, 33, conducted in dichloromethane at a scan rate of 100 mV/sec. Working electrode: platinum disk, counter electrode: platinum wire, reference electrode: Ag/AgCl. 0.1 M tetrabutylammonium hexafluorophosphate as base electrolyte. Scale equals 2 microamps.
Figure 11B:
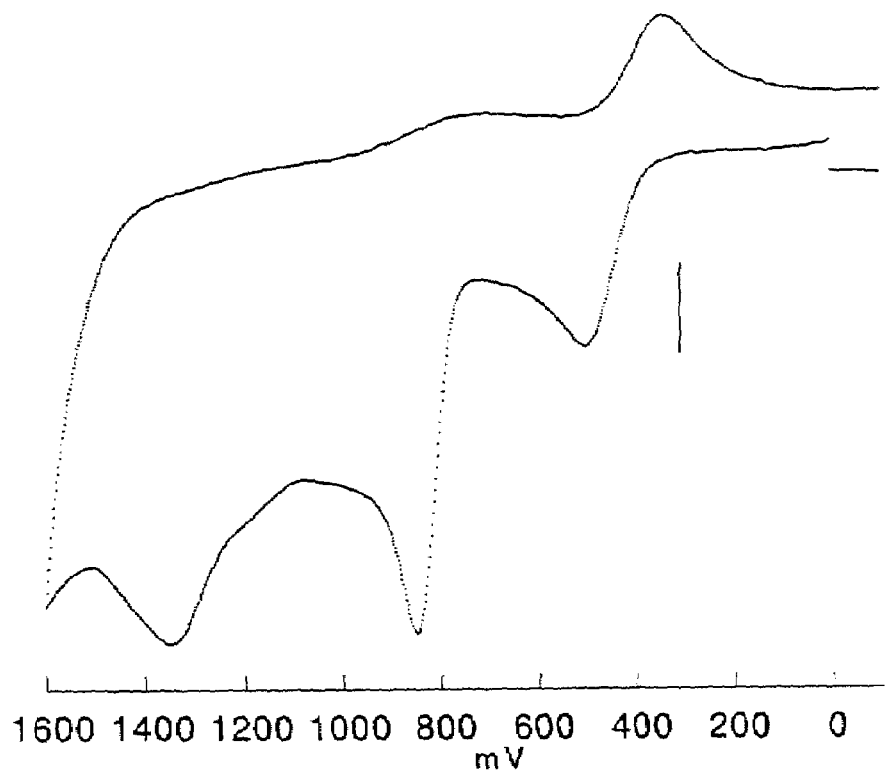
FIG. 11B illustrates a cyclic voltammogram of compound, 34, conducted in dichloromethane at a scan rate of 100 mV/sec. Working electrode: platinum disk, counter electrode: platinum wire, reference electrode: Ag/AgCl. 0.1 M tetrabutylammonium hexafluorophosphate as base electrolyte. Scale equals 2 microamps.
Figure 12A:
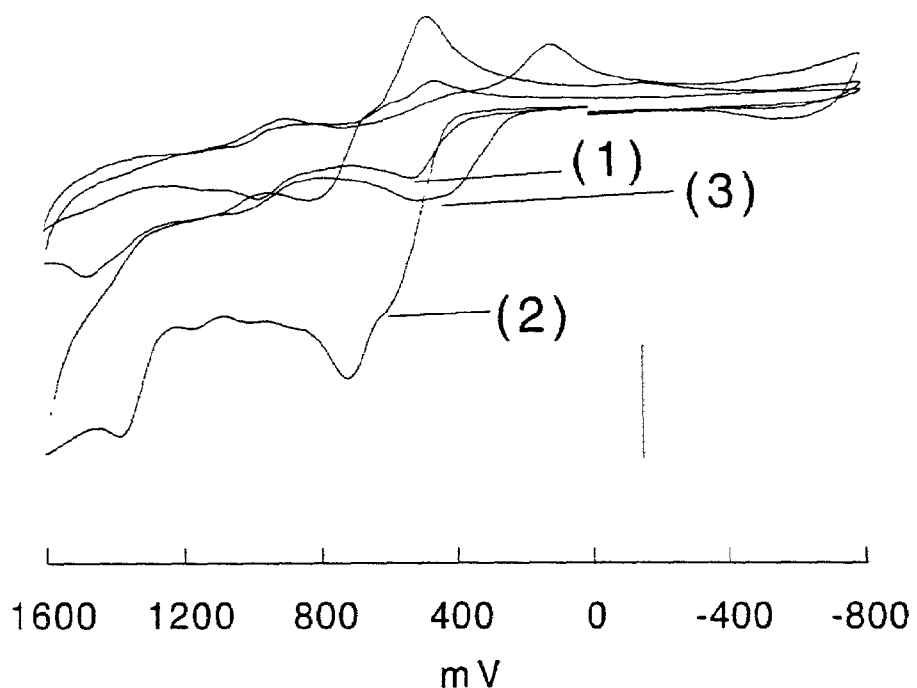
FIG. 12A illustrates a cyclic voltammogram of solutions of compound, 33, and 2 equivalents of tetrabutylammonium fluoride (1), tetrabutylammonium chloride (2), and tetrabutylammonium dihydrogenphosphate (3) conducted in dichloromethane at a scan rate of 100 mV/sec. Working electrode: platinum disk, counter electrode: platinum wire, reference electrode: Ag/AgCl. 0.1 M tetrabutylammonium hexafluorophosphate as base electrolyte. Scale equals 5 microamps.
Figure 12B:
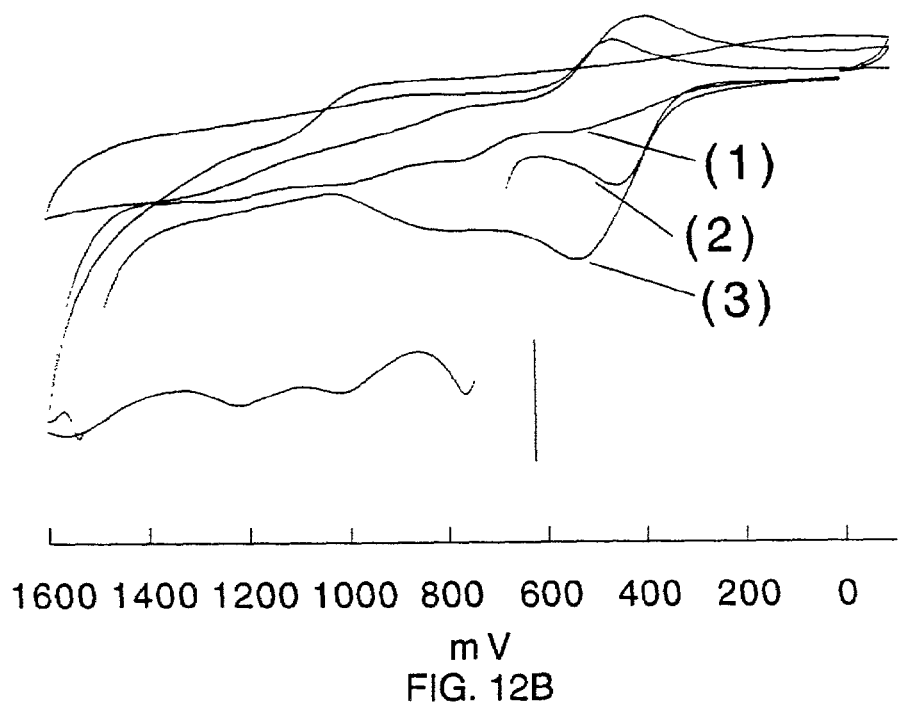
FIG. 12B illustrates a cyclic voltammogram of solutions of compound, 34, and 2 equivalents of tetrabutylammonium fluoride (1), tetrabutylammonium chloride (2), and tetrabutylammonium dihydrogenphosphate (3) conducted in dichloromethane at a scan rate of 1200 mV/sec. Working electrode: platinum disk, counter electrode: platinum wire, reference electrode: Ag/AgCl. 0.1 M tetrabutylammonium hexafluorophosphate as base electrolyte. Scale equals 5 microamps.

The electrochemical behavior of these macrocycles includes multiple oxidation processes occurring in the calixpyrrole ring. The ferrocene oxidation wave is distinct from these macrocycle oxidations and can be followed using standard electrochemical techniques (cyclic and square wave) (FIG. 11). The ferrocene oxidation wave is perturbed upon addition of anions to the electrochemical solution (FIG. 12) (Table 1).

TABLE 1

Redox potentials (mV) vs Ag/AgCl of the ferrocene moiety in compounds 33 and 34 in the absence and presence of anions (perturbation is shown in brackets) from square wave voltammetry

|  | Compound 33 (mV) | Compound 34 (mV) |
|---|---|---|
| Free ligand | 453 | 463 |
| $H_2PO_4^-$ | 401 (−52) | 430 (−33) |
| $F^-$ | 491 (+38) | 491 (+28) |
| $Cl^-$ | 530 (+77) | 410 (−53) |

Larger perturbations are observed for the meso-compound 33 than for the β-compound 34. It has been demonstrated that calixpyrroles can be incorporated into devices (in this case an electrochemical anion sensor) and operate successfully.

meso-Tetrakispolyethyleneglycol-meso-tetramethyl substituted calix[4]pyrrole 35. A polyethylene glycol derivative of calix[4]pyrrole has been synthesized 35.

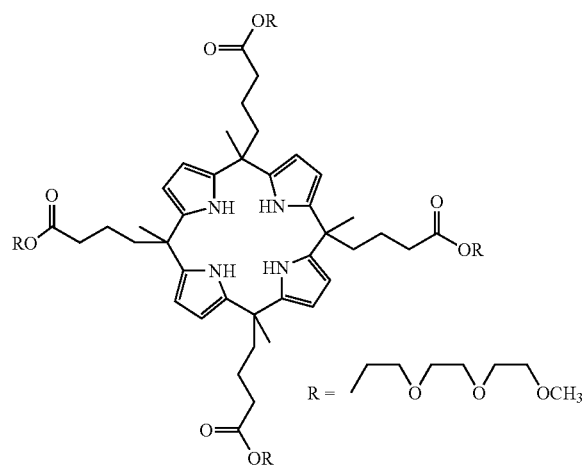

35

Reaction of 4-acetylbutyric acid with triethylene glycol monomethyl ether as solvent in the presence of HCl affords a water-soluble triethylene glycol ketone. Pyrrole (48 mg, 0.72 mmol) and the triethylene glycol ketone (200 mg, 0.72 mmol)) were dissolved in methanol (5 mL) and methanesulfonic acid (1 drop) added. The reaction was stirred overnight and the solvent then removed in vacuo affording the water soluble product 35 in 24% yield.

Preparation of amidosaccharide-calix[4]pyrrole conjugate 36. The coupling of protected glucosamine with calixpyrrole β-acid 12 derivative of calix[n]pyrrole produces a water soluble calixpyrrole conjugate. Calixpyrrole β-acid 12 (48.67 mg, 0.1 mmol) was dissolved in dry dichloromethane (50 mL) under argon and diisopropylcarbodiimide (2.5 molar equivalents, 0.25 mmol) was added together with 1 mg of 1-hydroxybenzotriazole. The solution was stirred for 10 minutes at room temparature under argon. 2-Amino-2-deoxy-1,3,4,6-tetraacetyl-β-D-glucopyranose hydrobromide salt (2 molar equivalents, 73 mg, 0.2 mmol) was added follwed by 0.3 mL of dry pyridine. The reaction mixture was stirred under argon for 3 days, diluted with dichloromethane (50 mL), washed with 3% hydrochloride acid, water and the organic phase dried over sodium sulfate. The product was isloated on short silica gel column with dichloromethane as eluant. The yield of calix[4]pyrrole 36 2-amido-2-deoxy-1, 3,4,6-tetra-O-acetyl-β-D-glucopyranose conjugate was 73.4 mg (90%). HR MS for $C_{44}H_{58}N_5O_{10}$ calc. 816.4184, found. 816.4178. Deprotection of the tetraacetylated derivative was performed using standard procedures by dissolution of the protected sugar calix[4]pyrrole conjugate described above (50 mg) in MeOH, with catalytic amount of sodium methoxide. The solution was stirred for 8 hours at room temperature. The product, calix[4]pyrrole 2-amido-2-deoxy-β-D-glucopyranose 37 conjugate, was obtained in quantitative yield. For $C_{36}H_{49}N_5O_6$ calc 647.36826, found 647.36802.

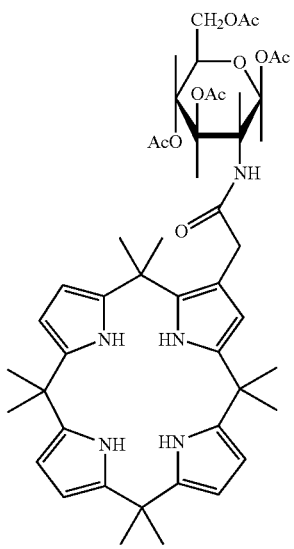

36

-continued

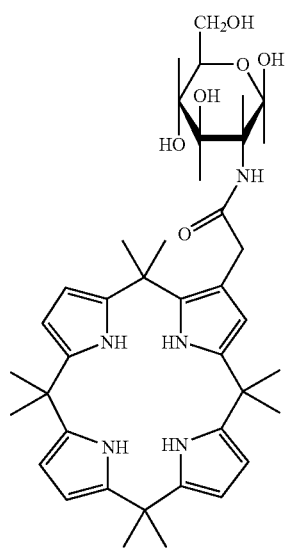

37

A host of hydrophilic substituents can be coupled to β-mono-acid and meso-mono-acid: for example, polyethylene glycols, azacrown ethers, crown ethers, phosphate groups, saccharides, modified sugars bearing amino groups, amino alcohols sulfonyl, chitosan, 2-aminoethylhydrogensulfate, 2-aminoethylphosphoric acid, and the like. Additionally, water solublizing groups, such as sulfonates, phosphates, polyalcoholis, polyethers, hydroxyl groups, amino groups, carboxylic acid groups, sulfoxide groups, and other could be incorporated into the molecule via attachment to the starting ketone and pyrrole before formation of the macrocycle.

Calix[n]pyrroles have been shown to bind phosphate groups in the solid state, in solution, and when bound to solid supports as described in Example 10. DNA and RNA, important biological molecules, contain many phosphate groups. A water-soluble calix[n]pyrrole is expected to bind to DNA and RNA. Binding could have the effect of limiting the ability to unwind in the case of DNA, thereby hindering biological functions, or in the case of RNA, could prevent translation. Additionally, oligonucleotides having sequence complementarity to a template molecule may be attached to a calix[n]pyrrole for site-specificity. Uses include inhibition of replication and anti-sense therapy.

EXAMPLE 9

Chiral Calix[n]pyrroles, Calix[m]pyridino[n]pyrroles, and Calix[m]pyridines

The present example provides methods for inducing chirality in macrocycles of the present invention, and provides chiral macrocycles for recognition and separation of neutral and anionic chiral molecules. One of skill in this art, in light of the present disclosure, would realize that the methods provided herein for calixpyrroles are applicable to calix[m]pyridino[n]pyrroles, and calix[m]pyridines.

A first method is to use chiral molecules as starting materials for the synthesis of calix[n]pyrroles. A second method is to attach optically active (chiral) groups to the molecule via bond formation between functional groups on the calix[n]pyrrole and the chiral auxiliary. A third method is based on transforming achiral substituents into chiral groups by using, for instance, chiral catalysis.

Exemplary chiral ketones that can be used to synthesize chiral calixpyrroles include, but are not limited to, chiral ketone containing steroid derivatives, antibiotics e.g. lasalocid, synthetic chiral ketones, and binaphthal groups that possess an inherent chirality. Steroid analogs have the added advantage of forming bowl-shape cavities because of the natural bend in the molecule. They have well defined geometries and can act as receptors for anions (e.g. 38).

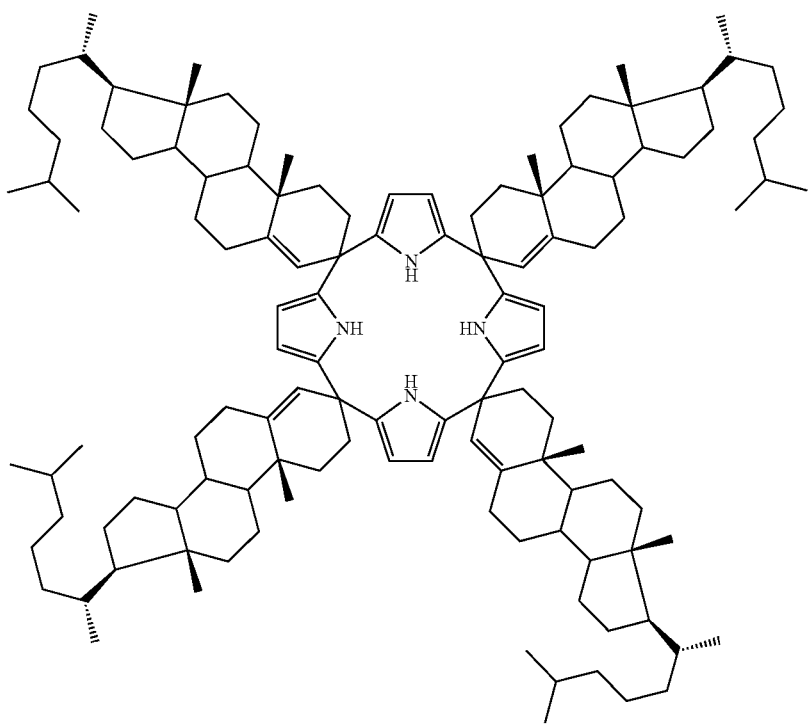

38

Preparation of steroidal calix[n]pyrroles. 4-Cholesten-3-one (38.4 mg, 0.1 mmol) was dissolved in 25 mL of ethanol. Ten molar equivalents of pyrrole was added to the solution. The solution was cooled to 0° C. and 10 mg of concentrated HCl in 1 mL of ethanol was added to the reaction mixture which was then stirred for 24 hrs, at room temperature. The solvent was removed in vacuo. The residue was redissolved in dichloromethane (25 mL) and washed with a 3% sodium carbonate solution. The product 38 was purified by flash chromatography on silica gel using a dichloromethane-hexane (1:1) mobile phase. Yield=12%. The main product was a calix[4]pyrrole $(C_{31}H_{47}\%)_4$ Calc'd Mass: 1734. Found: 1734. For calix[5]pyrrole $(C_{31}H_{47}N)_5$ Calc'd Mass: 2167. Found: 2167. This reaction has been repeated varying the ratio of ketone to pyrrole and also varying the type of acid used. The total yields of calix[n]pyrroles predominantly but not exclusively the n=4 product, were generally in the 10–15% range.

Because of their many functional groups, steroid-substituted calix[n]pyrroles containing functional groups capable of being attached to solid supports are likely to exhibit enantioselective separation of, for example, sugars, synthetic oligonucleotides, polypeptides, chiral anions, chiral neutral molecules, or the like. One skilled in the art, in the light of the present disclosure, would appreciate that the resulting species would be amenable to attachment to a solid support.

Binaphthal system also possess an inherent chirality. Being so close to the periphery, they could act as "directing groups" and influence binding of neutral and anionic species e.g. 39.

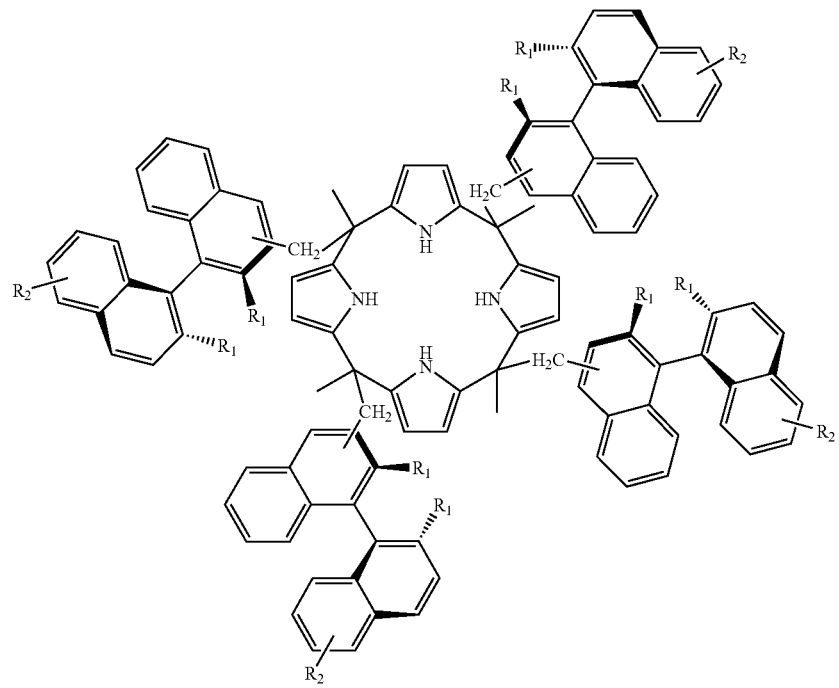

A second method for inducing chirality in a molecule is to attach a chiral auxiliary to the main body of the calix[n]pyrrole. This could be done, for example, by forming an amide bond between a carboxycalix[n]pyrrole and a chiral, amino group-containing molecule. This can include, but is not limited to, aminoglycosides, chiral amino alcohols, aminocyclodextrins and amino acids. Many different kinds of functional groups can be coupled to form chemical bonds with a calix[n]pyrrole and would be known in the light of the present disclosure. One skilled in the art, in the light of the present disclosure, would appreciate that the resulting species would be ammenable to attachment to a solid support.

Chiral Amide β-Substituted calix[4]pyrrole 40. Monoacid 12 has been coupled to a number of different amines to produce chiral and dimer calixpyrrole species. (R)-(+)-α-methylbenzylamine is a readily available chiral amine. This amine was appended to the calixpyrrole skeleton by conducting an amide coupling reaction between the amine and compound 12 in the presence of BOP and Et$_3$N in DMF solution. The amide was isolated as a DMF complex.

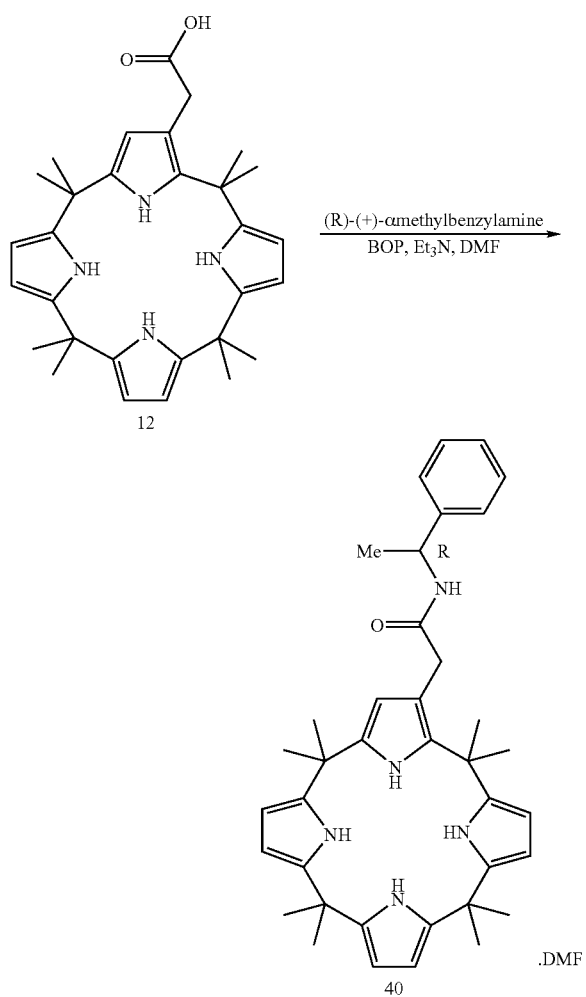

Figure 13:
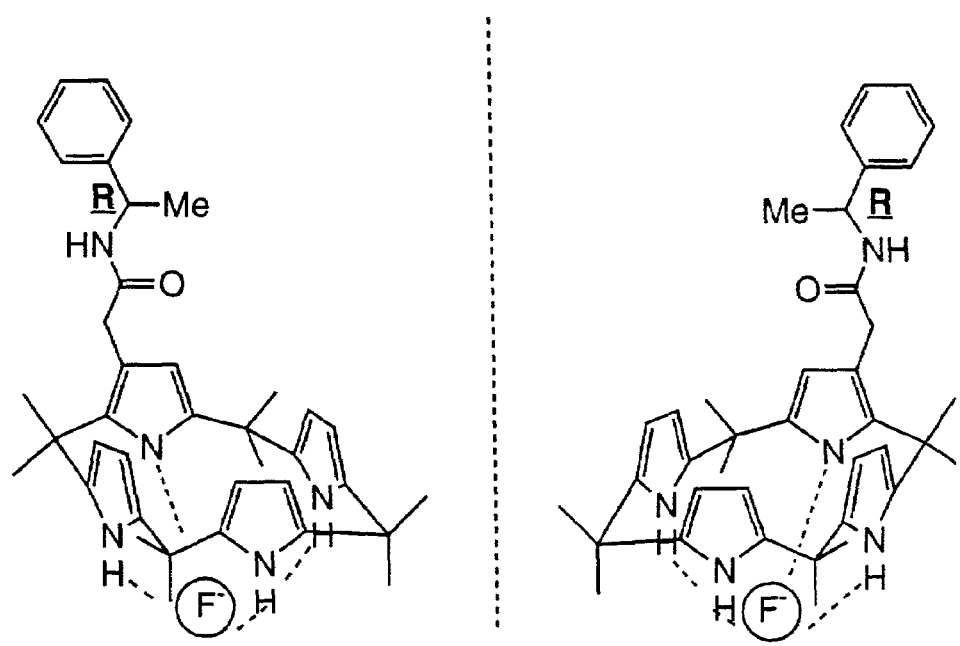
FIG. 13 illustrates a calix[4]pyrrole-R-(+)-a-methylbenzylamine conjugate, 40, -fluoride complex represented as a diastereomeric mixture.

Chiral calixpyrroles are useful in the chiral separation of racemic mixtures of species such as amino acids. Compound 40 will form a diastereomeric mixture when complexed to fluoride (FIG. 13).

Compound 12 (200 mg, 0.41 mmol) and (R)-(+)-α-methylbenzylamine (50 mg, 0.41 mmol) were dissolved in dry DMF (10 mL) and stirred under an argon atmosphere. Benzotriazol-1-yloxytris(dimethylamino)phosphonium hexafluorophosphate (BOP) (0.218 g, 0.494 mmol) and triethylamine (83 mg, 0.82 mmol) in 15 mL DMF were added, and the reaction mixture was stirred overnight. The solvent was then removed under high vacuum and the residue was purified by column chromatography (twice on SiO$_2$, CH$_2$Cl$_2$–2.5% MeOH), affording the chiral amide 40 as a DMF complex (161 mg, 66% yield). $^1$H NMR (250 MHz, CD$_2$Cl$_2$) δ: 8.76 (s, 1H, NH), 7.95 (DMF), 7.33–7.28 (m, 5H, PhH), 7.16 (s, 1H, NH), 6.96 (2 br s, 2H, NH), 5.86–5.65 (overlapping multiplets, 7H, CH$_{py}$), 5.09 (m, 1H, PhCH), 3.50 (s, 2H, CCH$_2$), 2.90 (DMF). 2.81 (DMF), 1.54–1.45 (overlapping singlets, 27H, CH$_3$). High resolution FABMS calc for C$_{38}$H$_{47}$N$_5$O$_1$, 589.3781; found 589.3768 (Δ2.2 ppm).

The third method of inducing chirality is reaction of a non-chiral substituent, such as an alkene, to form a chiral side chain and subsequent anti-selective transformation of the side chain to a chiral moiety. These types of reactions include, but are not limited to, catalytic asymmetric hydrogenation, asymmetric epoxidation and subsequent ring opening, asymmetric diol formation, asymmetric halogenation and asymmetric amino alcohol formation.

EXAMPLE 10

Calix[n]pyrroles, Calix[m]pyridino[n]pyrroles and Calix[m]pyridines for Solution and Solid Support Binding, and for Separation of Ionic and Neutral Substrates Calix[n]pyrroles and calix[m]pyridino[n]pyrroles for binding and separation possess a pyrrolic hydrogen bonding array capable of coordinating anions via N—H . . . anion hydrogen bonds. Calix[m]pyridines have a lone pair of electrons on pyridine nitrogens that are capable of donating electron density to a cation. Further, a protonated calix[m]pyridine is capable of electrostatically interacting with an anion. Anion binding properties of calixpyrroles have been studied in solution using $^1$H NMR titration techniques and are provided herein.

Stability constants for octamethylcalix[4]pyrrole, 1, and tetraspirocyclohexylcalix[4]pyrrole, 2, binding to various anions in dichloromethane were obtained and are provided in Table 2.

TABLE 2

Stability constants for compounds 1 and 2 with anionic substrates[a]

| | Stability Constant (M$^{-1}$) | |
|---|---|---|
| | Calixpyrrole 1 | Calixpyrrole 2 |
| Fluoride[b] | 17170 (±900) | 3600 (±395) |
| Chloride | 350 (±5.5) | 117 (±4.0) |
| Bromide | 10 (±0.5) | c |
| Iodide | <10 | c |
| Dihydrogen phosphate | 97 (±3.9) | <10 |
| Hydrogen sulfate | <10 | c |

[a]Anions were added as 0.1 M CD$_2$Cl$_2$ solutions of their tetrabutylammonium salts to receptor to 10 mM receptor solutions in CD$_2$Cl$_2$ with concentration changes being accounted for by EQNMR.
[b]Tetrabutylammonium fluoride was added as the trihydrate.
[c]Undetermined.

The data of Table 2 demonstrate that calix[4]pyrroles show different affinity for different anions in solution, with fluoride being the most tightly bound while iodide is very slightly bound.

The present inventors have discovered that varying the substituents on the β-position of a calixpyrrole molecule, however, affects the strength with which a particular anion is held. The data of Table 3 shows the effect of substituting the β-positions of the macrocycle with ester 10, methoxy 13, and bromine 14 groups and the effect that these functional groups have on the binding strength of calix[4]pyrrole to various anions. Additionally compound 11 has been shown to interact with both fluoride and chloride anions in solution.

TABLE 3

Stability constants for compounds 10, 13 and 14 with anionic substrates[a] in $CD_2Cl_2$

| | Stability Constant ($M^{-1}$) | | |
|---|---|---|---|
| | 10 | 13 | 14 |
| Fluoride | 1.1 (±0.2) × 10³ | 1.7 (±0.2) × 10² | 2.7 (±0.4) × 10⁴[b] |
| Chloride | 47 (±1) | <10 | 4.3 (±0.6) × 10³ |
| Dibiphosphate | c | 6.5 (±0.4) × 10² | <10 |

[a]Anions were added as 0.03 M $CD_2Cl_2$ solutions of their tetrabutylammonium salts to 3 mM solutions of the receptor in $CD_2Cl_2$ with concentration changes being accounted for by EQNMR. In determining the stability constants, the possible effects of ion pairing (if any) were ignored.
[b]Estimated value. The NH proton resonance broadened considerably during the titration, forcing the frequency of the resonance to be noted manually.
[c]Not determined.

The attachment of electron-donating substituents (such as methoxy) to the β-position (carbon or C-rim of the calixpyrrole) decreases the stability constants of compound 13 relative to compound 2. However attachment of electron-withdrawing substituents (such as bromine) to the carbon-rim has increased the stability constants of compound 14 relative to compound 1.

While varying the electron density of the calix[4]pyrrole core increases or decreases the binding affinities towards anions, the present inventors also discovered that groups having a functional moiety at a suitable distance from the macrocycle, and having sufficient flexibility to fold back over the macrocycle also affects the strength of binding as discussed below. The data of Table 4 illustrate the effects of an amide group attached at the meso-position of the calix[4]pyrrole.

TABLE 4

Stability constants for compounds 28 and 29 with anionic substrates in $CD_2Cl_2$

| | Stability Constants ($M^{-1}$) | |
|---|---|---|
| | Compound 28 (β) | Compound 29 (meso) |
| Chloride | 405 (±10) | 415 (±45) |
| Dihydrogen phosphate | 80 (±15)[b] | 62 (±6) |
| Hydrogen sulfate | <10 | <10 |

[a]Anions were added as 0.1 M $CD_2Cl_2$ solutions of their tetrabutylammonium salts to 10 mM solutions of the receptor in $CD_2Cl_2$ with concentration changes being accounted for by EQNMR. In determining the stability constants, the possible effects of ion pairing (if any) were ignored.
[b]Estimated value. The NH proton resonance broadened considerably during the titration, forcing the frequency of the resonance to be noted manually.

Figure 14:
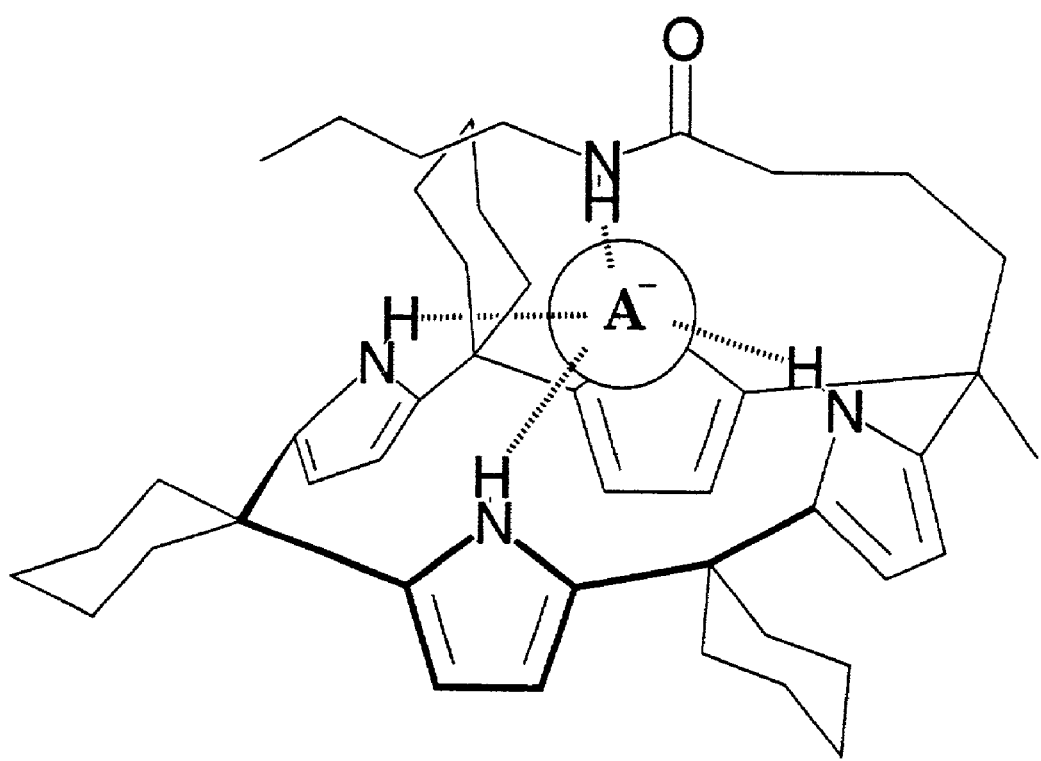
FIG. 14 illustrates the hydrogen bond donating capabilities of a meso-mono-butylamidotrispirocyclohexylcalix[4]pyrrole, 28, complexed to an anion.

As compared to meso-tetraspirocyclohexylcalix[4]pyrrole. 2, the meso-substituted, amide-substituted calix[4]pyrrole 29 shows a marked increase in binding affinities for chloride and phosphate when compared with the values obtained for tetraspirocyclohexyl calix[4]pyrrole (see Table 2). The amide group contributes to the binding of the anion via an amide-anion hydrogen bond as shown in FIG. 14.

This increased binding affinity towards anions was not observed for the β-substituted amide substituted meso-octamethylcalix[4]pyrrole 28 when compared to the compound 1. A possible reason is that the carboxy "tail" is not long enough to swing around and contribute to the binding of the anion.

TABLE 5

Stabiltity constants of the ferrocene-substituted calix[4]pyrroles 33 and 34, measured in $CD_2Cl_2$.

| Anion | 33 meso-ferrocene | 34 β-ferrocene |
|---|---|---|
| $H_2PO_4$ | 40 ± 6 $M^{-1}$ (β-CH) | 40 ± 9 $M^{-1}$ |
| F | 79 ± 7 $M^{-1}$ (β-CH) | 1496 ± 370 $M^{-1}$ |
| | 206 ± 51 $M^{-1}$ (NH) | |
| Cl | 202 ± 15 $M^{-1}$ | 444 ± 22 $M^{-1}$ |

The ferrocene modified calixpyrrole binding constants with anions are provided in Table 5.

Substrate Binding in Solution. The binding of neutral molecules to calix[4]pyrrole in the solid state prompted the present inventors to quantify the binding affinities of calix[4]pyrrole to a number of hydrogen-binding neutral molecules. Table 6 illustrates the varying degrees of affinity to which calix[4]pyrrole binds to various hydrogen binding compounds.

TABLE 6

Association Constants for Calix[4]pyrrole, 1, with Neutral Substrates[a]

| Substrate Added | $K_a$ ($M^{-1}$) |
|---|---|
| methanol | 12.7 ± 1.0 |
| ethanol | 10.7 ± 0.7 |
| benzyl alcohol | 9.7 ± 0.7 |
| isopropyl alcohol | 7.0 ± 0.4 |
| sec-butanol | 6.2 ± 0.4 |
| N-formylglycine ethyl ester | 13.3 ± 1.0 |
| N,N-dimethylformamide | 11.3 ± 0.8 |
| N,N-dimethylacetamide | 9.0 ± 0.9 |
| 1,1,3,3-tetramethylurea | 2.2 ± 0.1 |
| dimethyl sulfoxide | 16.2 ± 1.1 |
| 1,2-dimethylimidazole | 5.4 ± 0.3 |
| acetone | 2.2 ± 0.2 |
| nitromethane[b] | — |

[a]In benzene-$d_6$ at 298 K. For each titration, the concentration of 1 was held constant (at ca. 4 × 10⁻³ M) as aliquots of the substrate in benzene-$d_6$ (ca. 1 M) were added.
[b]In this instance, the induced shifts in the NH proton(s) of 1 were too small (<0.15 ppm) to afford a reliable $K_a$ value.

The data in Table 6 demonstrates the ability of calixpyrroles to coordinate to neutral species Separation using Solid-Supported Calix[4]pyrroles. Following the discovery of the unique anion binding capabilities of calix[4]pyrroles, the present inventors proceeded to attach the "monohook" of Examples 2 and 3 to a silica gel solid support. Calix[4]pyrrole-substituted silica gel chromatography has demonstrated the ability to separate anionic, neutral hydrogen-binding and aromatic molecular species. In addition to anionic species such as phenyl phosphate, calix[4]pyrrole substituted silica gel has demonstrated the ability to separate polyphosphate-containing compounds such as 5'-adenosine mono-, di-, and triphosphate under standard, isochratic HPLC conditions at pH=7. As one might expect, increasing the number of anionic binding sights greatly increases the retention times of these types of molecules.

Figure 15A:
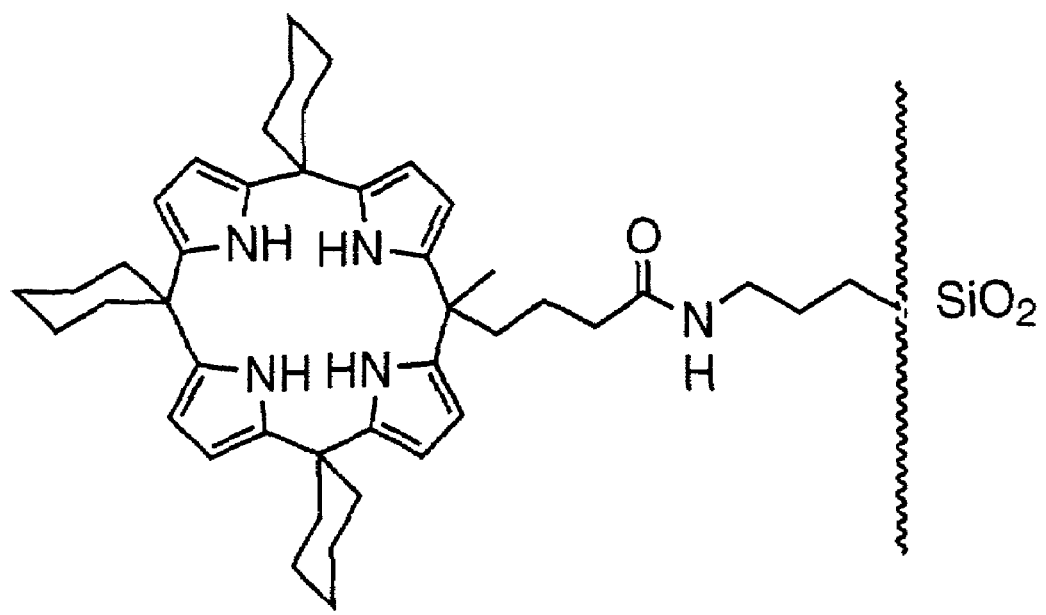
FIG. 15A illustrates mesosubstituted-calix[4]pyrrole substituted silica gel, M.
Figure 15B:
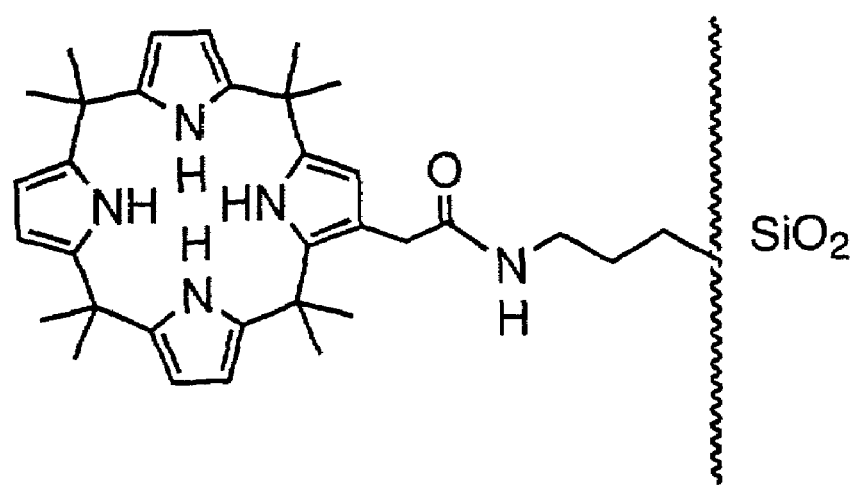
FIG. 15B illustrates β-substituted-calix[4]pyrrole substituted silica gel, B.

The present approach to anionic and neutral species separation was as follows. The macrocycle, meso-tris-spirocyclohexyl-monohook-calix[4]pyrrole, 4, was covalently attached to 5μ, trimethyl silyl protected, aminopropyl HPLC-grade silica gel obtained from Phase Separations (Norwalk, Conn.) to produce Gel M as shown in FIG. 15A. In a similar fashion, β-monohook acid calix[4]pyrrole 12 was attached to 5μ, trimethyl silyl protected, aminopropyl HPLC-grade silica gel obtained from Phase Separations (Norwalk, Conn.) in the presence of diisopropylcarbodiimide to produce Gel B as shown in FIG. 15B. The attachment of the "monohook" calix[4]pyrrole to C-1 aminopropyl silica gel is achieved in a greater than 95% yield.

Figure 16:
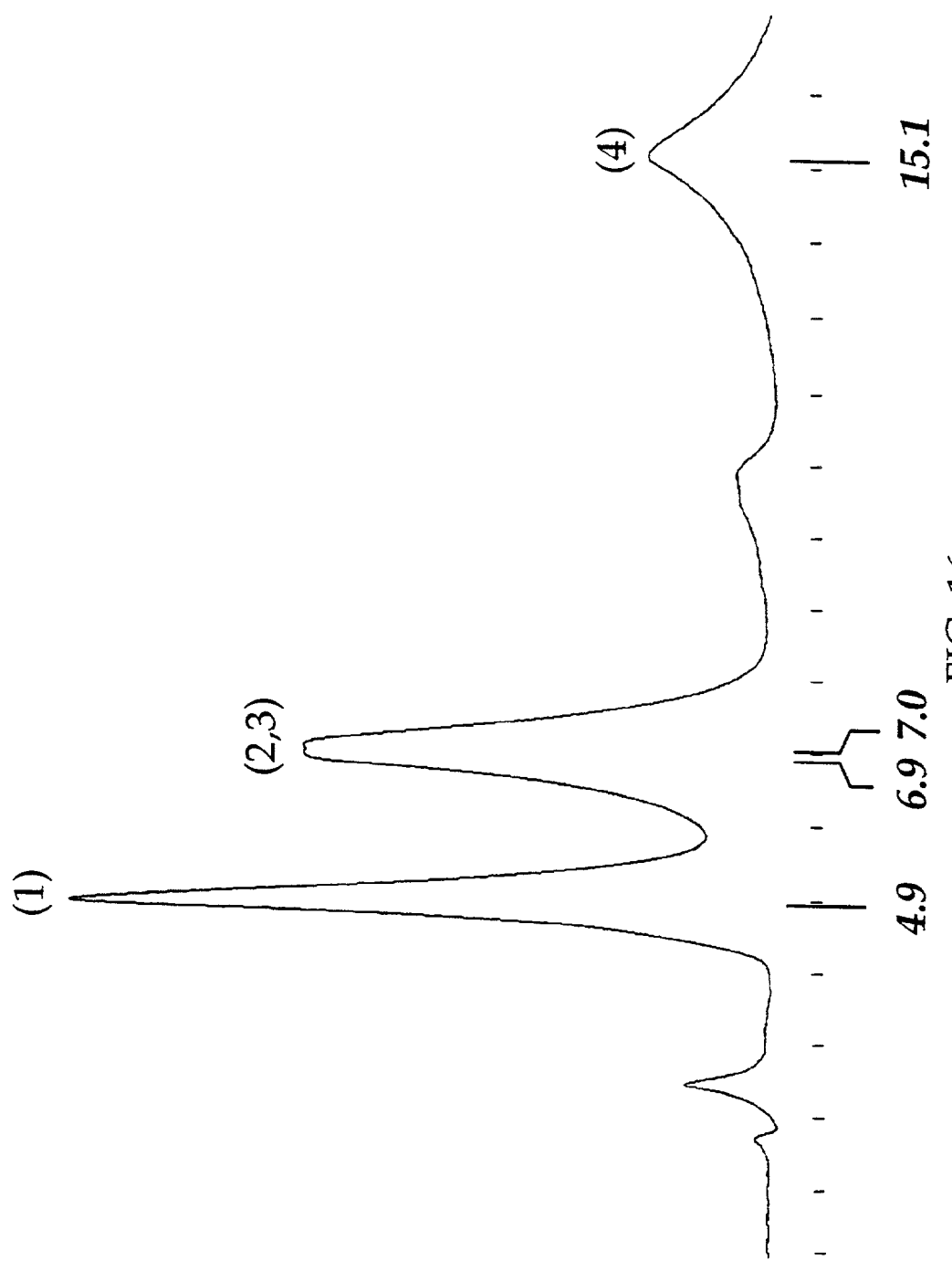
FIG. 16 illustrates the separation of phenyl arsenate (1), benzene sulfonate (2), benzoate (3), and phenyl phosphate (4) on a meso-substituted calix[4]pyrrole column: mobile phase, 50 mM phosphate buffer, pH=7.0: flow rate 0.3 mL/min.; column temperature 25° C.; detection 254 nm (0.100 AUFS).
Figure 17:
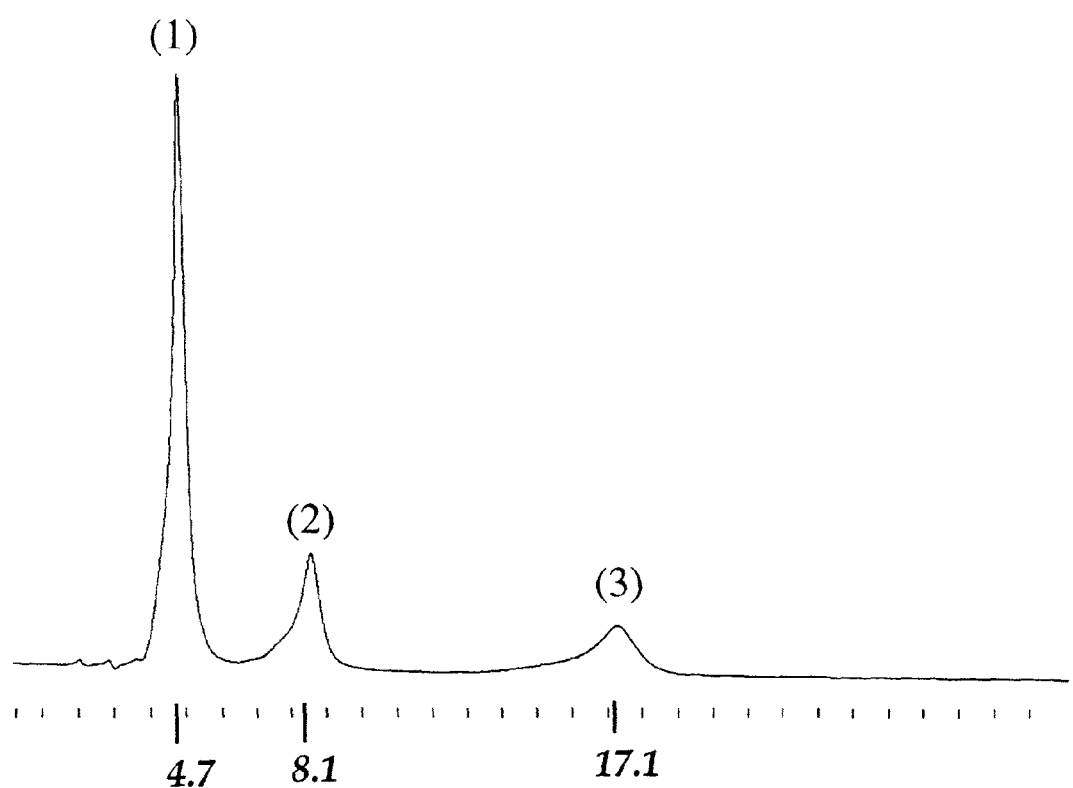
FIG. 17 illustrates the separation of 5'-adenosine monophosphate (1), 5'-adenosine diphosphate (2), and 5'-adenosine triphosphate (3) on a meso-substituted calix[4]pyrrole column: mobile phase 250 mM phosphate buffer, pH=7.0; flow rate 0.3 mL/min.; column temperature 25° C.; detection 254 nm (0.100 AUFS).
Figure 18:
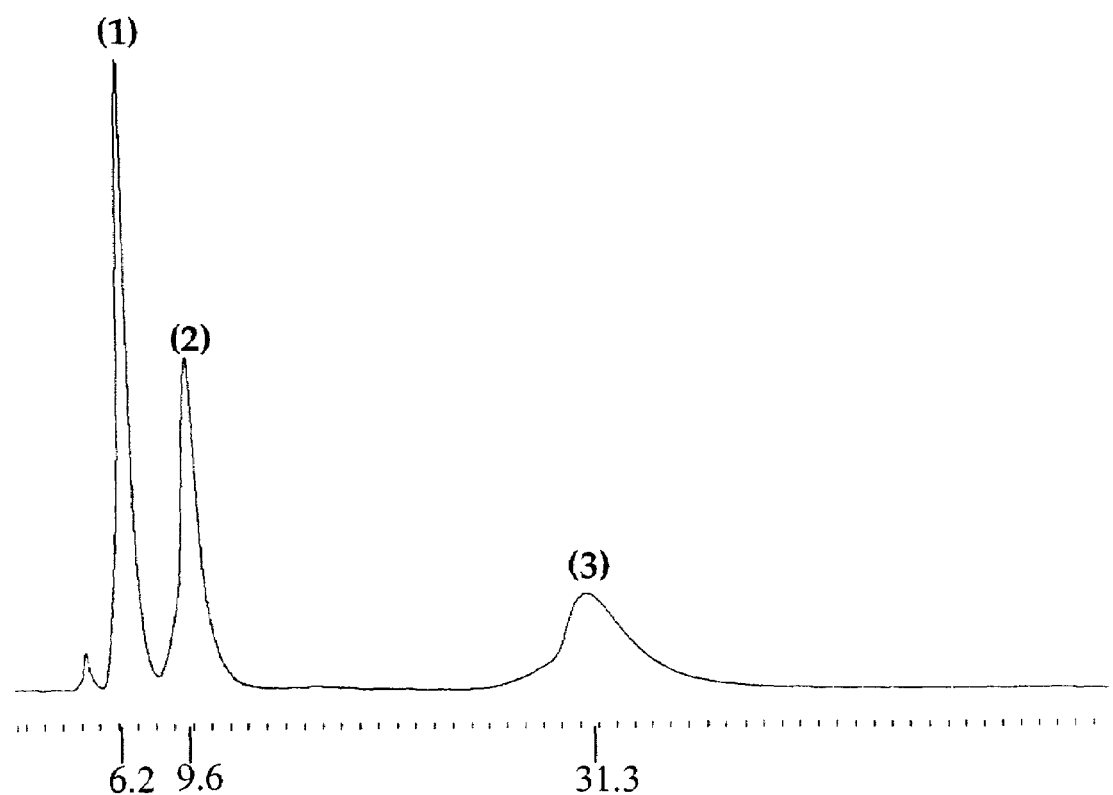
FIG. 18 illustrates the separation of 5'-adenosine monophosphate (1), 5'-adenosine diphosphate (2), and 5'-adenosine triphosphate (3) on a β-substituted calix[4]pyrrole column: mobile phase 105 mM phosphate buffer, pH=7.0; flow rate 0.20 mL/min.; column temperature 25° C.; detection UV at 254 nm (0.100 AUFS).

The calix[4]pyrrole columns were packed commercially by Alltech (Deerfield, Ill.), and various substrates, under differing conditions, were eluted through the columns. All of the data provided in the chromatograms herein were obtained at room temperature under isochratic conditions. FIG. 16 illustrates the separation of phenyl sulfonate (3), phosphate (4), arsenate (1), and benzoic acid (2) on Gel M. Excellent selectivity is seen among the different anions. FIG. 17 and FIG. 18 provide further examples of separation of biologically-relevant substrates by the calix[4]pyrrole-substituted silica gel, in this case, 5'-adenosine monophosphate, 5'-adenosine diphosphate and 5'-adenosine triphosphate. The nucleotides described elute in ascending order according to the number of phosphate groups contained within the molecule (i.e. the substrates containing the more anionic groups are retained longer on the column relative to substrates containing fewer anionic groups). Selectivity for carboxylates was also observed for carboxy-substituted benzenes. In two separate experiments, calix[4]pyrrole substituted silica gel, B, effectively separated benzoic acid, isophthallic acid, and 1,3,5-tricarboxy benzene. In a separate experiment, a calix[4]pyrrole substituted silica gel column effectively separated phthallic acid from a mixture of teraphthallic acid, isophthallic acid and phthallic acid.

Figure 20:
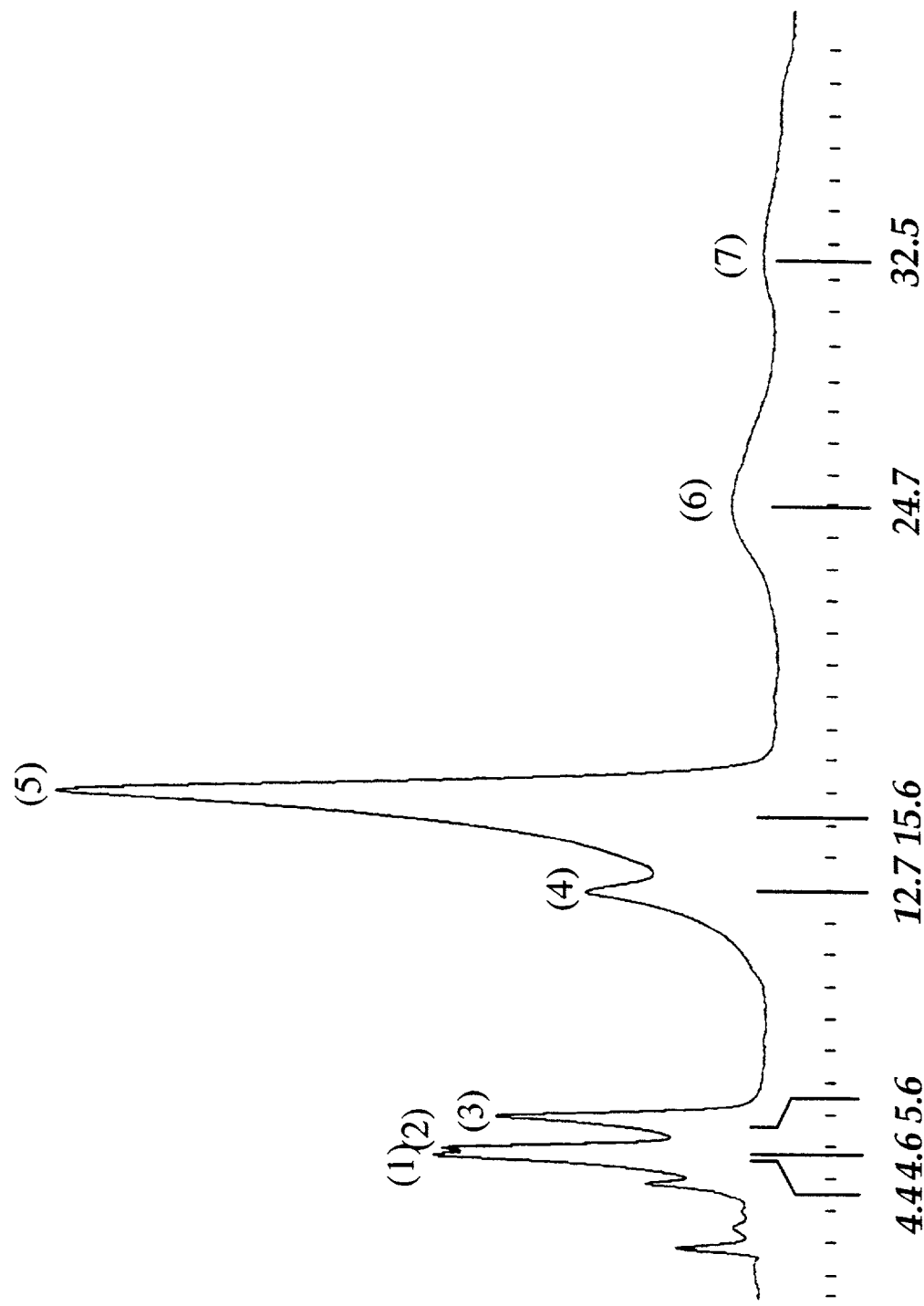
FIG. 20 illustrates the separation of Cbz-N-protected-serine (1), glutamine (2), alanine (3), phenylalanine (4), tryptophan (5), aspartate (6), and glutamate (7) on a meso-substituted calix[4]pyrrole column: mobile phase 70% 30 mM acetate buffer, pH=7.0/30 % $CH_3CN$ (v/v); flow rate 0.3 mL/min.; column temperature 25° C., detection 254 nm (0.100 AUFS).
Figure 21:
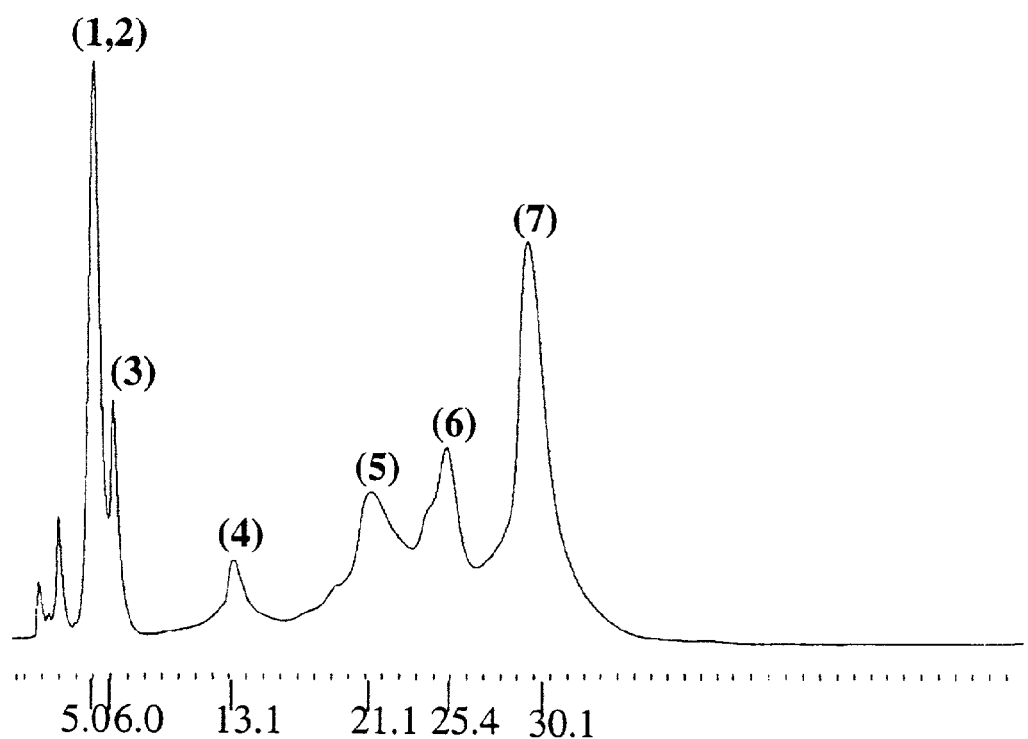
FIG. 21 illustrates the separation of Cbz-N-protected-serine (1), leucine (2), alanine (3), phenylalanine (4), tryptophan (5), aspartate (6), and glutamate (7) on a β-substituted calix[4]pyrrole column: mobile phase 75/25 30 mM acetate buffer, pH=7.0/acetonitrile; flow rate 0.20 mL/min.; column temperature 25° C.; detection UV at 254 nm (0.100 AUFS).

FIG. 20 and FIG. 21 demonstrate the separation of carboxybenzyl-N-protected amino acids on Gel M and Gel B, respectively. These data illustrate that both hydrophobic contributions and hydrogen bonding interactions are involved in the separation.

Figure 19:
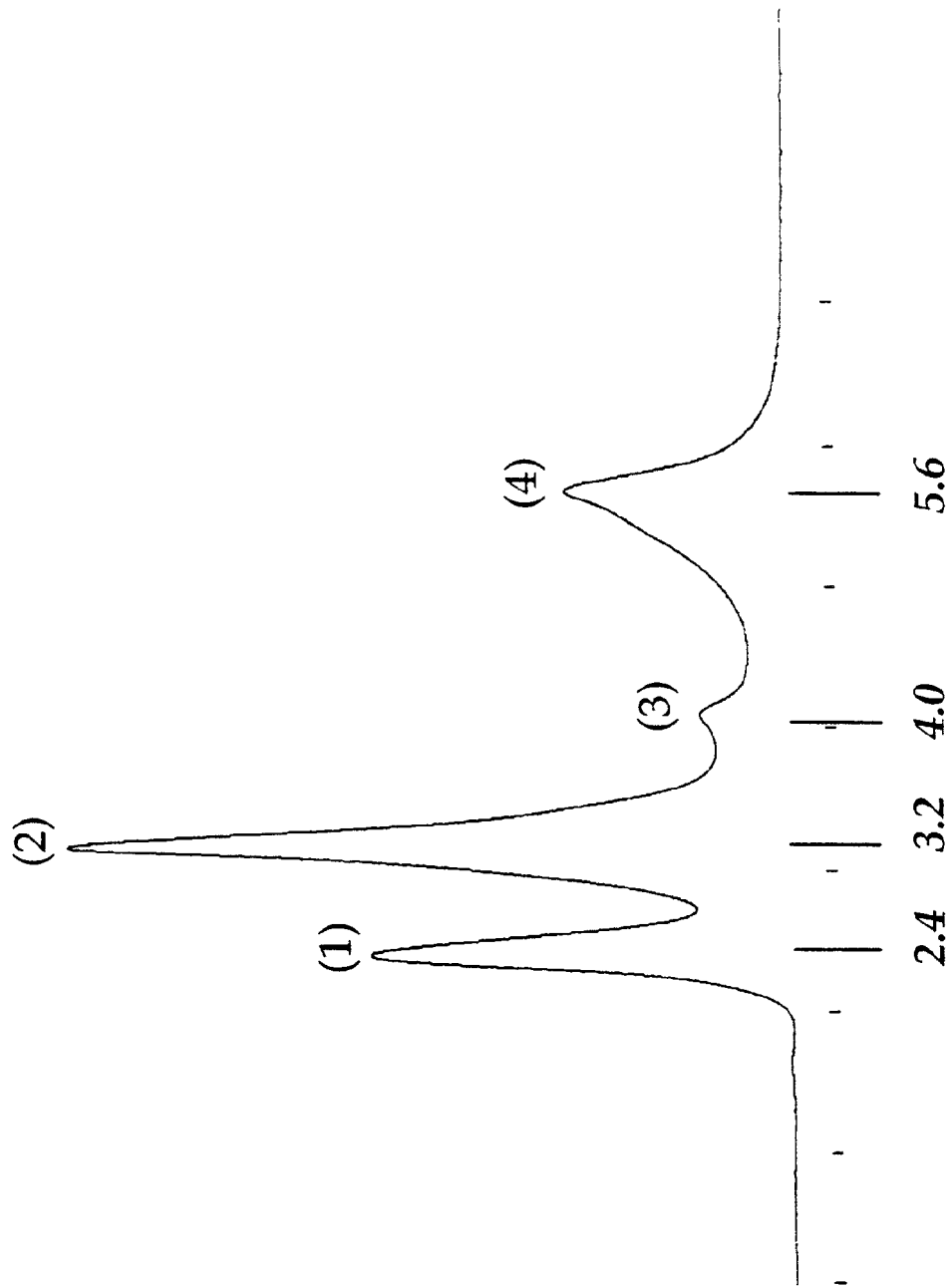
FIG. 19 illustrates the separation of uridine (1), phenol (2), aniline (3), benzene (4), and 4-iodo-nitro benzene (5) on a meso-substituted calix[4]pyrrole column: mobile phase 60% water/40% acetonitrile (v/v); flow rate 0.3 mL/min.; column temperature 25° C.; detection 254 nm (0.100 AUFS).

FIG. 19 illustrates the separation observed between 5 different neutral aromatic compounds: uridine (1), phenol (2), aniline (3), benzene (4), and 4-iodo-nitro benzene (5) on Gel M. In addition to hydrogen-bonding properties, π-π interactions appear to influence separation. It is noteworthy to point out that nucleotides, shown in FIGS. 17 and 18, require a substantially stronger buffer system for elution than the nucleoside, uridine (1), shown in FIG. 19, which requires a weak buffer and is eluted almost immediately.

Figure 22:
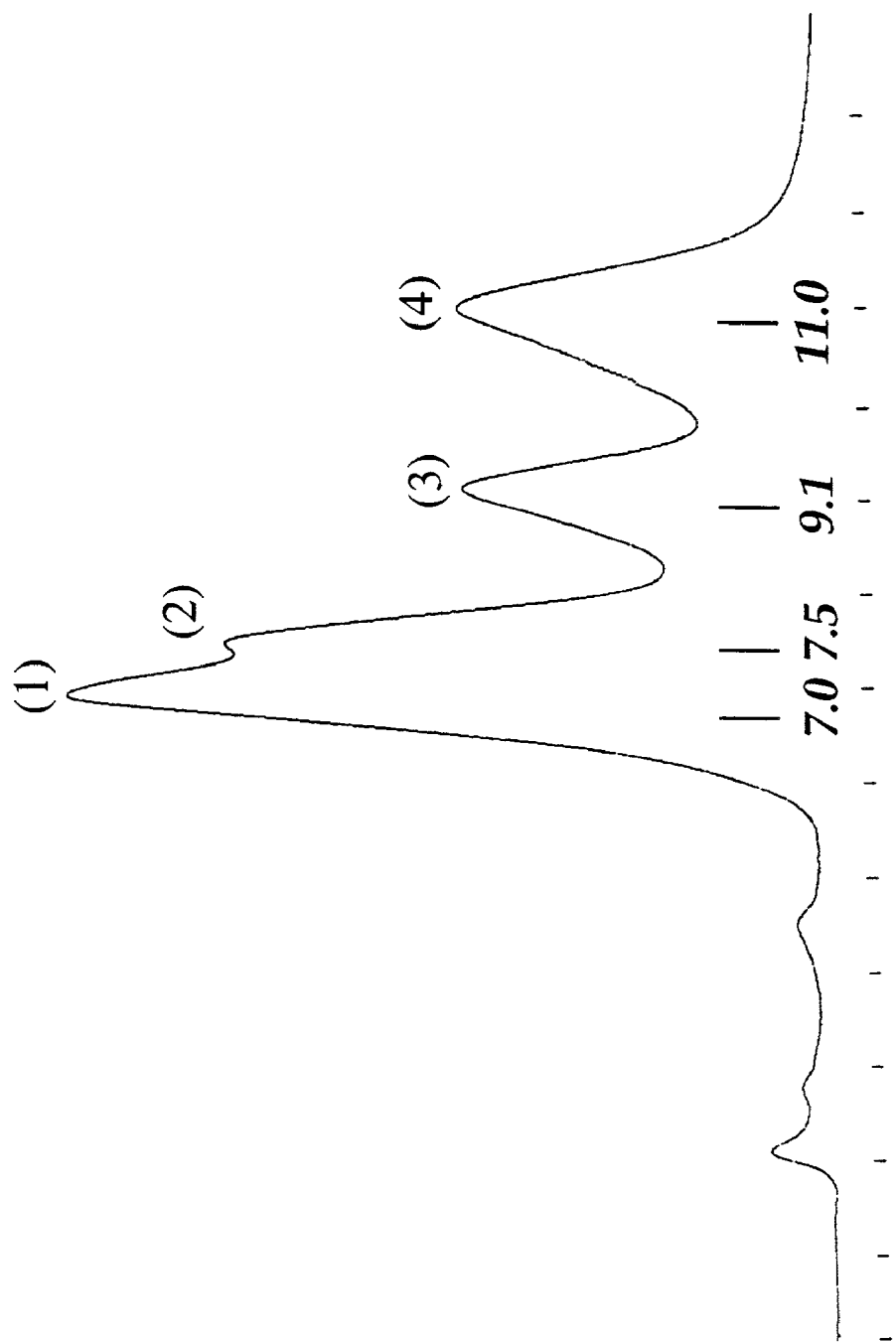
FIG. 22 illustrates the separation of 4-fluorobiphenyl (1), 4,4'-difluorobiphenyl (2), 2,2',3,3',5,5',6,6',-octafluorobiphenyl (3), and perfluorobiphenyl (4) on a meso-substituted calix[4]pyrrole column: mobile 60% water/40% acetonitrile (v/v); flow rate 0.3 mL/min.; column temperature 25° C.; detection 254 nm (0.100 AUFS).
Figure 23:
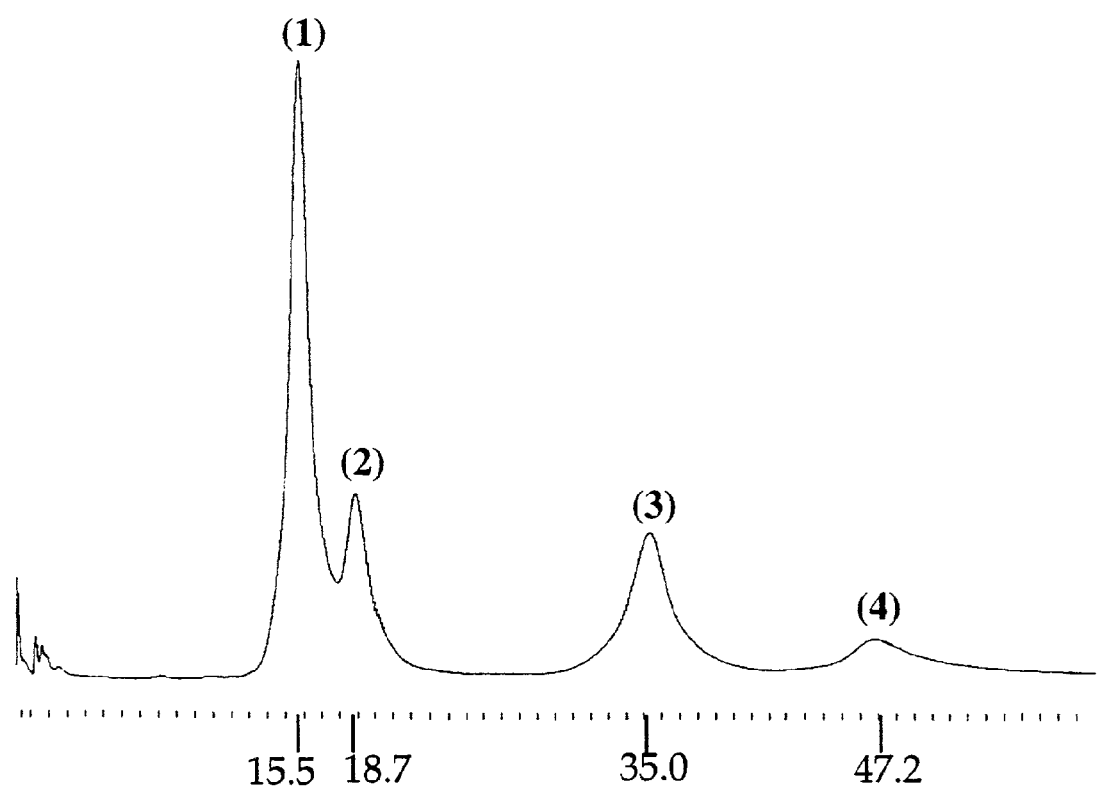
FIG. 23 illustrates the separation of 4-fluorobiphenyl (1), 4,4'-difluorobiphenyl (2), 2,2',3,3',5,5',6,6',-octafluorobiphenyl (3), and perfluorobiphenyl (4) on a β-substituted calix[4]pyrrole column: mobile 76% water/24% acetonitrile (v/v); flow rate 0.2 mL/min.; column temperature 25° C.; detection 254 nm (0.100 AUFS).

Further, the separation of very similar molecules of a class of molecules was carried out. Using a model system analogous to the class of polychlorobiphenyls which are known carcinogens, the separation of polyfluorobiphenyls, a biologically inactive compound, was effected. Demonstrated in FIG. 22, is the separation of four polyfluorobiphenyl compounds; 4-fluorobiphenyl (1), 4,4'-difluorobiphenyl (2), 2,2'3,3',5,5',6,6'-octafluorobiphenyl (3), and perfluorobiphenyl (4) on Gel M and in FIG. 23 on Gel B.

With current interest in antisense oligonucleotide therapy and oligonucleotides as primers and probe molecules, the ability to effectively and efficiently purify usable quantities of these oligomers is of paramount importance. One of the best methods for obtaining large quantities of purified oligonucleotides is high pressure liquid chromatography (HPLC). There are a number of HPLC techniques employed in the purification of oligonucleotides, however, the two most currently used methods are reverse phase- and ion exchange chromatography. These popular methods suffer from practical drawbacks. Purification of medium chain length (12–24) oligonucleotides using reverse phase chromatography must be done using protected substrates. The protecting groups most often used are trityl groups which must be subsequently removed by hydrolysis before use. Additionally, reverse phase chromatography suffers from very long retention times which limits its applicability. Oligonucleotides separated via anion exchange chromatography, while not plagued by the long retention times or additional hydrolysis steps, must be desalted before use.

Figure 24:
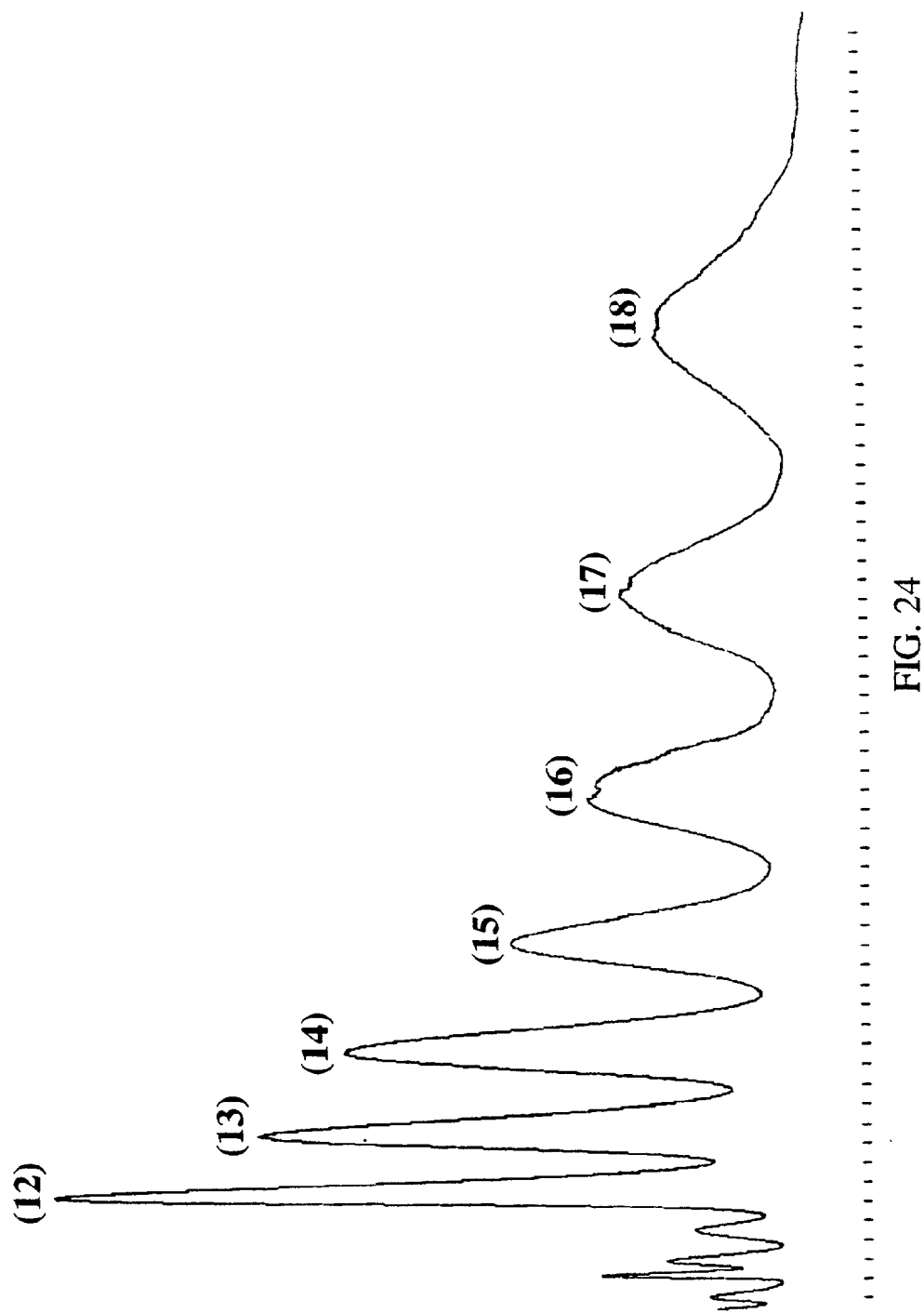
FIG. 24 illustrates the separation of a mixture of polydeoxythymidilates oligomers containing between (12) and (18) base pairs on a meso-substituted calix[4]pyrrole column: mobile phase 50/50 acetonitrile/50 mM phosphate, 250 mM chloride buffer, pH=6.8 (v/v): flow rate 0.4 mL, min.; column temperature 25° C.; detection UV at 265 nm.
Figure 25:
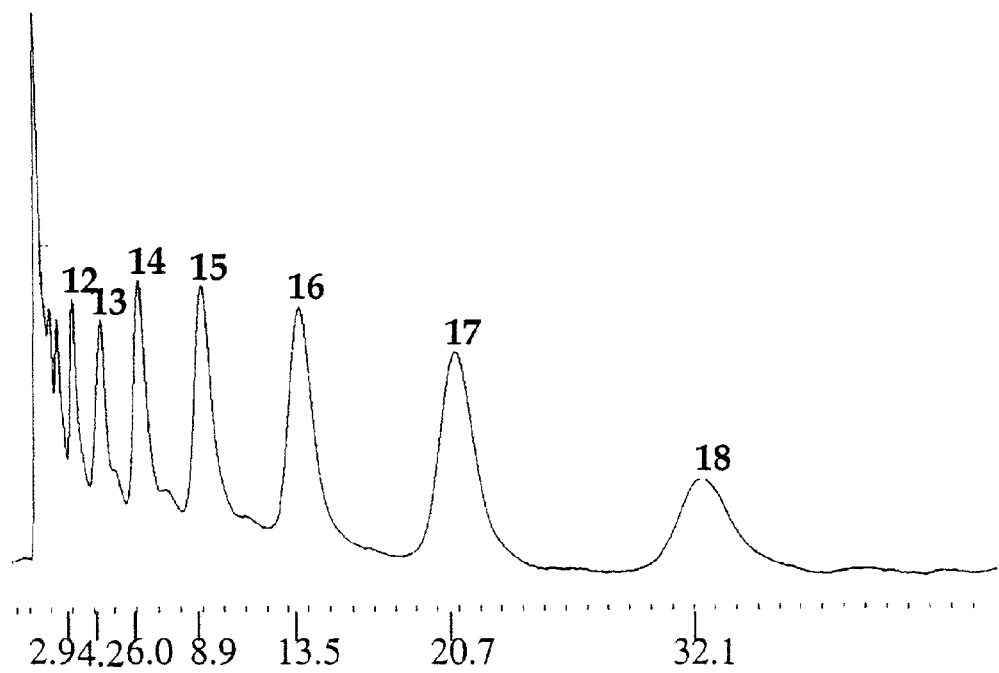
FIG. 25 illustrates the separation of a mixture of polydeoxythymidilates oligomers containing between (12) and (18) base pairs on a β-substituted calix[4]pyrrole column: mobile phase 40/60 acetonitrile/40 mM phosphate, 50 mM chloride buffer, pH=7.0 (v/v), flow rate 0.25 mL/min.; column temperature 25° C.: detection UV at 262 nm (0.100 AUFS).

FIG. 24 illustrates a separation of 12 to 18 base mixture of deoxythymidilates ($dT_{12-18}$) on Gel M and FIG. 25 shows the data for Gel B. Additionally mixtures of deoxythymidilates ($dT_{19-24}$) were successfully separated on both Gel M and Gel B. The calix[4]pyrrole-modified silica gel has some immediate advantages over anion exchange columns and reverse phase columns. With respect to anion exchange chromatography, the large concentrations of salt that is normally need to effect separation is not needed, thereby removing the mandatory desalting step after chromatography of oligonucleotides before using them in biochemical experiments. The primary advantage that the calix[4]pyrroles has over reverse phase columns is the higher resolution and shorter retention times. Additionally, reverse phase chromatography of oligonucleotides is done while they are in a "protected" state and must further be hydrolyzed before use.

Figure 26:
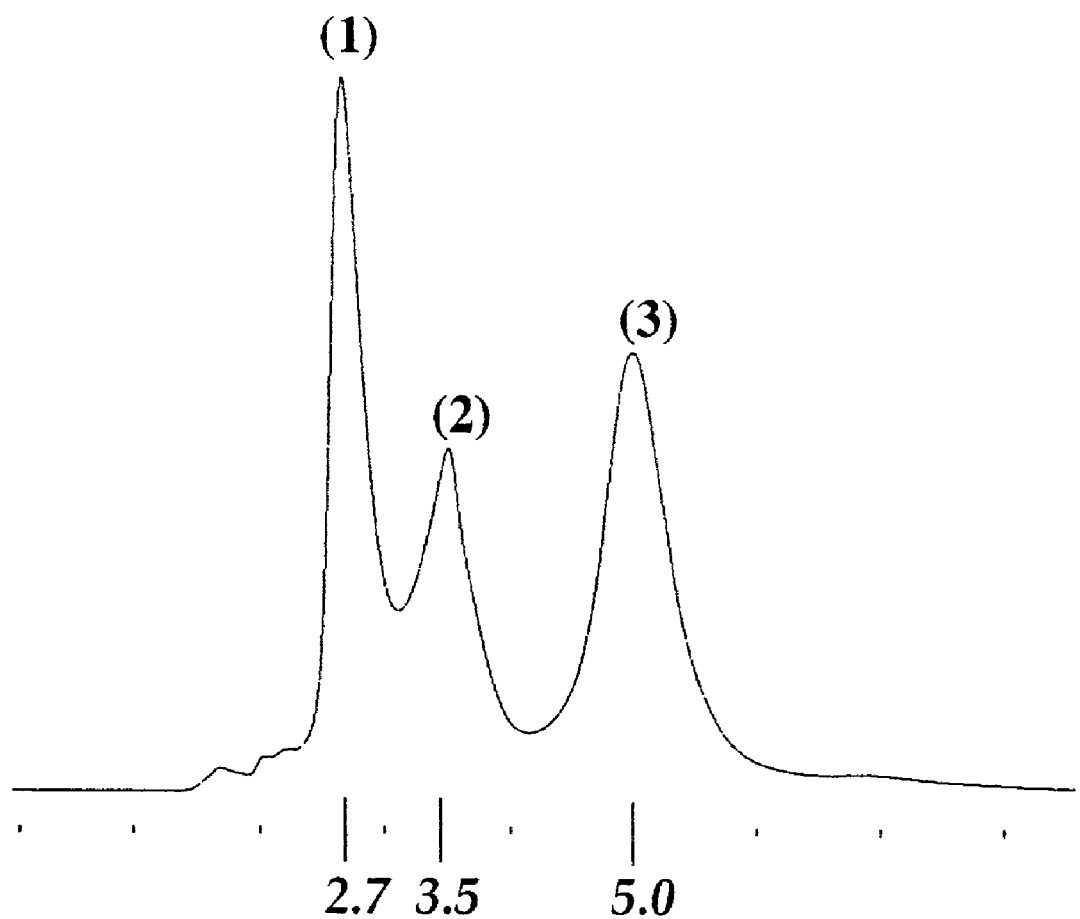
FIG. 26 illustrates the separation of TCTAGA, (1), GCATGC, (2), and CCCGGG, (3), on a meso-substituted calix[4]pyrrole column: mobile phase 50/50 acetonitrile/50 mM sodium phosphate, pH=7.0 (v/v); flow rate 0.4 mL/min.; column temperature 25° C.; detection UV at 265 nm (0.100 AUFS).

The ability of calix[4]pyrroles to distinguish between specific sequences of nucleotide hexamers was then examined. FIG. 26 provides the data where three different oligonucleotide hexamers, GGGCCC, TCTAGA, and GCATGC, were eluted through Gel M resulting in separation of the three hexamers.

Mixtures of pesticides (carbofuran, carbendazim, bromacil, bentazon, carboxin and norflurazon) were successfully separated on Gel M.

Oligonucleotide therapy has been proposed for a wide range of ailments. These include, but are not limited to sickle cell anemia, hypertension, leukemia, cancer, and AIDS. The basic premise of oligonucleotide therapy is to identify the relevant mRNA or DNA strand that is causing the specific problem and synthesizing a short ($\leq 20$ bases) complementary oligonucleotide strand that will bind to the mRNA or DNA, thereby blocking translation or transcription of the genetic material.

Table 7 illustrates the ability of calix[4]pyrrole silica gels M and B to separate tetrabutyl ammonium halides.

TABLE 7

Analysis of Tetrabutylammonium Halides on Calixpyrrole-Substituted Silica Gel

| | Elution Times (minutes) | |
|---|---|---|
| | Silica Gel B | SilicaGel M |
| Chloride[b] | 17.9 (±0.1)[a] | 15.2 (±0.1)[a] |
| Dihydrogen phosphate[b] | 22.0 (±0.1)[a] | 20.1 (±0.1)[a] |

TABLE 7-continued

Analysis of Tetrabutylammonium Halides on Calixpyrrole-Substituted Silica Gel

| | Elution Times (minutes) | |
|---|---|---|
| | Silica Gel B | SilicaGel M |
| Hydrogen sulfate[b] | 16.2 (±0.1)[a] | 16.2 (±0.2)[a] |
| Fluoride[b] | 16.9 (±0.1)[a] | 16.4 (±0.2)[a] |

[a]Times given for individual elution of tetrabutyl ammonium anions. Separation of mixtures was not possible due to broadening of peaks.
[b]Anions were eluted as 1 mM $CH_3CN$ solutions of their tetrabutylammonium salts under the following conditions: Mobile phase, $CH_3CN$; Flow Rate, 0.40 mL/min.; Detection, Conductivity; Column Temperature, 25° C.

The present example primarily refers to silica-bound calixpyrrole, however, the solid support attached to the calix[4]pyrrole is not limited to silica gel. Further solid supports include, but are not limited to, polystyrene, polyacrylamide, Merrifield resins, glass, sepharose, sephadex, agarose, clays, zeolites, and the like, that can be functionalized to allow the formation of a calix[n]pyrrole bonded to a solid support.

Calix[n]pyrroles have been shown to be selective toward a number of different anionic species. In examples described herein, calix[4]pyrrole has shown differing affinities for anionic species including fluoride, chloride, bromide, iodide, phosphates, carboxylates, arsenates and sulfates.

Macrocycles of the present invention may be used to generate ion selective electrodes in a further use embodiment. Data illustrated in Table 8 for anion selective electrodes synthesized by the present inventors indicate that the selectivity and preferential binding observed in solution and in separation chemistry, described in examples herein, is consistent with anion selective electrode technology.

TABLE 8

Anion Selectivity for a Calix[4]pyrrole Based Membrane[a,b]

| | log $K^{pot}_{i/j}$ |
|---|---|
| Fluoride | 0 |
| Chloride | −0.7 |
| Bromide | −1.0 |
| Iodide | +0.4 |
| Hydrogen Sulfate | −4.4 |
| Dihydrogen Phosphate | −1.7 |
| Hydrogen Sulfite | −0.4 |
| Nitrate | −0.5 |
| Nitrite | −1.8 |
| Acetate | −0.9 |
| Benzoate | +0.02 |
| Benzene sulfonate | −0.5 |
| L-Alanine | −1.7 |
| L-Aspartate | −1.6 |
| L-Tryptophan | −0.5 |
| L-Hystidine | −1.6 |
| D-Serine | −1.1 |
| DL-Alanine | −1.2 |
| DL-Threonine | −1.4 |
| Chromotropate | −1.0 |
| 5-Formyl-2-furansulfonate | −0.6 |

[a]Selectivity coefficients determined relative to fluoride, log $K^{pot}_{i/j}$, using the separate solution method.
[b]Membrane compositions: 3% (w/w) calix[4]pyrrole, 22% (w/w) PVC, 75% (w/w) 2-o-nitrophenyloctyl ether. Internal electrolyte was 0.1 M NaCl and 0.001 M NaF.

Methods of making calix[n]pyrrole-ion-selective electrodes include, but are not limited to, the following examples: attaching, or immobilizing a functionalized calix[n]pyrrole to a functionalized polymer and further coating this polymer to an electrode that is sensitive to changes in ionic strength; immobilizing the calix[n]pyrrole in a plasticizers and encasing the mixture in a membrane surrounding an electrode that is sensitive to changes in ionic strength; covalently attaching the calix[n]pyrroles to an electrode that is sensitive to changes in ionic strength; or coating the electrode with a layer of calix[n]pyrroles containing electropolymerizable functional groups, including but not limited to, pyrrole, thiophene or vinyl, and polymerizing the coating on to the electrode.

EXAMPLE 11

Biomedical Applications

The anion and neutral binding properties of calix[n]pyrrole, calix[m]pyridino[n]pyrrole and calix[m]pyridines allow for a number of useful applications within the biomedical field. Applications include, but are not limited to, drug-delivery systems, anion transport through membranes, selective anion channel formation, dialysis, blood filtration and viral inhibition.

Cystic fibrosis is the most common lethal genetic disease among Caucasians, affecting one out of 2,500 infants in the U.S. The disease is characterized by the inability to produce properly-functioning chloride anion channels. The calix[n]pyrroles have been demonstrated herein to bind chloride via hydrogen bonding. An array of calix[n]pyrroles or calix[m]pyridino[n]pyrroles could be designed to span a membrane requiring selective chloride transport. Chloride anion is bound and released appropriately by calix[4]pyrrole as demonstrated in Example 10. Calix[4]pyrrole has also demonstrated the ability to transport anions through an "artificial" dichloromethane membrane in Pressman U-tube experiments. An array of calix[n]pyrroles is expected to transfer anions by "handing off" the anion to the next calix[n]pyrrole.

Calix[n]pyrroles can also be used to transport the anion through the membrane by acting as discrete carriers. Referring to the U-tube data, calix[4]pyrrole has demonstrated the ability to transfer charged molecules through organic membranes. The chloride anion could be transferred through a cell membrane in this way thereby alleviating the problem of chloride transport and ultimately treating the disorder.

Another application of anion transport is use of the macrocycles of the present invention as a drug delivery system. Many potential anti-viral agents which display activity ex-vivo are phosphorylated nucleosides. These species are too polar to pass through cell wall membranes and are thus inactive in vivo.

Calix[4]pyrrole has been shown to transport anionic species effectively through "artificial" membranes. The present inventors have synthesized a number of nucleotide conjugates as examples of nucleobase-substituted calix[n]pyrroles. The possibilities of nucleotide substitution include, but are not limited to any of the naturally occurring purine or pyrimidine nucleobases. Additionally, modified versions include any number of purine- or pyrimidine- based synthetic molecules capable of addition to a calix[4]pyrrole core. "Nucleobase," as used herein, means a purine or pyrimidine base, nucleoside (saccharide derivative), nucleotide (saccharide-poly- or mono-phosphate derivative) and natural and synthetic analogues thereof. Attachment of a nucleobase to the calix[n]pyrrole may occur at a functional group of the β-position, a pyrrolic-nitrogen, or meso-position of the calix[n]pyrrole. One nucleobase may be attached, however, any number or diversity of nucleobases may be attached to the calix[n]pyrrole. Attachment can occur using methods such as: amide bond formation, Stille coupling, ester formation, or the like. The nucleobase appended calixpyrrole will coordinate to both the phosphate group and nucleoside of the anti-viral drug, forming a hydrophobic complex which may pass through cell wall membranes and decomplex, releasing the drug into the interior of the cell.

Examples of nucleobase-calix[4]pyrrole conjugates synthesized by the present inventors are provided as macrocycles 41 and 42.

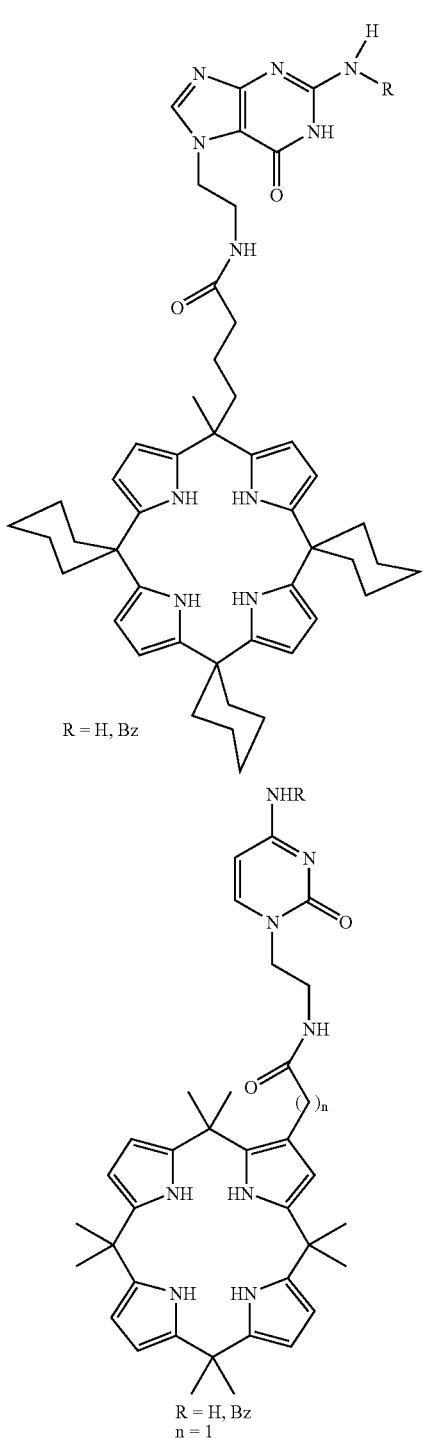

R = H, Bz
n = 1

Preparation of nucleobase substituted calix[n]pyrroles 41 and 42. Calixpyrrole monoacid (1 mmol) was dissolved in dry dichloromethane (25 mL), (chloroform, acetonitrile, DMF, 1,2-dichloroethane can also be used). The solution was activated with 2 molar equivalents (per one acid group) of the activating agent diisopropylcarbodiimide at room temperature in the presence of five molar percent of 1-hydroxybenzotraizole and 4-dimethylaminopyridine. Two molar equivalents per carboxy unit of an aminoethyl nucleobase derivative (nucleobase protected) were added. The reaction mixture was stirred at room temperature for 24–36 hours. Acetic acid (0.5 mL) was added, followed by multiple washings with a 3% hydrochloric acid solution, water, a 5% solution of sodium hydrogencarbonate and water. After drying over sodium sulfate the product was obtained by crystallization or flash chromatography on silica gel. Removal of the N-protecting group was done using standard procedures. The removal of trityl- and benzyl-protecting groups were achieved using trifluoroacetic acid for trityl and and ammonia in methanol for benzyl protecting groups.

Studies have demonstrated that these nucleobase-calix[4]pyrrole conjugates are not only efficient carriers, but selective carriers as well. Using a cytosine-calix[4]pyrrole conjugate to transport a mixture of adenosine monophosphate, cytidine monophosphate, guanidine monophosphate, thymidine monophosphate and uridine monophosphate, a transfer ratio of 5:1:125:8:7 was observed. The guanidine monophosphate was transported from one aqueous phase to another 10–100 times better across the dichloromethane model membrane as a result of having complementary binding with the cytosine of the cytosine-calix[4]pyrrole conjugate. In addition to being bound to a single nucleobase, calix[n]pyrroles could be attached to oligonucleotides using known technology. Calix[n]pyrrole-oligonucleotide conjugates could then be used to bind such substrates as mRNA or DNA preventing transcription or translation. This mode of binding could be used in antisense therapy, or viral inhibitation. In the case of viral inhibition, the binding site of the virus would be identified and the complementary calix[n]pyrrole-oligonucleotide conjugates would be synthesized.

Calix[n]pyrroles have utility for ex vivo applications as well. Kidney failure is a condition that affects a significant portion of the people in the world due to various ailments. The present example provides for the use of calix[n]pyrroles and calix[m]pyridino[n]pyrroles for dialysis or filtration of ex vivo bodily fluids. Phosphates, chloride, and other toxins contained in the blood or other bodily fluids may be removed by exposure to macrocycles of the present invention since said macrocycles have demonstrated the ability to bind anionic and neutral molecules in the solid state, in solution and when attached to a solid support. Further, calix[n]pyrroles can be functionalized to be anion-specific. The present inventors have shown that under chromatographic conditions where anions are bound, proteins and other biomolecules were unhindered in passage through a column, for example.

Calix[n]pyrroles could also be used in dialysis. Current dialysis employs an anion gradient to bring anions across a membrane, thereby establishing an equilibrium. Calix[n]pyrroles could be used to bind the anions once they came across the membrane forcing the equilibrium to shift in favor of additional waste anion removal by not allowing an equilibrium to form. The calix[n]pyrroles could either water soluble and partioned on one side of a membrane or bound to a solid support to prevent diffusion into the blood supply.

Calix[n]pyrrole could be attached to a biologically-inert solid support and used to filter toxins out of the blood. These toxins include, but are not limited to, drug metabolites (for use in drug overdoses) and anionic wastes. Another endogenous material that can function as toxin is urea. Its removal using this approach illustrated could be used in the treatment of gout.

Additionally calixpyrroles could be used in imaging. $^{99m}$Tc is an high energy form of technetium used in imaging for the detection of tumors. $^{99m}$TcO$_4$— or any other anion containing $^{99m}$Tc may be coodinated to a calix[n]pyrrole and used as an imaging agent.

EXAMPLE 12

Environmental Remediation

Radioactive waste poses a serious problem to the environment. Current technology generates large amounts of secondary solid waste for disposal. Separation and concentration of these wastes is of paramount importance, especially due to long half-lives, and inadequate methods of storage such as sludges or underground tanks of wastewater. Half-life examples for Tc-99, Ni-63, Cs-137, and Sr-90 are 213,000 years, 100 years, 30 years and 28 years, respectively.

Certain of the radioactive metallic wastes exist in an oxidized anionic form and are therefore soluble in aqueous solutions. For example, technetium exists as TcO$_4$—, and nickel, strontium, and cesium can exist in oxidized anionic forms.

Calix[4]pyrrole has demonstrated the ability to bind phenyl arsenate in aqueous media. In addition, FIG. 16 illustrates the ability of calix[4]pyrrole to separate four different phenyl anions from a mixture thereof.

In a column embodiment, solid-supported calix[n]pyrrole could be used to separate out metallic anions from a stream passing through a column. The bound anions could then be eluted from the solid support, and the concentrated eluate is able to be stored in a smaller volume.

In a batch embodiment, solid support-bound calix[n]pyrrole could be mixed with a waste solution containing an anion to be removed and the mixture then filtered as a method of extracting the waste anions out of solution. Additionally, a multi-phase extraction system is envisioned where calix[n]pyrrole in a first phase extracts anionic waste from another phase, and the waste then is separated for storage or disposal.

The present inventors envision, because of the relatively fast "on-off" rate that is observed with calix[4]pyrrole, that the radioactive waste metal could be "washed" off of the solid support for solid support reuse. Current technology uses materials with high binding constants for removal of metallic oxyanion waste. This procedure is efficient for removal of the waste from contaminated liquid, however, the waste is converted to solid waste and must still be disposed of.

Molecules that can be removed from an environmental source are those ions and molecular species that calix[n]pyrrole will bind as described herein. In particular, for application to inorganic metal oxoanions, arsenate, tungstenate, pertechnetate, borate, or the like, may be removed. Removal of pertechnetate from nuclear waste is a particularly preferred application of the present technology. Types of solid supports for attaching calix[n]pyrrole include, but are not limited to, those supports provided in Example 10.

Eutrophication is a serious problem for bodies of water near agricultural lands and urban areas. The accumulation of phosphates and nitrates from fertilizers in lakes, rivers and inland waterways causes toxic algal blooms that poison the water. Algal blooms are also thought to be toxic for humans. Removal of such anions by use of macrocycles of the present invention in a water-treatment plant, for example, would purify the water and provide it for human use and generations of the future.

Purification of domestic water supplies is an increasing necessity in densely populated areas. The macrocycles of the present invention would be useful in filters for attachment to home water supplies for removal of anionic pollutants such as, but not limited to, fluoride, phosphate and nitrate.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the -invention as defined by the appended claims.

What is claimed is:

1. A pharmaceutical composition comprising a pharmaceutically acceptable carrier and a calix[4]pyrrole macrocycle consisting of structure I:

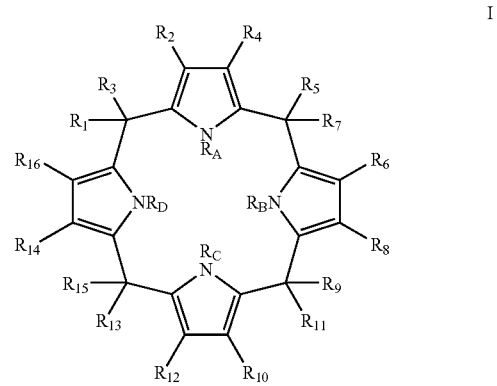

that has 4 pyrrole rings linked in a positions via sp$^3$ hybridized meso-carbon atoms, wherein neither non-pyrrole substituent of the meso-carbon atoms is hydrogen, at least one pyrrole ring comprises a non-hydrogen β-substituent and the macrocycle is noncovalently-complexed to a halide anion;

wherein $R_1$–$R_{16}$ are independently substituents as listed in paragraph i) below, and $R_A$–$R_D$ are independently substituents as listed in paragraph ii) below;

i) hydrogen, halide, hydroxyl, alkyl, alkenyl or alkynyl;

ii) hydrogen or alkyl;

wherein odd-numbered R substituents are other than hydrogen and at least one even-numbered R substituent is other than hydrogen.

2. A pharmaceutical composition comprising a pharmaceutically acceptable carrier and a calix[4]pyrrole macrocycle consisting of structure I:

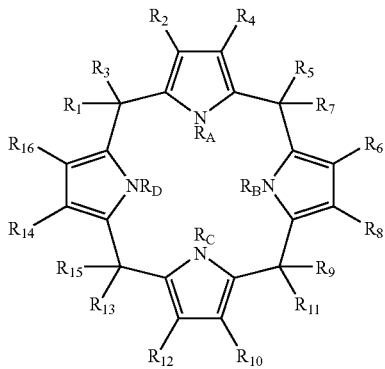

I that has 4 pyrrole rings linked in a positions via sp³ hybridized meso-carbon atoms, wherein neither non-pyrrole substituent of the meso-carbon atoms is hydrogen, at least one pyrrole ring comprises a non-hydrogen-substituted nitrogen atom and the macrocycle is noncovalently-complexed to a halide anion;
wherein $R_1$–$R_{16}$ are independently substituents as listed in paragraph i) below, and $R_A$–$R_D$ are independently substituents as listed in paragraph ii) below;
  i) hydrogen, halide, hydroxyl, alkyl, alkenyl, or alkynyl;
  ii) hydrogen or alkyl;
wherein odd-numbered R substituents are other than hydrogen and at least one of $R_A$–$R_D$ is other than hydrogen.

3. A pharmaceutical composition comprising a pharmaceutically acceptable carrier and a calix pyrrole macrocycle consisting of structure I:

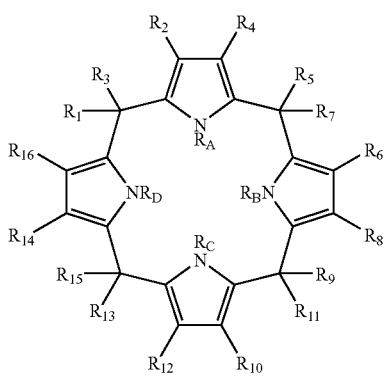

I that has 4 pyrrole rings linked in a positions via sp³ hybridized meso-carbon atoms, wherein neither non-pyrrole substituent of the meso-carbon atoms is hydrogen and the macrocycle is noncovalently-complexed to a halide anion;
wherein $R_1$–$R_{16}$ are independently substituents as listed in paragraph i) below, and $R_A$–$R_D$ are independently substituents as listed in paragraph ii) below;
  i) hydrogen, halide, hydroxyl, alkyl, alkenyl, or alkynyl;
  ii) hydrogen or alkyl;
wherein odd-numbered R substituents are other than hydrogen.

4. The pharmaceutical composition of claim 3 wherein the halide anion is chloride.

5. The pharmaceutical composition of claim 3 wherein the halide anion is fluoride.

6. The pharmaceutical composition of claim 3, wherein the halide anion is selected from the group consisting of chloride and fluoride.

7. The pharmaceutical composition of claim 1, wherein the halide anion is selected from the group consisting of chloride and fluoride.

8. The pharmaceutical composition of claim 2, wherein the halide anion is selected from the group consisting of chloride and fluoride.

9. A composition comprising a calix[4]pyrrole macrocycle consisting of structure I:

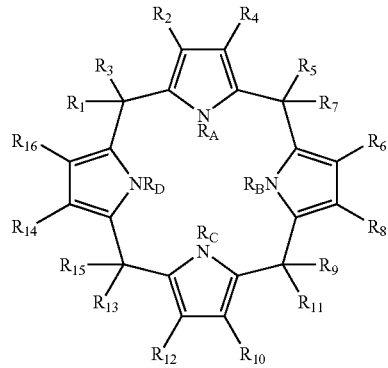

I that has 4 pyrrole rings linked in α positions via sp³ hybridized meso-carbon atoms, wherein neither non-pyrrole substituent of the meso-carbon atoms is hydrogen, at least one pyrrole ring comprises a non-hydrogen β-substituent and the macrocycle is noncovalently-complexed to a halide anion; wherein $R_1$–$R_{16}$ are independently substituents as listed in paragraph i) below, and $R_A$–$R_D$ are independently substituents as listed in paragraph ii) below;
  i) hydrogen, halide, hydroxyl, alkyl, alkenyl or alkynyl;
  ii) hydrogen or alkyl;
wherein odd-numbered R substituents are other than hydrogen and at least one even-numbered R substituent is other than hydrogen; and wherein the macrocycle is attached to a solid support.

10. A composition comprising a calix pyrrole macrocycle consisting of structure I:

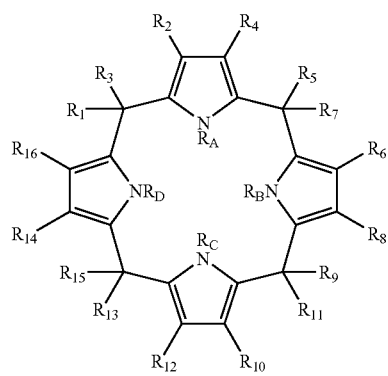

I that has 4 pyrrole rings linked in a positions via sp³ hybridized meso-carbon atoms, wherein neither non-pyrrole substituent of the meso-carbon atoms is hydrogen, at least one pyrrole ring comprises a non-hydrogen-substituted nitrogen atom and the macrocycle is noncovalently-complexed to a halide anion, wherein R₁–R₁₆ are independently substituents as listed in paragraph i) below, and R_A–R_D are independently substituents as listed in paragraph ii) below;
  i) hydrogen, halide, hydroxyl, alkyl, alkenyl, or alkynyl;
  ii) hydrogen or alkyl;
wherein odd-numbered R substituents are other than hydrogen and at least one of R_A–R_D is other than hydrogen; and wherein the macrocycle is attached to a solid support.

11. A composition comprising a calix pyrrole macrocycle consisting of structure I:

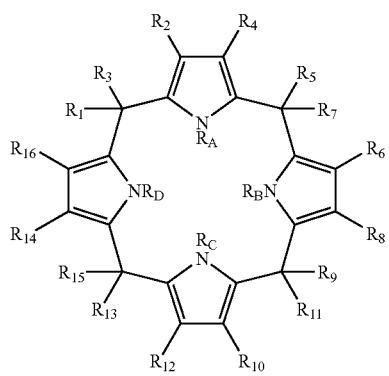

that has 4 pyrrole rings linked in cc positions via sp³ hybridized meso-carbon atoms, wherein neither non-pyrrole substituent of the meso-carbon atoms is hydrogen and the macrocycle is noncovalently-complexed to a halide anion; wherein R₁–R₁₆ are independently substituents as listed in paragraph i) below, and R_A–R_D are independently substituents as listed in paragraph ii) below;
  i) hydrogen, halide, hydroxyl, alkyl, alkenyl, or alkynyl;
  ii) hydrogen or alkyl;
wherein odd-numbered R substituents are other than hydrogen; and wherein the macrocycle is attached to a solid support.

12. The composition of claim 9, wherein the halide anion is selected from the group consisting of chloride and fluoride.

13. The composition of claim 10, wherein the halide anion is selected from the group consisting of chloride and fluoride.

14. The composition of claim 11, wherein the halide anion is selected from the group consisting of chloride and fluoride.

15. The composition of claim 9, wherein the solid support is selected from the group consisting of silica gel, alumina, polyacrylamide, polystyrene, sepharose, sephadex, agarose, clay, zeolite, Merrifield resin, and glass.

16. The composition of claim 15, wherein the solid support is a silica gel.

17. The composition of claim 16, wherein the silica gel is functionalized.

18. The composition of claim 17, wherein the functionalized silica gel is selected from the group consisting of aminopropyl silica gel, carboxylalkylated silica gel, chloroethylated silica gel and chloroalkylated silica gel.

19. The composition of claim 9, wherein the solid support is in a form of a capillary electrophoresis tube, an electrophoresis gel, a chromatography column, and a thin layer chromatographic support.

20. The composition of claim 10, wherein the solid support is selected from the group consisting of silica gel, alumina, polyacrylamide, polystyrene, sepharose, sephadex, agarose, clay, zeolite, Merrifield resin, and glass.

21. The composition of claim 20, wherein the solid support is a silica gel.

22. The composition of claim 21, wherein the silica gel is functionalized.

23. The composition of claim 22, wherein the functionalized silica gel is selected from the group consisting of aminopropyl silica gel, carboxylalkylated silica gel, chloroethylated silica gel and chloroalkylated silica gel.

24. The composition of claim 10, wherein the solid support is in a form of a capillary electrophoresis tube, an electrophoresis gel, a chromatography column, and a thin layer chromatographic support.

25. The composition of claim 11, wherein the solid support is selected from the group consisting of silica gel, alumina, polyacrylamide, polystyrene, sepharose, sephadex, agarose, clay, zeolite, Merrifield resin, and glass.

26. The composition of claim 25, wherein the solid support is a silica gel.

27. The composition of claim 26, wherein the silica gel is functionalized.

28. The composition of claim 27, wherein the functionalized silica gel is selected from the group consisting of aminopropyl silica gel, carboxylalkylated silica gel, chloroethylated silica gel and chloroalkylated silica gel.

29. The composition of claim 11, wherein the solid support is in a form of a capillary electrophoresis tube, an electrophoresis gel, a chromatography column, and a thin layer chromatographic support.

* * * * *